(12) United States Patent
Suzuki et al.

(10) Patent No.: US 7,968,733 B2
(45) Date of Patent: Jun. 28, 2011

(54) PYRROLIDINE ANALOGUE FOR PREVENTING NEUROGENIC PAIN AND METHOD FOR PRODUCTION THEREOF

(75) Inventors: Masaaki Suzuki, Gifu (JP); Kyouji Furuta, Gifu (JP); Toshiaki Minami, Takatsuki (JP); Seiji Ito, Moriguchi (JP)

(73) Assignees: Gifu University, Gifu-shi (JP); Kansai Medical University, Moriguchi-shi (JP); Osaka Medical College, Takatsuki-shi (JP)

( * ) Notice: Subject to any disclaimer, the term of this patent is extended or adjusted under 35 U.S.C. 154(b) by 0 days.

(21) Appl. No.: 12/308,067

(22) PCT Filed: May 23, 2007

(86) PCT No.: PCT/JP2007/060489
§ 371 (c)(1),
(2), (4) Date: Dec. 5, 2008

(87) PCT Pub. No.: WO2007/142028
PCT Pub. Date: Dec. 13, 2007

(65) Prior Publication Data
US 2009/0306407 A1    Dec. 10, 2009

(30) Foreign Application Priority Data
Jun. 6, 2006   (JP) ................................. 2006-157874

(51) Int. Cl.
*C07D 207/00* (2006.01)
(52) U.S. Cl. ..................................................... 548/532
(58) Field of Classification Search ............. 548/532
See application file for complete search history.

(56) References Cited

U.S. PATENT DOCUMENTS
4,462,943 A   7/1984   Petrillo, Jr. et al.

FOREIGN PATENT DOCUMENTS
| CN | 1711081 A | 12/2005 |
| JP | 57-116046 | 7/1982 |
| JP | 2006-516115 | 5/2004 |
| JP | 2007-153755 | 6/2007 |
| WO | WO-2004/039367 | 5/2004 |

OTHER PUBLICATIONS

Toshiaki Minami et al., "Acute and late effects on induction of allodynia by acromelic acid, a mushroom poison related structurally to kainic acid," British Journal of Pharmacology, 2004, vol. 142, pp. 679-688.

Katsuhiro Konno et al., "Isolation and Structure of Acromelic Acid A and B. New Kainoids of *Clitocybe Acromelalga*," Tetrahedron Letters 1983, vol. 24, pp. 939-942.

Katsuhiro Konno et al., "Acromelic Acids A and B. Potent Neuroexcitatory Amino Acids Isolated from *Clitocybe acromelalga*," Journal of the American Chemical Society 1988, vol. 110, pp. 4807-4815.

Kyoji Furuta, "A simple acromelic acid analog potentially useful for receptor photoaffinity labeling and biochemical studies," Tetrahedron Letters 2004, vol. 45, pp. 3933-3936.

Jack E. Baldwin et al., "The synthesis of 4-arylsulfanyl-substituted kainoid analogues from *trans*-4-hydroxy-L-proline," Tetrahedron, 2001, vol. 57, No. 37, pp. 7991-7997.

Caplus 2005, vol. 19, No. 2, 126-130 (1 page).

Masako Soen et al., "A synthetic kainoid, (2S, 3R, 4R)-3-carboxymethyl-4-(phenylthio)pyrrolidine-2-carboxylic acid (PSPA-1) serves as a novel anti-allodynic agent for neuropathic pain," European Journal of Pharmacology, vol. 575, 2007, pp. 75-81 and cover page.

International Search Report dated Sep. 4, 2007, issued on PCT/JP2007/060489.

Office Action dated Jan. 19, 2011, issued for the Chinese patent application No. 200780020803.1 and English translation thereof.

*Primary Examiner* — Rebecca L Anderson
*Assistant Examiner* — Samantha L Shterengarts
(74) *Attorney, Agent, or Firm* — Edwards Angell Palmer & Dodge LLP

(57) ABSTRACT

To provide a pyrrolidine analogue having an inhibitory activity on the induction of allodynia, a method for producing the pyrrolidine analogue, and an agent for preventing a neurogenic pain.

A pyrrolidine analogue which is a compound represented by the general formula (I) [wherein HOOC-φ represents an aromatic substituent having at least one carboxy group attached to the benzene ring] or a salt or ester of the compound. The compound has a potent inhibitory effect on the induction of allodynia.

4 Claims, 3 Drawing Sheets

PYRROLIDINE ANALOGUE FOR PREVENTING NEUROGENIC PAIN AND METHOD FOR PRODUCTION THEREOF

TECHNICAL FIELD

The present invention provides pyrrolidine analogues that prevent neuropathic pain such as allodynia, and methods for preparing the compounds.

BACKGROUND ART

Pain is generally classified into three groups: physiological pain such as that caused when a needle pricks skin; inflammatory pain; and neuropathic pain. The neuropathic pain is due to nerve injury and is an intractable disease accompanied by symptoms of spontaneous pain, hyperalgesia, and allodynia, etc. Non-steroidal anti-inflammatory drugs (NSAIDs) and opioids such as morphine often do not exert their analgesic effect on the neuropathic pain. While little is known about pathogenesis of such neuropathic pain, emerging studies of persistent allodynia caused by nerve injury indicate involvement of spinal glutamate receptors, suggesting that regulation of the signal transduction mediated by receptors would result in inhibition of neuropathic pain.

In a related study, acromelic acids (isomeric acromelic acid A and B which are different in the substitution pattern), isolated from a poisonous mushroom, *Clitocybe acromelalga*, have been found to induce severe allodynia by intrathecal administration in mice (Non-patent document 1). Acromelic acids are known to induce neuronal excitotoxicity in the central nervous system.

[Chemical Formula 1]

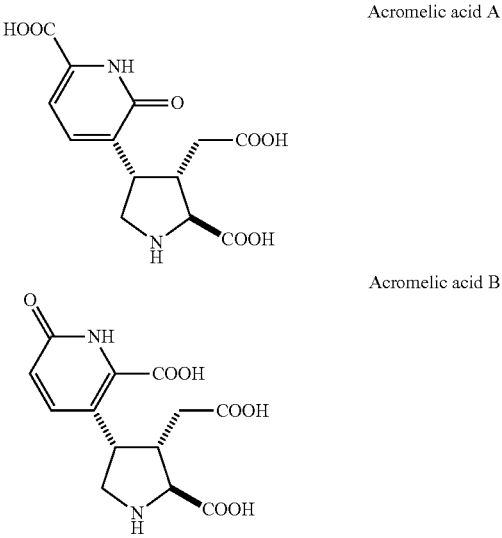

Acromelic acid A

Acromelic acid B

The above-mentioned acromelic acids include a structure like that of glutamic acid, and therefore, are considered to exert their activities through glutamate receptors. However, acromelic acids are also reported to show selectivity to lower spinal cord and specifically destroy spinal interneuron, the first relay point in pain-transmission. These findings are inconsistent with what has been reported for the other glutamate receptor agonists in in vivo behavioral and pathological effects, suggesting the possible existence of novel acromelic acid receptor. Indeed, there are some reports suggesting a novel acromelic acid receptor based on in vivo behavioral and pathological studies of acromelic acids. Nevertheless, the details are still unknown.

Thus, acromelic acids are useful compounds as an important biochemical tool for investigating the pathogenesis of neuropathic pain and elulcidating the function of various neural receptors including glutamate receptors and the like. It is, however, extremely laborious to extract acromelic acids from *Clitocybe acromelalga*. Moreover, only a trace of acromelic acids can be obtained, far from the amount required for use as an experiment tool (Non-patent documents 2 and 3).

Although there have been some reports of chemical synthesis of acromelic acids, the proline framework of the compounds possessing asymmetric carbons at the 2, 3 and 4-positions makes it difficult to synthesize them in large quantity with complete control of stereochemistry, especially in stereoselective introduction of the carbon substituent at the 4-position of the proline framework.

In order to explore the mechanism of action of neural receptors, the present inventors synthesized the following proline analogue (a) having a similar structure to acromelic acids but with an azide group introduced as a photo-sensitive probe, and examined its physiological activity. As a result, it was found that the compound exhibits the same degree of allodynia-inducing activity as that of acromelic acids (Non-patent document 4).

[Chemical Formula 2]

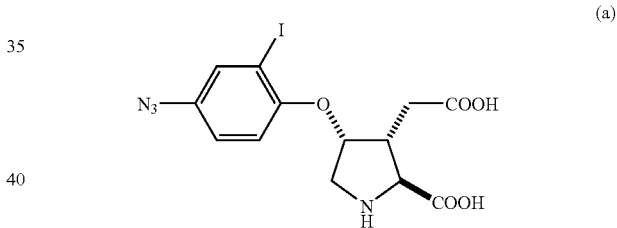

(a)

The present inventors further developed proline analogues that exhibit allodynia-inducing activity and methods for preparing them, and have already filed a patent application thereof (Japanese Application No. 2005-347711). With that invention, a large amount of proline analogues that exhibit allodynia-inducing activity can be readily provided, which may serve in elucidating the molecular mechanism of neuropathic pain and function of neurol receptors including glutamate receptors.

Generally, in order to understand biosignal transduction mechanism, not only agonists that trigger the activation of certain receptors but also antagonists that inhibit the receptor function are a useful tool and thus they needs to be developed. Furthermore, creation of compounds which can inhibit the action of acromelic acids provides not only molecular probes for elucidation of the receptor function involved in neuropathic pain, but also possible therapeutic agents or seeds compounds for neuropathic pain treatment. However, any compounds that exhibit such inhibitory activity have not been discovered. In Patent documents 1 and 2, although the description is found that some proline analogues, which are similar to but distinct from the pyrrolidine analogues of the present invention, can be used as therapeutic agents for treatment of pain disorders, any experimental data demonstrating their pharmacological effects used in the treatment of pain disorders are not provided (Patent documents 1 and 2).
[Non-patent document 1]
British Journal of Pharmacology, 2004, 142, 679-688
[Non-patent document 2]
Tetrahedron Letters 1983, 24, 939-942
[Non-patent document 3]
Journal of the American Chemical Society 1988, 110, 4807-4815
[Non-patent document 4]
Tetrahedron Letters 2004, 45, 3933-3936
[Patent document 1]
WO2004/039367
[Patent document 2]
Japanese Patent Publication No. 2006-516115

DISCLOSURE OF THE INVENTION

Problems to be Solved by the Invention

The present invention was made in view of the above existing problematic situations, and its targeted problem to be solved is to provide pyrrolidine analogues that exhibit inhibitory activity for allodynia induction, their preparation, as well as their use as agents for preventing neuropathic pain.

Means for Solving the Problems

The present inventors synthesized a series of compounds that have similar structures to acromelic acids, and examined their effect on the allodynia-inducing activity of acromelic acids. As a result, some of compounds sharing a definite structure in common were surprisingly found to exhibit an inhibitory activity against acromelic acid-induced allodynia. These findings resulted in the present invention.

Thus, a pyrrolidine analogue according to the first aspect of the present invention is a compound represented by the general formula (I), wherein HOOC-φ represents an aromatic substituent having at least one carboxy group attached to the benzene ring, or a salt or ester of the compound.

[Chemical Formula 3]

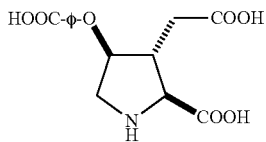
(I)

The pyrrolidine analogue according to the first aspect of the present invention has a pyrrolidine framework similar to acromelic acids, but is characterized by a substituent at the 4-position on the pyrrolidine ring disposed in the cis-configuration relative to the carboxy group at the 2-position. It is further required that at the 4-position an aromatic substituent is attached via an oxygen atom, having at least one carboxy group attached to the benzene ring. According to the result of tests performed by the inventors, the pyrrolidine analogues having such a structure exhibit, when co-administered with an acromelic acid to rats, an inhibitory activity against the induction of allodynia by acromelic acid. Thus, the pyrrolidine analogues can be expected to provide molecular probes which serve in elucidating receptor function involved in neuropathic pain, as well as therapeutic agents for neuropathic pain or development seeds therefor.

While HOOC-φ represents that at least one carboxy group is required to be attached to the benzene ring, an additional substituent (for example, carboxy group, nitro group, amino group, acylamino group, cyano group, halogen, alkyl group, hydroxy group, alkoxy group, amide group, or alkanoyl group, and the like) can be bonded thereto.

The pyrrolidine analogue according to the first aspect of the present invention can be produced by the method comprising the following steps of:

performing the step of nucleophilic substitution by subjecting a pyrrolidine derivative represented by the general formula (1), wherein $R^1$ represents a protective group for amino group, $COOR^2$ and $COOR^3$ represent an ester group; and a benzene derivative represented by the general formula (2), wherein X represents a substituent that can be replaced through aromatic nucleophilic substitution, and at least one cyano group is bonded to the ortho- or para-position relative to X, or a benzene derivative represented by the general formula (2'), wherein X represents a substituent that can be replaced through aromatic nucleophilic substitution, Y represents an electron-withdrawing group bonded to the ortho- or para-position relative to X, Y' represents a substitutent that can be transformed to carboxy group and does not inhibit aromatic nucleophilic substitution and can be at any permissible position on the benzene ring, and Y' being dispensable when Y is a cyano group, or alternatively a derivative of these benzene derivatives wherein the benzene ring has other substituent attached thereto which does not inhibit aromatic nucleophilic substitution; to aromatic nucleophilic substitution under basic condition, and performing the step of deprotection by hydrolyzing the ester group and cyano group after the step of nucleophilic substitution, and deprotecting $R^1$.

[Chemical Formula 4]

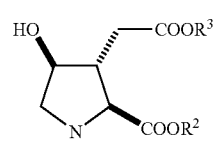
(1)

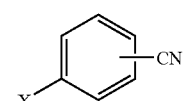
(2)

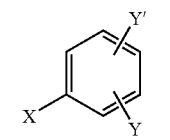
(2')

According to this producing method, the pyrrolidine analogue according to the first aspect of the invention can be readily and massively produced from commercially available trans-4-hydroxy-L-proline as a starting material.

For example, pyrrolidine derivative (4) which exhibits an inhibitory action on allodynia-induction can be obtained from the pyrrolidine derivative represented by the general formula (1) and the benzene derivative represented by the general formula (2) or (2') through reaction scheme below. In the structure, X can be any leaving group such as nitro group or halogen. Y can be, for example, nitro or cyano group, and Y' can be, for example, cyano, alkoxycarbonyl, alkylcarbamoyl group or the like, but when Y is any substituent capable of converting into carboxy group, such as cyano group, Y' may be, for example, hydrogen, alkyl group, halogen, alkanoyl group, carboxamide group, alkoxy group, nitro group or the like. Z, in the compound (4) in the reaction scheme, can be Y and Y' above, and any substituent which can be derivatized therefrom, such as carboxy group, carboxamide group, alkylcarbamoyl group, amino group, acylamino group, halogen, alkyl group, hydroxy group, alkoxy group, alkanoyl group, or nitro group. $R^1$, a protective group for amino group, can be, for example, acetyl, benzoyl, tert-butoxycarbonyl, or benzyloxycarbonyl group.

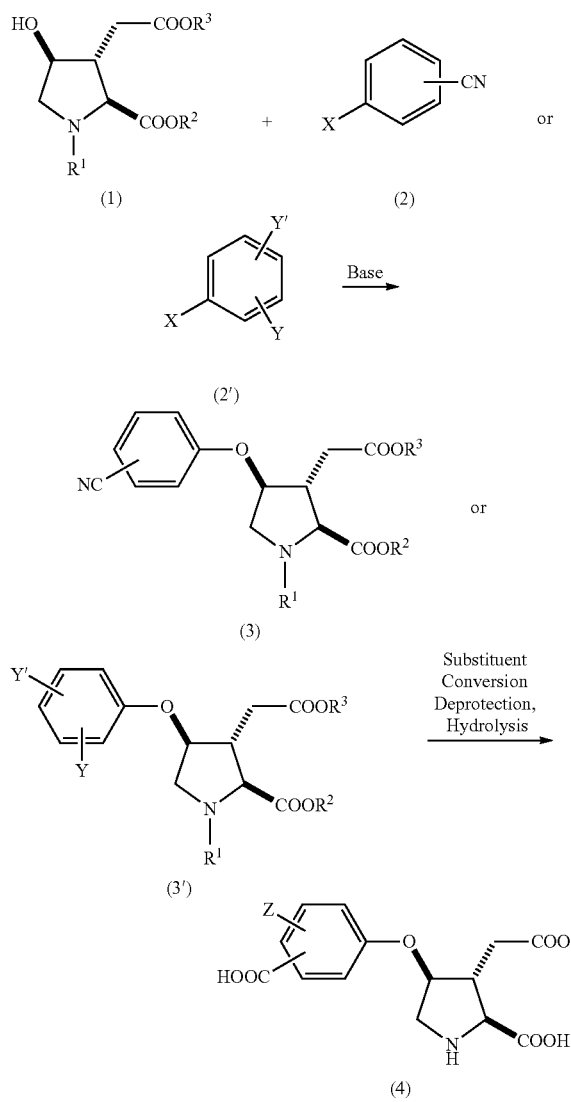

Instead of the benzene derivative (2) and benzene derivative (2') above, any other derivative that has an additional substituent attached to its benzene ring can be used, thus providing a wide variation of possible compounds.

Alternatively, the pyrrolidine analogue according to the first aspect of the invention can also be produced by the following steps of:

performing the step of Mitsunobu reaction by bringing a pyrrolidine derivative represented by the general formula (5), wherein $R^1$ represents a protective group for amino group, $COOR^2$ and $COOR^3$ represent an ester group; and a phenol derivative represented by the general formula (6), wherein R' represents any substituent which is capable of converting into carboxy group and does not inhibit Mitsunobu reaction, for example, alkoxycarbonyl, aryloxycarbonyl, cyano, carboxamide, alkylcarbamoyl group or the like, or the phenol derivative with any other substituent Z' attached on the benzene ring, which may be hydrogen, alkoxycarbonyl group, nitro group, amino group, acylamino group, cyano group, carbamoyl group, halogen, alkyl group, hydroxy group, alkoxy group, amide group, alkanoyl group or the like, that does not inhibit Mitsunobu reaction; into Mitsunobu reaction to convert them into an ether derivative with inversion of stereochemistry, and performing the step of deprotection by hydrolyzing the ester group of the ether derivative, deprotecting $R^1$ and converting the substituent R' into carboxy group.

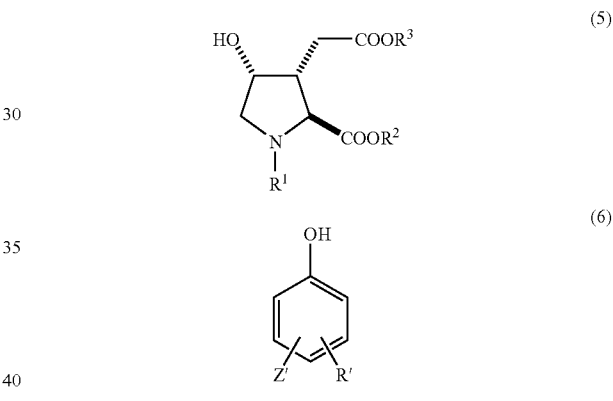

Also by this method, the proline analogue according to the first aspect of the invention can be readily and massively produced from commercially available trans-4-hydroxy-L-proline as a starting material.

The producing method can be expressed by the following reaction scheme. A substituent Z" of product (8) in the reaction scheme can be either Z' above, or any substituent that can be derived therefrom, such as carboxy group, amino group, acylamino group, cyano group, halogen, alkyl group, hydroxy group, alkoxy group, amide group, or alkanoyl group.

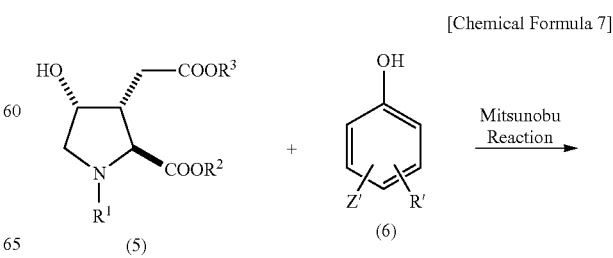

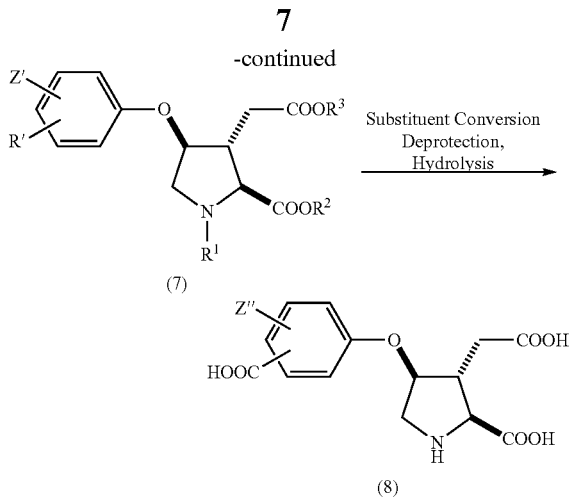

A pyrrolidine analogue according to the second aspect of the invention is a compound represented by the general formula (II), wherein HOOC-φ represents any aromatic substituent except p-carboxyphenyl group, having at least one carboxy group attached to the benzene ring, or a salt or ester of the compound.

[Chemical Formula 8]

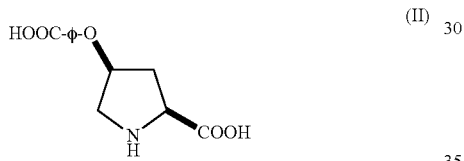

The pyrrolidine analogue according to the second aspect of the invention has a similar framework to that of the pyrrolidine analogue according to the first aspect of the invention, but is characterized by an absence of carboxymethyl group at the 3-position. Moreover, the carbon at the 4-position is required to have an aromatic substituent attached thereto via an oxygen atom, which has at least one carboxy group bonded to the benzene ring. A substituent bonded to φ can be, other than the one carboxy group shown, carboxy group, nitro group, amino group, acylamino group, cyano group, halogen, alky group, hydroxy group, alkoxy group, amide group, alkanoyl group or the like.

Since the pyrrolidine analogue having such a structure exhibits an inhibitory activity on allodynia induction according to the test result obtained by the inventors, it can be used as an agent for preventing neuropathic pain. In addition, those pyrrolidine analogues which have 4-carboxyphenyl group as HOOC-φ in the general formula (II) above can also be used as an agent for preventing neuropathic pain.

The pyrrolidine analogue according to the second aspect of the invention can be produced by the following steps of:

performing the step of nucleophilic substitution by subjecting a pyrrolidine derivative represented by the general formula (9), wherein $R^1$ represents a protective group for amino group, and $COOR^2$ represents an ester group; and a benzene derivative represented by the general formula (2), wherein X represents a substituent that cab be replaced through aromatic nucleophilic substitution, and at least one cyano group is bonded to the ortho- or para-position relative to X, or a benzene derivative represented by the general formula (2'), wherein X represents a substituent that cab be replaced through aromatic nucleophilic substitution, Y represents an electron-withdrawing group bonded to the ortho- or para-position relative to X, Y' represents a substitutent that can be transformed to carboxy group and does not inhibit aromatic nucleophilic substitution, and can be at any permissible position on the benzene ring, and Y' being dispensable when Y is a cyano group, or alternatively a derivative of these benzene derivatives wherein the benzene ring has other substituent attached thereto which does not inhibit aromatic nucleophilic substitution; to aromatic nucleophilic substitution under basic condition, and performing the step of deprotection by hydrolyzing the ester group and cyano group after the step of nucleophilic substitution, and deprotecting $R^1$.

[Chemical formula 9]

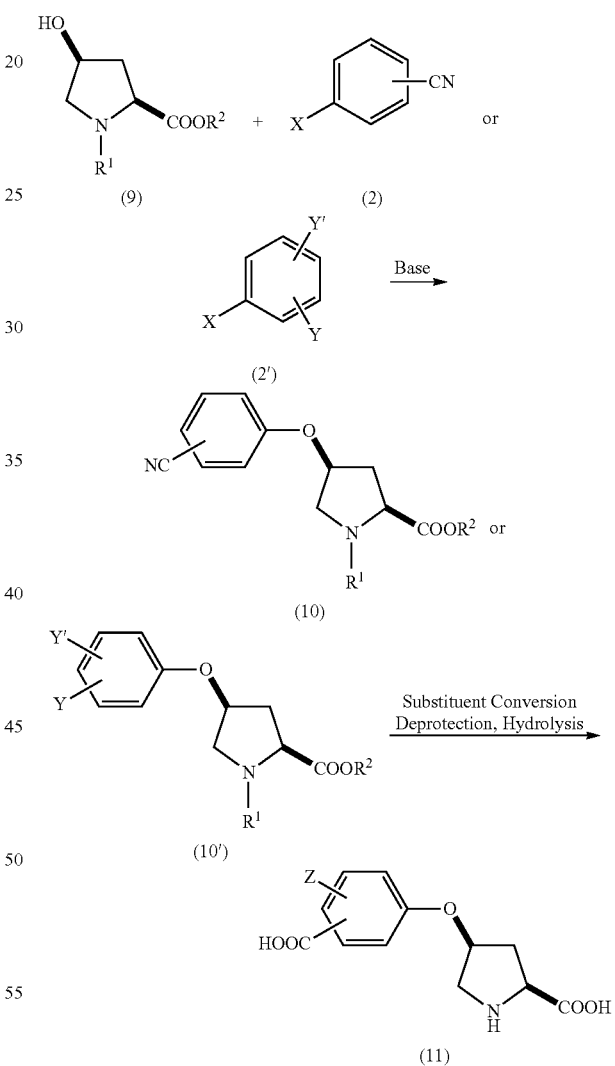

Alternatively, the pyrrolidine analogue according to the second aspect of the invention can also be produced as in the reaction scheme shown below by the following steps of:

performing the step of Mitsunobu reaction by bringing pyrrolidine derivative (12) and a phenol derivative represented by the general formula (6), wherein R' represents any substituent which is capable of converting into carboxy group and does not inhibit Mitsunobu reaction, for example, alkoxycarbonyl, aryloxycarbonyl, cyano, carboxamide, alkylcarbamoyl group or the like, or the phenol derivative with any other substituent Z' attached on the benzene ring which may be hydrogen, alkoxycarbonyl group, nitro group, amino group, acylamino group, cyano group, carbamoyl group, halogen, alkyl group, hydroxy group, alkoxy group, amide group, alkanoyl group, or the like, that does not inhibit Mitsunobu reaction, into Mitsunobu reaction to bind them through ether bond with inversion of stereochemistry of the carbon at the 4-position, and performing the step of deprotection, hydrolysis and generation of carboxy group. A substituent Z" of the pyrrolidine analogue (14) in the reaction scheme can be either Z' above, or any substituent that can be derivatized therefrom, such as carboxy group, amino group, acylamino group, cyano group, halogen, alkyl group, hydroxy group, alkoxy group, amide group, or alkanoyl group.

[Chemical Formula 10]

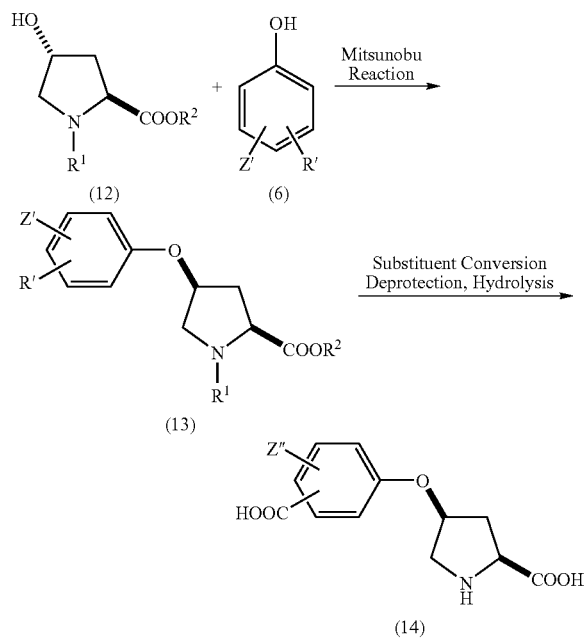

A pyrrolidine analogue according to the third aspect of the invention is a compound represented by the general formula (III), wherein φ represents any aromatic substituent not having a carboxy group, except phenyl and 2-methoxyphenyl groups, or any salt or ester of the compound.

[Chemical Formula 11]

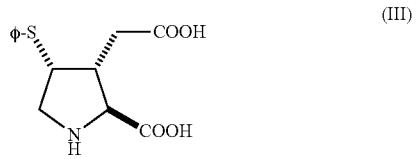

(III)

The pyrrolidine analogue according to the third aspect of the invention has a similar structure to that of the pyrrolidine analogue according to the first aspect of the invention, but the oxygen atom that is bonded to the carbon at the 4-position on the pyrrolidine ring is replaced with sulfur, and with the sterically inverted configuration at the 4-position. Moreover, the aromatic substituent bonded to the sulfur does not have carboxylic acid, different from the pyrrolidine analogue according to the first aspect of the invention. According to the result of the test performed by the inventors, since the pyrrolidine analogues having such a structure also exhibit an inhibitory activity on allodynia induction, they can be used as agents for preventing neuropathic pain. Herein, φ in the formula represents any aromatic substituent with hydrogen or other substituent such as nitro group, amino group, acylamino group, cyano group, halogen, alkyl group, hydroxy group, alkoxy group, amide group, or alkanoyl group except carboxy group. Such a pyrrolidine analogue as that has phenyl or 2-methoxyphenyl group as φ in the general formula (III) above can also be used as an agent for preventing neuropathic pain.

The pyrrolidine analogue according to the third aspect of the invention can be produced by the following steps of:

coupling a pyrrolidine derivative represented by the general formula (I), wherein $R^1$ represents a protective group for amino group, and $COOR^2$ and $COOR^3$ represent an ester group, and diphenyl disulfide or diphenyl disulfide derivative (15), wherein R" may be, for example, hydrogen, nitro group, amino group, acylamino group, cyano group, halogen, alkyl group, hydroxy group, alkoxy group, amide group, alkanoyl group, carbamoyl group, sulfony group, sulfanyl group or the like, with each other under the presence of phosphine reagent to form a thioether derivative with inversion of configuration at the 4-position, and performing deprotection by hydrolyzing the ester group of the thioether derivative and deprotecting $R^1$.

[Chemical Formula 12]

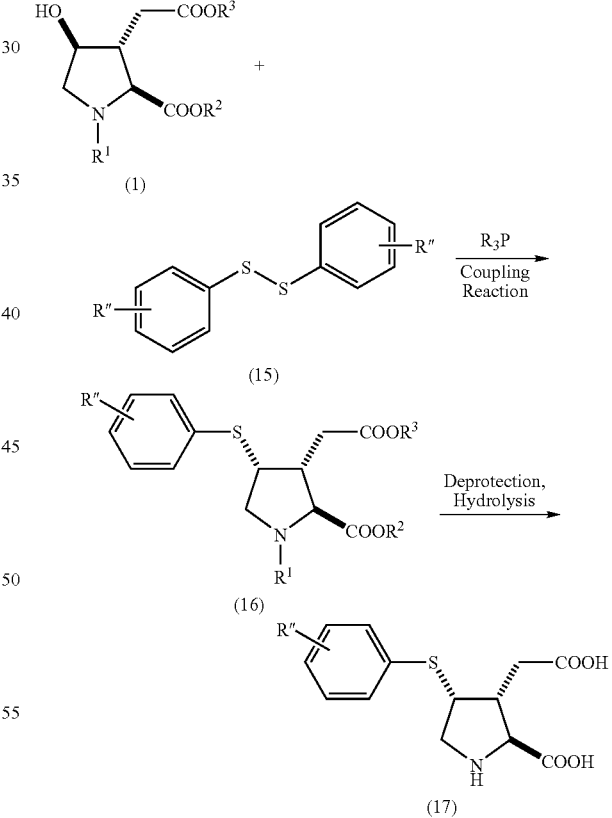

Alternatively, it can be produced by the following steps of:

coupling a pyrrolidine derivative represented by the general formula (I), wherein $R^1$ represents a protective group for amino group, and $COOR^2$ and $COOR^3$ represent an ester group, and thiophenol or substituted thiophenol (18), wherein R" may be, for example, hydrogen, nitro group, amino group, acylamino group, cyano group, halogen, alkyl group, hydroxy group, alkoxy group, amide group, alkanoyl group, carbamoyl group, sulfonyl group, sulfanyl group or the like, with each other through Mitsunobu reaction to form a thioether derivative with inversion of configuration at the 4-position; and performing the similar deprotection and hydrolysis steps.

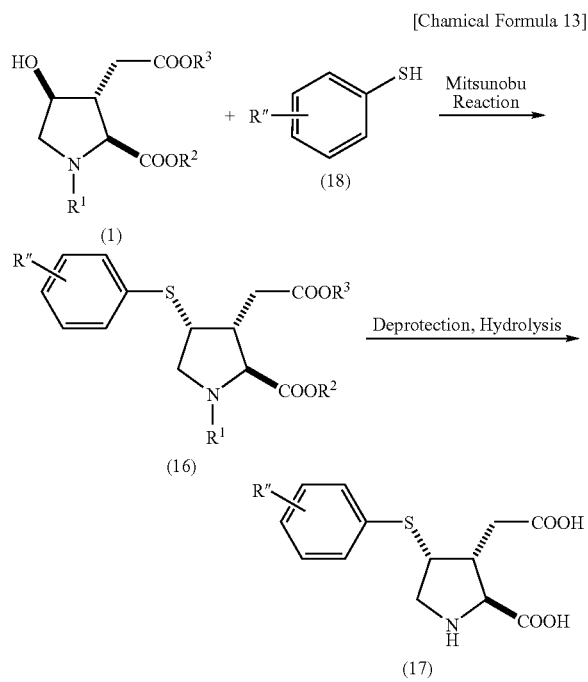

Thus, the proline analogue according to the third aspect of the invention can be produced readily and massively from commercially available trans-4-hydroxy-L-proline as a starting material by using this producing method as well. In addition, a wide variation of the compound can be synthesized by using different diphenyl disulfide derivatives or substituted thiophenols. Moreover, the substituent on the benzene ring can be converted after the coupling reaction or Mitsunobu reaction so as to yield any derivative. $R^1$, a protective group for amino group, may be, for example, acetyl, benzoyl, tert-butoxycarbonyl, benzyloxycarbonyl group or the like. The phosphine reagent may be, for example, trialkylphosphine, triphenylphosphine, or the like. The diphenyl disulfide derivative and the substituted thiophenol may have any substituent as long as they do not inhibit coupling reaction.

A pyrrolidine analogue according to the fourth aspect of the invention is a compound represented by the general formula (IV), wherein φ represents an aromatic substituent, or a salt or ester of the compound.

[Chemical Formula 14]

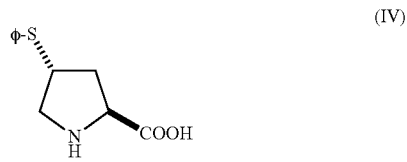

The pyrrolidine analogue according to the fourth aspect of the invention has a similar structure to that of the pyrrolidine analogue according to the third aspect of the invention, but with no carboxymethyl group attached to the carbon at the 3-position on the pyrrolidine ring. In addition, the carbon at the 4-position is required to have an aromatic substitutent bonded thereto via a sulfur atom. A substituent bonded to φ may be, for example, nitro group, amino group, acylamino group, cyano group, halogen, hydroxy group, alkoxy group, alkyl group, amide group, alkanoyl group, carbamoyl group, sulfonyl group, sulfanyl group or the like.

Since the pyrrolidine analogues having such a structure exhibit, according to the test result obtained by the inventors, a strong inhibitory activity on allodynia induction, they can be used as agents for preventing neuropathic pain.

The pyrrolidine analogue according to the fourth aspect of the invention can be produced by the following steps of:

coupling a pyrrolidine derivative represented by the general formula (9), wherein $R^1$ represents a protective group for amino group, and $COOR^2$ represents an ester group, and diphenyl disulfide or diphenyl disulfide derivative (15), wherein R" may be, for example, hydrogen, nitro group, amino group, acylamino group, cyano group, halogen, alkyl group, hydroxy group, alkoxy group, amide group, alkanoyl group, carbamoyl group, sulfonyl group, sulfanyl group or the like, with each other under the presence of phosphine reagent to form a thioether derivative with inversion of configuration at the 4-position, and performing deprotection by hydrolyzing the ester group of the thioether derivative and deprotecting $R^1$.

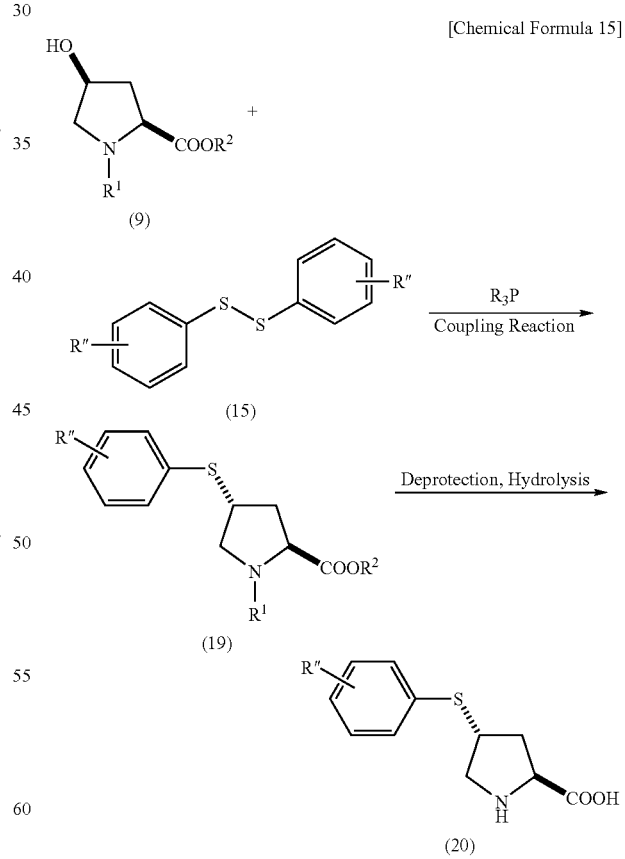

Alternatively, it can be produced by the following steps of:
coupling a pyrrolidine derivative represented by the general formula (9), wherein $R^1$ represents a protective group for amino group, and $COOR^2$ represents an ester group, and thiophenol or substituted thiophenol (18), wherein R" may be, for example, hydrogen, nitro group, amino group, acylamino group, cyano group, halogen group, alkyl group, hydroxy group, alkoxy, group amide group, alkanoyl group, carbamoyl group, sulfonyl group, sulfanyl group or the like, with each other through Mitsunobu reaction to form a thioether derivative with inversion of configuration at the 4-position; and performing the similar deprotection and hydrolysis steps.

[Chemical Formula 16]

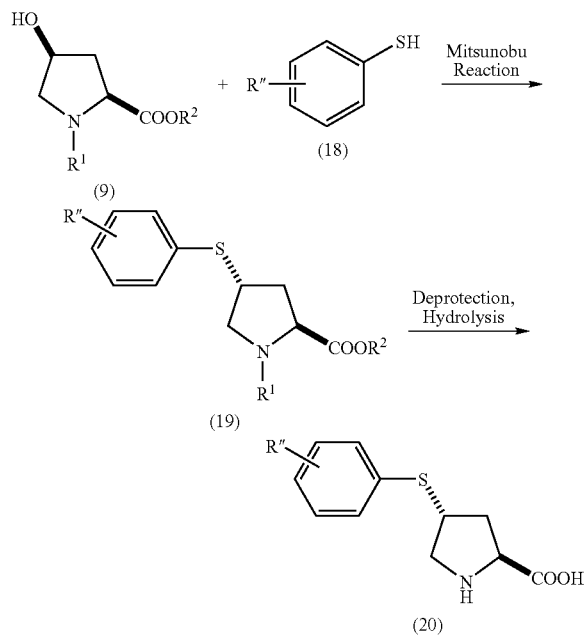

Thus, the proline analogue according to the fourth aspect of the invention can be produced readily and massively from commercially available trans-4-hydroxy-L-proline as a starting material by using this producing method as well. In addition, a wide variation of the compound can be synthesized by using different diphenyl disulfide derivatives and/or substituted thiophenols. Moreover, the substituent on the benzene ring can be converted after the coupling reaction or Mitsunobu reaction so as to yield any derivative.

$R^1$, a protective group for amino group, may be, for example, acetyl, benzoyl, tert-butoxycarbonyl, benzyloxycarbonyl group or the like. The phosphine reagent may be, for example, trialkylphosphine, triphenylphosphine, or the like. The diphenyldisulfide derivative and substituted thiophenol may have any substituent as long as they do not inhibit coupling reaction.

The pyrrolidine analogues and agents for preventing neuropathic pain according to the present invention can have any functional group with a molecular probe function on the benzene ring, such that the compounds may facilitate the functional analysis of targeted receptors. Such a substituent functioning as a molecular probe can be readily introduced onto the benzene ring, thereby facilitating mass synthesis. Possible substituents functioning as a molecular probe are fluorescent substituents, biotin group, substituents capable of photo-affinity labeling, and substituents labeled with $^{11}C$ or any other isotope, and the like.

BEST MODE FOR CARRYING OUT THE INVENTION

Figure 1:
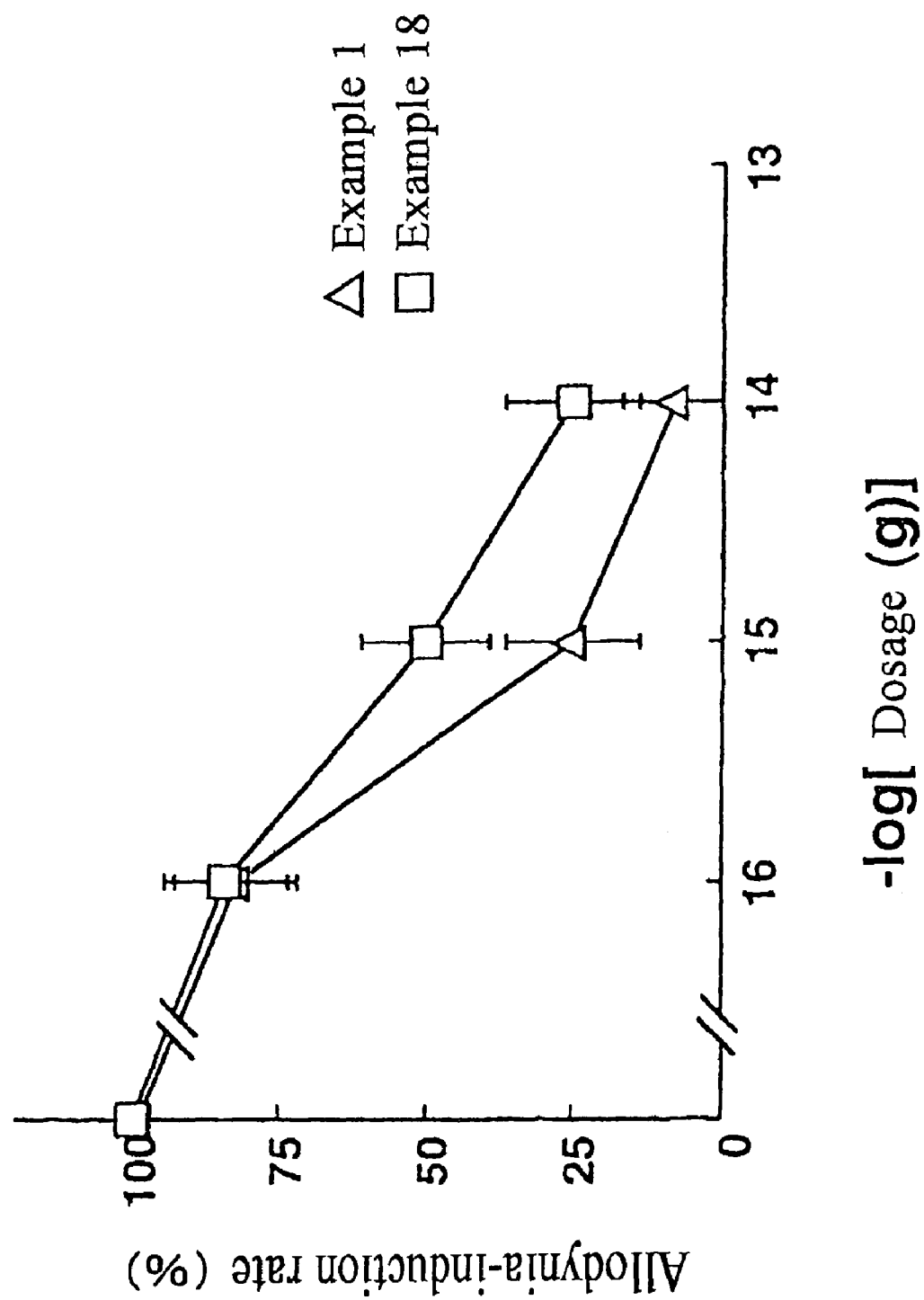
FIG. 1 shows the relationship between the percentage of allodynia induction and dosage of the pyrrolidine analogues of Examples 1 and 18.

The pyrrolidine analogue according to the present invention encompasses not only free carboxylic acid and free amines but also salts and ester thereof. In addition, any element constituting the same may include any isotope.

Exemplary isotopes of hydrogen, carbon, nitrogen, oxygen, phosphorus, sulfur, and chlorine are $^2H$, $^3H$, $^{13}C$, $^{14}C$, $^{15}N$, $^{17}O$, $^{18}O$, $^{31}P$, $^{32}P$, $^{35}S$, $^{18}F$, $^{36}Cl$ and the like. The pyrrolidine analogues according to the present invention, labeled with any one of these isotopes, are extremely useful in studying how drugs and substrates are distributed in cells and living tissues. Moreover, when any isotope that emits positron (such as $^{11}C$, $^{18}F$, $^{15}O$ and $^{13}N$) is used, positron emission computed tomography (PET) can be performed, thus providing further usefulness in studying their kinetic analysis in vivo, substrate's receptor occupancy, and the like.

Generally, the pyrrolidine analogues labeled with any isotopes according to the present invention can be produced by using reagents labeled with any isotopes by any conventional technique known by those who skilled in the art or by any method similar to those described in the Examples.

Since the pyrrolidine analogues according to the present invention have a structure of amino acids which are amphoteric compounds, they can be salts with inorganic acids, organic acids or any base. As an acidic salt, they can be, for example, hydrochloride, hydrobromate, hydroiodate, sulfate, bisulfate, nitrate, phosphate, hydrophosphate, acetate, fumarate, bicarbonate, carbonate, maleate, citrate, succinate, and the like.

Basic salts include salts with sodium, potassium, aluminum, calcium, magnesium, zinc, alkylamine, and amines. They can be amphoteric ions.

Preferred salts as the pyrrolidine analogues according to the invention are hydrochlorides. For suitable salts, see Stahl and Wermuth, Handbook of Pharmaceutical Salts:Properties, Selection, and Use, Wiley-VCH, Weinheim, Germany(2002).

When the pyrrolidine analogues according to the present invention are used as pharmaceuticals for oral administration, it may be preferable that they are salts having quaternary ammonium ion. As described in the Patent document 1 and the Patent document 2, absorption rate of drugs administered orally is known to be enhanced when the drugs are produced in the form of "soft" quarternary ammonium salts. Amongst quaternary ammonium salts, "soft" ones are preferable since "soft" quaternary ammonium salts, different from common quaternary ammonium salts (such as $R-N^+(CH_3)_3$), are hydrolyzed to enable to release active agents. In addition, "soft" quaternary ammonium salts are known to have a high intestinal absorption rate of drugs. This is possibly due to a potential surfactant-like property of "soft" quaternary ammonium salts, enabling them to form a micelle and an unionized ion pair with bile acids and to effectively penetrate intestinal epithelium. Upon being absorbed, pro-drugs are rapidly hydrolyzed to release active parent drugs.

The pyrrolidine analogues according to the present invention in the form of salts can be readily produced by combining them with any acid or base. Resultant salts may be collected by precipitation in solution and filtration, or evaporation of solvent. Alternatively, their salts may be solvated with, for example, water, or provided as composite salts.

The pyrrolidine analogues according to the present invention comprise pro-drugs and those which are labeled with any isotope. The term "pro-drugs" used herein refers to those drugs which in themselves have little or no pharmacological activity, but, when administered into or onto body, are cleaved by hydrolysis or oxidatively metabolized to be converted into compounds having a desired activity. For further details of use of pro-drugs, see 'Pro-drugs as Novel Delivery Systems, Vol. 14, ACS Symposium Series (T Higuchi and W Stella)' and 'Bioreversible Carriers in Drug Design', Pergamon Press, 1987(ed. E B Roche, American Pharmaceutical Association)".

As an exemplary method of producing pro-drugs, any functional groups may be replaced with a given moiety known by those who skilled in the art, such as "pro-moieties" described in "Design of ester pro-drug stoenhance oral absorption of poorly permeable compounds", K. Beaumont et al, Current Drug Metabolism, 2003 and "Design of Pro-drugs", H. Bundgaard(Elsevier)1985. Any intermediate obtained during coupling step in the producing method of the pyrrolidine analogues according to the present invention, or a compound derived therefrom by deprotecting a portion of protective group on the intermediate may be used as a pro-drug.

Exemplary pro-drugs are esters of carboxy group (—COOH), and carboxamide (for example, —CONH$_2$, —CONHR or —CONRR', R and R', wherein R and R' are each independent (C1-C6)alkyls).

In addition, aminoacyl-glycolic acids and ester lactate are known to be pro-drugs of amino acids (Wermuth C. G., Chemistry and Industry, 1980:433-435). Carboxy group on amino acids can be esterified by known means. Pro-drugs are known in the art (Palomino E., Drugs of the Future, 1990;15 (4):361-368).

Other exemplary pro-drugs include those which are described in the Patent documents 1 and 2.

An example of the present invention will further described in detail below.

<Synthesis (1) of Substituted Phenoxypyrrolidine Analogue (I)>

Following the reaction scheme below, substituted phenoxypyrrolidine analueog (4) (this compound is encompassed in the scope of the general formula (I) described above) was synthesized.

[Chemical Formula 17]

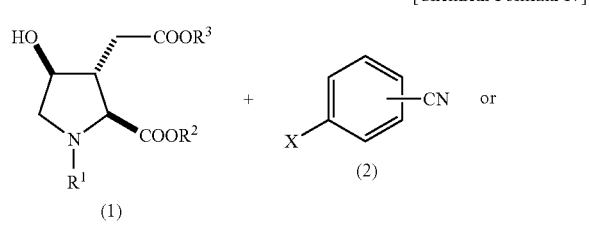

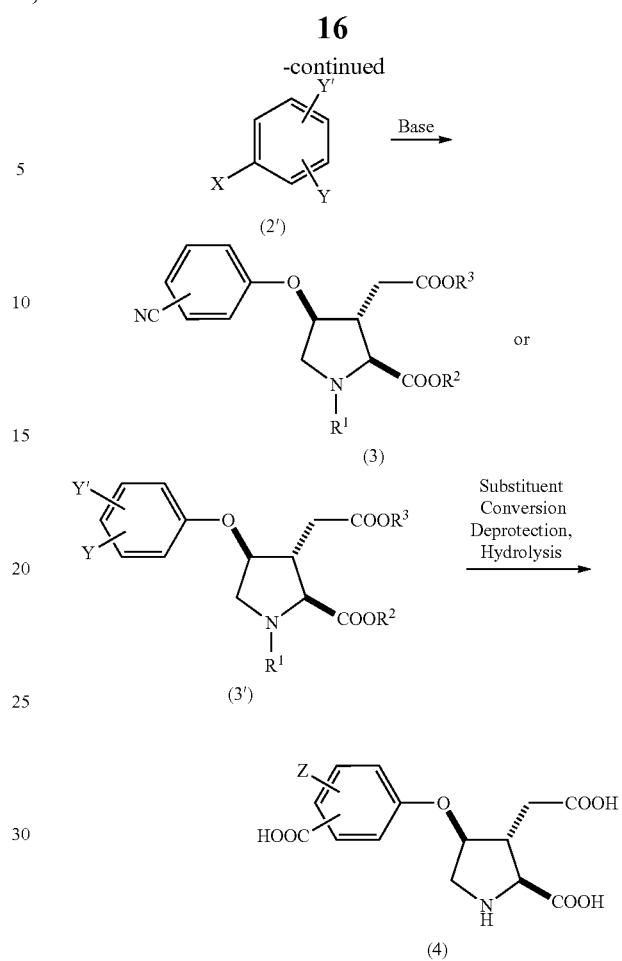

(Nucleophilic Substitution Step)

In the nucleophilic substitution step, 4-hydroxyproline derivative (1) synthesized according to the method described in the literature (Baldwin, J. E. et al. Tetrahedron, 1997, 53, 5233; Furuta, K. et al. Tetrahedron Lett., 2004, 45, 3933) is reacted with sodium hydride, and then a benzonitrile derivative, commercially available or synthesized by the already known methods in the literature, in DMF solution to afford the above substitution product (3) or (3').

(Deprotection Step)

In the deprotection step, to the substitution product (3) or (3') synthesized in the above nucleophilic substitution step, hydrochloric acid is added, and the mixture is refluxed with heating to deprotect R$^1$ and hydrolyze ester and cyano groups, thus yielding substituted phenoxypyrrolidine analogue (4). If a substitutent Y is a cyano group, the Y is also converted into a carboxy group.

The synthesis of the above-mentioned substituted phenoxypyrrolidine analogue (4) will be described in further detail, referring to Examples 1 through 4 wherein the reaction step is specified.

EXAMPLE 1

In Example 1, (2S,3R,4S)-3-carboxymethyl-4-(4-carboxyphenoxy)-pyrrolidine-2-carboxylic acid (Ia) was synthesized according to the method shown below.

1) Nucleophilic Substitution Step

[Chemical Formula 18]

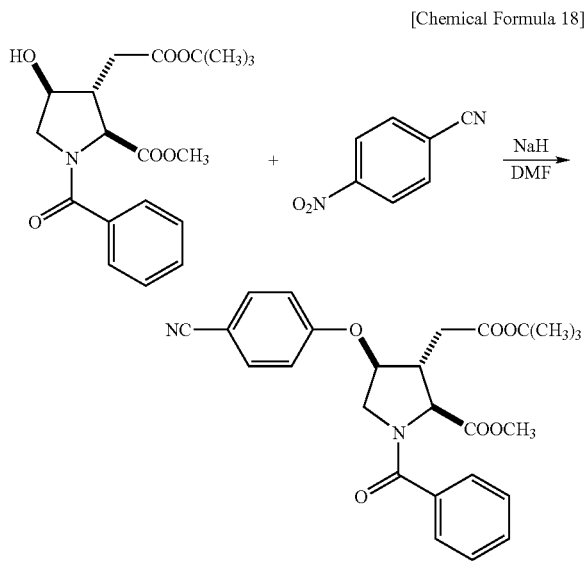

In the nucleophilic substitution step, aromatic nucleophilic substitution shown above was performed. Specifically, a solution of methyl(2S,3R,4S)-1-benzoyl-3-(tert-butoxycarbonyl-methyl-4-hydroxypyrrolidine-2-carboxylate (40 mg, 110 μmol) in DMF (170 μL) was added dropwise to a suspension of N,N-dimethylformamide (DMF, 220 μL) containing sodium hydride (60% dispersion, 4.4 mg, 110 μmol) cooled at −35° C. under the argon atmosphere, followed by stirring for 15 minutes. Then, 4-nitrobenzonitrile (24.4 mg, 165 μmol) dissolved in DMF (260 μL) was added, and the reaction solution was stirred at −35° C. for 24 hours. The reaction mixture was poured into an aqueous solution of potassium hydrogen sulfate (5%), and the resultant product was extracted with ether. The organic phase was dried over anhydrous sodium sulfate, filtered, and concentrated in vacuo, and the resultant residue was purified by column chromatography (silica gel 60, hexane/ethyl acetate=6/5) to obtain (2S,3R,4S)-1-benzoyl-3-(tert-butoxycarbonylmethyl)-4-(4-cyanophenoxy)pyrrolidine-2-methyl-carboxylate (41.6 mg, 81%). TLC and $^1$H NMR data are shown below.

TLC: $R_f$=0.56 (silica gel, hexane/ethyl acetate=1/2)

$^1$H NMR (400 MHz, CDCl3): (two rotamers) δ(ppm) 1.44 and 1.47 (s, 9H), 2.41 (d, J=8 Hz) and 2.45 (dd, J=8 and 16.4 Hz) and 2.62 (dd, J=5.8 and 16.4 Hz) (2H), 3.07-3.15 (complex) and 3.15-3.23 (br t, J=7.6 Hz) (1H), 3.64 and 3.77 (s, 3H), 3.8 (d, J=4 Hz), 3.90 (d, J=14 Hz), 3.93 (dd, J=5.6 and 12 Hz), 4.28 (dd, J=5.6 and 14 Hz), 4.32 (br s), 4.72 (d, J=4.4 Hz), 4.83-4.89 (m, 1H), 6.95 (d, J=8 Hz, 2H), 7.35-7.5 (complex, 4H), 7.55-7.64 (complex, 3H).

2) Deprotection Step

[Chemical Formula 19]

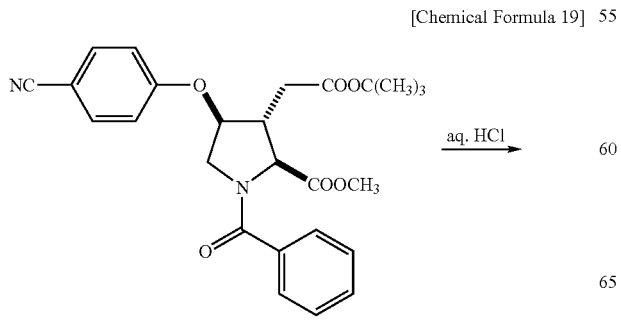

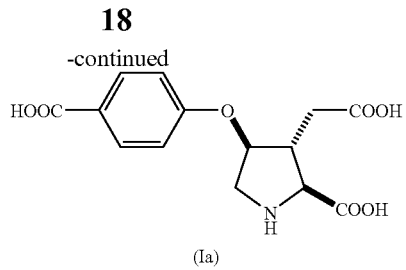

Subsequently, the reaction above was performed as the deprotection step. Specifically, to methyl(2S,3R,4S)-1-benzoyl-3-(tert-butoxycarbonylmethyl)-4-(4-cyanophenoxy) pyrrolidine-2-carboxylate (25.0 mg, 53.8 μmol) obtained in the nucleophilic substitution step was added 6M hydrochloric acid (0.8 mL), and the mixture was refluxed with heating at 110° C. for 20 hours. The reaction solution, after cooled down to room temperature, was washed with chloroform, and lyophilized, and the resultant residue was purified by ion exchange chromatography (Dowex 50WX8) to yield the compound of interest (Ia) (12.4 mg, 75%). $^1$H NMR data of this compound is shown below.

$^1$H NMR (400 MHz, D$_2$O): δ (ppm) 2.22 (dd, J=10 and 15.6 Hz, 1H), 2.39 (dd, J=6 and 15.6 Hz, 1H), 2.98-3.06 (br, 1H), 3.58 (br s, 1H), 3.85 (d, J=2.4 Hz, 1H), 4.89 (br s, 1H), 6.83 (d, J=8.4 Hz, 2H), 7.68 (d, J=8.4 Hz, 2H).

EXAMPLE 2

In Example 2, by using 4-fluorobenzonitrile instead of 4-nitrobenzonitrile in the nucleophilic substitution step of Example 1, methyl(2S,3R,4S)-1-benzoyl-3-(tert-butoxycarbonylmethyl)-4-(4-cyanophenoxy)pyrrolidine-2-carboxylate was synthesized.

Specifically, a solution of methyl(2 S,3R,4S)-1-benzoyl-3-(tert-butoxycarbonylmethyl)-4-hydroxypyrrolidine-2-carboxylate (16.1 mg, 44.3 μmol) in DMF (140 μL) was added dropwise to a suspension of N,N-dimethylformamide (DMF, 90 μL) and sodium hydride (60% dispersion, 1.8 mg, 45 μmol) cooled at −35° C. under the argon atmosphere, and stirred for 15 minutes. Then, 4-fluorobenzonitrile (7 mg, 57.8 μmol) dissolved in DMF (110 μL) was added, and the reaction solution was stirred at −35° C. for 14 hours. The reaction mixture was poured into aqueous potassium hydrogen sulfate (5%), and the product was extracted with ether. The organic phase was dried over anhydrous sodium sulfate, filtered, and concentrated in vacuo, and the resultant residue was purified by thin layer chromatography (silica gel 60, 0.5 mm, hexane/ethyl acetate=1/1, 2 developments) to obtain the compound of interest (3.6 mg, 17%). $^1$H NMR data of this compound is shown below.

$^1$H NMR (400 MHz, CDCl$_3$): (two rotamers) δ (ppm) 1.44 and 1.47 (s, 9H), 2.41 (d, J=8 Hz) and 2.45 (dd, J=8 and 16.4 Hz) and 2.62 (dd, J=6 and 16.4 Hz) (2H), 3.07-3.15 (complex) and 3.15-3.23 (br t, J=7.6 Hz) (1H), 3.64 and 3.77 (s, 3H), 3.8 (d, J=4 Hz), 3.90 (d, J=14 Hz), 3.93 (dd, J=5.6 and 12 Hz), 4.28 (dd, J=5.2 and 14 Hz), 4.32 (br s), 4.72 (d, J=4.4 Hz), 4.83-4.89 (m), 6.95 (d, J=8 Hz, 2H), 7.35-7.5 (complex, 4H), 7.55-7.64 (complex, 3H).

This compound is deprotected as in Example 1 to convert the cyano and ester groups into carboxylic acid, and the protecting group attached on the nitrogen is removed to form an amino group, thus yielding the compound of interest.

EXAMPLE 3

In Example 3, by using a different species of protecting group on the pyrrolidine compound from that was used in the Example 1, and through the reaction with 4-nitrobenzonitrile, methyl(2 S,3R,4S)-1-(tert-butoxycarbonyl)-4-(4-cyanophenoxy)-3-(methoxycarbonylmethyl)pyrrolidine-2-carboxylate was synthesized.

Specifically, a solution of methyl(2S,3R,4S)-1-(tert-butoxycarbonyl)-4-hydroxy-3-(methoxycarbonylmethyl)pyrrolidine-2-carboxylate(60 mg, 189 μmol) in DMF (300 μL) was added dropwise to a suspension of N,N-dimethylformamide (DMF, 380 μL) and sodium hydride (60% dispersion, 7.6 mg, 190 μmol) cooled at −35° C. under the argon atmosphere, and stirred for 30 minutes. Then, 4-nitrobenzonitrile (42.1 mg, 284 μmol) dissolved in DMF (450 μL) was added, and the reaction solution was stirred at −35° C. for 40 hours. The reaction mixture was poured into aqueous potassium hydrogen sulfate (5%), and the product was extracted with ether. The organic phase was dried over anhydrous sodium sulfate, filtered, and concentrated in vacuo, and the resultant residue was purified by thin layer chromatography (silica gel 60, 0.5 mm, hexane/ethyl acetate=3/2, 4 developments) to obtain the compound of interest (47.4 mg, 60%). $^1$H NMR data of this compound is shown below.

$^1$H NMR (400 MHz, CDCl$_3$): (two rotamers) δ (ppm) 1.43 and 1.49 (s, 9H), 2.47 (dd, J=9.2 and 16.8 Hz) and 2.53 (dd, J=8.4 and 16.8 Hz) (1H), 2.63 (dd, J=6.2 and 16.8 Hz) and 2.65 (dd, J=5.4 and 16.8 Hz) (1H), 3.06-3.13 (m, 1H), 3.61-3.68 (br m, 1H), 3.70 and 3.72 and 3.73 (s, 6H) 3.85 (dd, J=5.4 and 12.6 Hz) and 3.93 (dd, J=5.0 and 12.2 Hz) (1H), 4.14 (d, J=3.6 Hz) and 4.27 (d, J=2.4 Hz) (1H), 4.73-4.79 and 4.80-4.85 (m, 1H), 6.95 (d, J=8.8 Hz) and 6.97 (d, J=8.8 Hz) (2H), 7.59 (d, J=8.8 Hz) and 7.60 (d, J=8.8 Hz) (2H).

This compound is deprotected as in Example 1 to convert the cyano and ester groups into carboxy group, and the protecting group attached on the nitrogen is removed, thus yielding the pyrrolidine analogue according to the present invention.

EXAMPLE 4

In Example 4, by using 2-nitrobenzonitrile instead of 4-nitrobenzonitrile used in the nucleophilic substitution step in the Example 1, methyl(2S,3R,4S)-1-benzoyl-3-(tert-butoxycarbonylmethyl)-4-(2-cyanophenoxy)pyrrolidine-2-carboxylate was synthesized. This compound is an isomer that is different from the compound according to Example 1 in respect of the position of carboxylate binding to phenoxy group, and was synthesized as follows.

Specifically, a solution of methyl(2S,3R,4S)-1-benzoyl-3-(tert-butoxycarbonylmethyl)-4-hydroxypyrrolidine-2-carboxylate (40 mg, 110 μmol) in DMF (140 μL) was added dropwise to a suspension of N,N-dimethylformamide (DMF, 500 μL) and sodium hydride (60% dispersion, 4.6 mg, 116 μmol) cooled down to −45° C. under the argon atmosphere, and stirred for 15 minutes. Subsequently, 2-nitrobenzonitrile (18.1 mg, 122 μmol) dissolved in DMF (110 μL) was added, and the reaction solution was stirred at −45° C. for 31 hours. Diluted hydrochloric acid (1M) was poured into the reaction mixture, and the product was extracted with ether. The organic phase was dried over anhydrous sodium sulfate, filtered, and concentrated in vacuo, and the resultant residue was purified by thin layer chromatography (silica gel 60, 0.5 mm, hexane/ethyl acetate=3/2, 3 developments) to obtain the compound of interest (42 mg, 82%). $^1$H NMR data of this compound is shown below.

$^1$H NMR (400 MHz, CDCl$_3$): (two rotamers) δ (ppm) 1.43 and 1.47 (s, 9H), 2.41 (dd, J=8 and 16 Hz) and 2.47 (dd, J=8 and 16 Hz) and 2.48 (dd, J=8 and 16 Hz) and 2.64 (dd, J=8 and 16 Hz), 3.2 (br m) and 3.31 (br t, J=8 Hz) (1H), 3.81 and 3.87 (s, 3H), 3.84-3.99 (complex, 1.5 H), 4.36 (dd, J=4 and 16 Hz, 0.5 H), 4.39 (br, 0.5H), 4.81 (d, J=4 Hz) and 4.86 (d, J=8 Hz) (1H), 4.91-4.97 (br m, 0.5H), 6.98-7.08 (complex, 2H), 7.35-7.62(complex, 7H).

This compound is deprotected as in Example 1 to convert the cyano and ester groups into carboxy group, and the protecting group attached on the nitrogen is removed, thus yielding the pyrrolidine analogue according to the present invention.

<Synthesis (2) of Substituted Phenoxy Pyrrolidine Analogue (I)>

Substituted phenoxy pyrrolidine analogues can also be synthesized, as shown in the reaction scheme below, by using the compound (5) that is a sterically inverted version of 4-hydroxyproline derivative (1) at the 4-position to perform Mitsunobu reaction step with substituted phenol (6), followed by deprotection step. Compound (8) in the scheme is a compound encompassed in the scope of the general formula (I) described above.

[Chemical Formula 20]

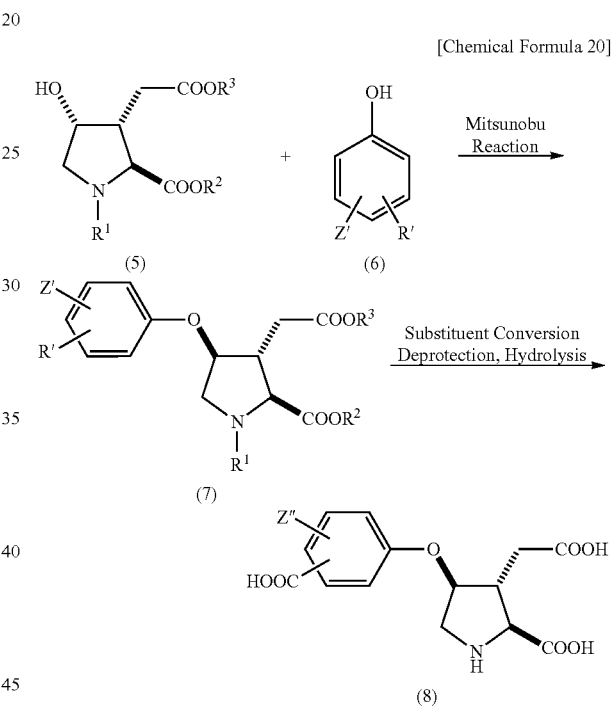

1) Mitsunobu Reaction Step

To THF or DMF solution of the above compound (5) prepared from the compound (1) used as a starting material in the Examples 1 through 4, triphenylphosphine, and phenol derivative (6) commercially available or synthesized by any known method, dialkyl azodicarboxylate is added dropwise at room temperature over several minutes to one hour, followed by stirring at room temperature to 50° C. to yield the compound (7). Alternatively, to a solution of phenol derivative (6) and triphenylphosphine in toluene heated at 60° C. to 90° C., a solution of the compound (5) and diisopropyl azodicarboxylate in toluene is added dropwise over one hour to several hours to cause reaction with each other to yield the compound (7). If the phenol derivative has a low acidity, the latter synthesis is more preferable.

2) Deprotection Step

Subsequently, to the compound (7) synthesized by the above Mitsunobu reaction, 6 M through 12 M hydrochloric acid is added, and the mixture is refluxed with heating at 100° C. through 110° C. for several hours through 24 hours to yield the deprotected compound. If any substituent that is susceptible to acid hydrolysis, such as amide group, is present on the benzene ring of the compound (7) and if $R^1$ is tert-butoxycarbonyl group, the compound (7) is dissolved in methanol, and aqueous lithium hydroxide or sodium hydroxide is added thereto, which is brought into reaction at room temperature for several hours to several days, thereby hydrolyzing methyl esters. To the resultant compound, trifluoroacetic acid is then added at 0° C., and the temperature is raised to room temperature, thereby causing a reaction for 30 minutes to 2 hours and obtaining the deprotected compound. If $R^1$ is a benzyloxycarbonyl group, hydrogenolysis by palladium catalyst results in deprotection of the amino group, and following alkali hydrolysis yields the deprotected compound (8) of interest. A substituent Z″ is Z′, or represents any functional group converted during the deprotection and hydrolysis step.

The method for synthesizing the substituted phenoxy pyrrolidine analogue using the Mitsunobu reaction will be further described referencing Examples 5 through 7, wherein specific reactions were performed.

According to the synthetic pathway using the Mitsunobu reaction outlined below, methyl(2S,3R,4R)-1-benzoyl-3-(tert-butoxycarbonylmethyl)-4-hydroxypyrrolidine-2-carboxylate, used as the starting material in Examples 5 through 7, was synthesized.

[Chemical Formula 21]

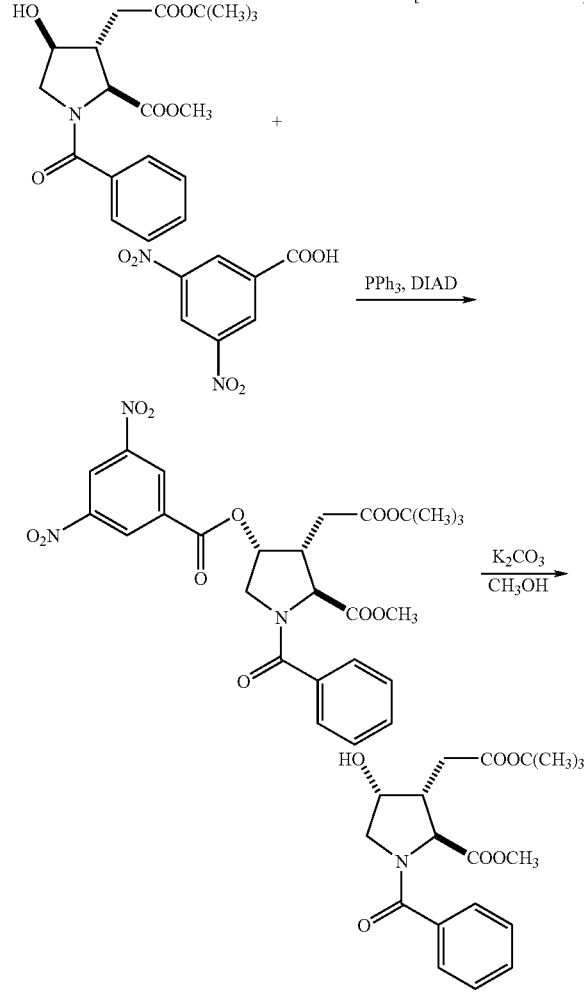

Specifically, to a solution of methyl(2S,3R,4S)-1-benzoyl-3-(tert-butoxycarbonylmethyl)-4-hydroxypyrrolidine-2-carboxylate (20.0 mg, 55.0 µmol) in THF(250 µL), triphenylphosphine (17.3 mg, 66 µmol) and 3,5-dinitrobenzoic acid (14.0 mg, 66 µmol) were added. After adding dropwise diisopropyl azodicarboxylate (12.5 µL, 63 µmol) to this solution at 0° C., the temperature was raised, and the mixture was stirred at room temperature for two hours. The reaction mixture was concentrated in vacuo, and the residue was purified by thin layer chromatography (silica gel 60, 0.5 mm, hexane/ethyl acetate=1/1) to obtain the coupling compound.

The coupling compound was suspended in methanol (900 µL) followed by addition of potassium carbonate (3.8 mg, 27.5 µmol), and the mixture was stirred for 10 minutes. To the reaction solution a 5% aqueous solution of potassium hydrogen sulfate was then added to be acidified, and the product was extracted with ethyl acetate. The organic phase was dried with anhydrous sodium sulfate, filtered, and concentrated in vacuo, and the resultant residue was purified by thin layer chromatography (silica gel 60, 0.5 mm, hexane/ethyl acetate=1/2, 2 developments) to obtain the compound of interest (16 mg, 80%). $^1$H NMR data of this compound is shown below.

$^1$H NMR (400 MHz, CDCl$_3$)(major rotamer) δ (ppm) 1.47 (9H), 2.42 (br, 1H),2.59-2.74 (complex, 3H), 3.61 (d, J =11.6 Hz, 1H),3.80 (s,3H),3.91(dd, J=3.6 and 11.6 Hz, 1H), 4.39 (d, J=9.2 Hz, 1H), 4.47 (br q J=3.6 Hz, 1H), 7.37-7.47 (complex, 3H), 7.58 (br d, J=7.2 Hz, 2H).

EXAMPLE 5

In Example 5, (2S,3R,4S)-3-(carboxymethyl)-4-(2-carboxyphenoxy)-pyrrolidine-2-carboxylate (Ib) was synthesized by the method shown below.

1) Mitsunobu Reaction Step

[Chemical Formula 22]

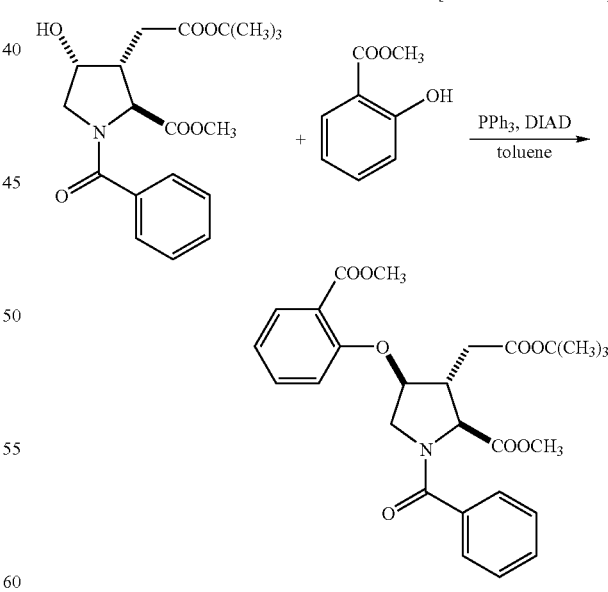

First, the Mitsunobu reaction above was performed. Specifically, to a solution of methyl2-hydroxybenzoate (8.70 µL, 67.1 µmol) in toluene (130 µL), triphenylphosphine (19.3 mg, 73.6 µmol) was added under the argon atmosphere, and the temperature of the reaction solution was raised to 80° C. To this was added dropwise a solution of methyl(2S,3R,4R)-1- benzoyl-3-(tert-butoxycarbonylmethyl)-4-hydroxypyrrolidine-2-carboxylate (21.6 mg, 59.4 μmol) and diisopropyl azodicarboxylate (15 μL, 76.2 μmol) in toluene (380 μL) and THF (150 μL) over three hours, and the mixture was stirred for further 24 hours. After the reaction mixture was cooled to room temperature, it was concentrated in vacuo, and the residue was sequentially purified by column chromatography (silica gel 60, hexane/ethyl acetate=3/2) and thin layer chromatography (silica gel 60, 0.5 mm, hexane/ethyl acetate=3/2, 2 developments) to obtain the compound of interest (9.1 mg, 31%). $^1$H NMR data of this compound is shown below.

$^1$H NMR (400 MHz, CDCl$_3$): (two rotamers) δ (ppm) 1.41 and 1.44 (s, 9H), 2.35 (dd, J=8.6 and 16 Hz) and 2.46 (dd, J=6.8 and 16 Hz) (1H), 2.56 (dd, J=6.4 and 16 Hz) and 2.60 (dd, J=6.8 and 16 Hz) (2H), 3.1-3.2 (m) and 3.24-3.32 (br m) (1H), 3.63 and 3.78 and 3.89 (s, 6H), 3.82-3.96 (complex), 4.32 (dd, J=5.8 and 13.8 Hz), 4.37 (br s), 4.71 (d J=5.6 Hz), 4.73-4.82 (complex), 6.91 (d, J=8 Hz) and 6.94 (d, J=8.4 Hz) (1H), 6.99-7.07 (complex, 1H), 7.34-7.5 (complex, 5H), 7.59 (d, J=8 Hz, 1H), 7.77 (t, J=8 Hz, 1H).

2) Deprotection Step

[Chemical Formula 23]

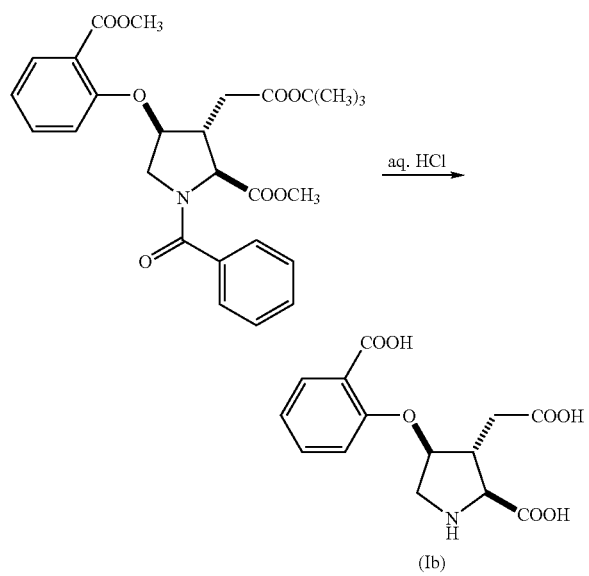

The above reaction was performed as the deprotection step. Specifically, to methyl(2S,3R,4S)-1-benzoyl-3-(tert-butoxycarbonylmethyl)-4-[2-(methoxycarbonyl)-phenoxyl]pyrrolidine-2-carboxylate (9.1 mg, 18.3 μmol), 6 M hydrochloric acid (0.6 mL) was added, and the mixture was refluxed with heating at 110° C. for seven hours. The reaction solution, after cooled down to room temperature, was washed with chloroform, lyophilized, and the residue was purified by ion exchange chromatography (Dowex 50WX8) to obtain the compound of interest (Ib) (3.9 mg, 69%). $^1$H NMR data of this compound is shown below.

$^1$H NMR (400 MHz, D$_2$O): δ (ppm) 2.38 (dd, J=8.6 and 16.2 Hz, 1H), 2.52 (dd, J=5.2 and 16.2 Hz, 1H), 2.92 (br, 1H), 3.46-3.59 (complex, 2H), 3.83 (d, J=5.2 Hz, 1H), 4.7 (1H), 6.89-6.97 (br, 2H), 7.24 (t, J=7.6 Hz, 1H), 7.30 (d, J=7.6 Hz, 1H).

EXAMPLE 6

In Example 6, (2S,3R,4S)-3-(carboxymethyl)-4-(3-carboxyphenoxy)-pyrrolidine-2-carboxylate (Ic) was synthesized by the method shown below.

1) Mitsunobu Reaction Step

[Chemical Formula 24]

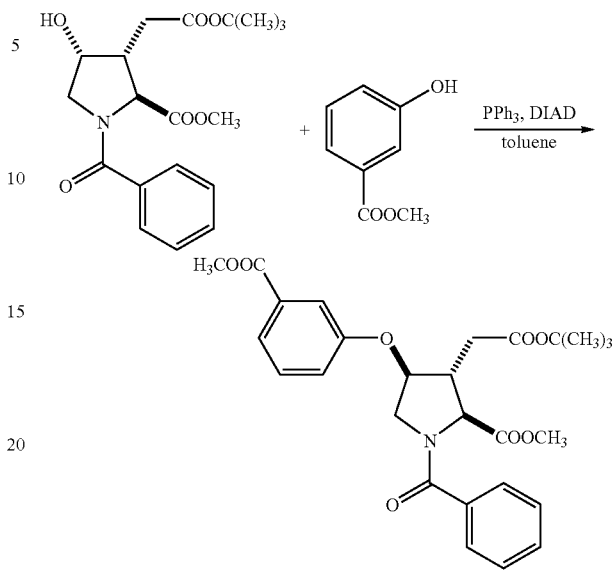

First, the above Mitsunobu reaction step was performed. Specifically, to a solution of methyl3-hydroxybenzoate(18.7 mg, 123 μmol) in toluene (250 μL), triphenylphosphine (35.7 mg, 136 μmol) was added under the argon atmosphere, and the temperature of the solution was raised to 80° C. To this was added dropwise a solution of methyl(2 S,3R,4R)-1-benzoyl-3-(tert-butoxycarbonylmethyl)-4-hydroxypyrrolidine-2-carboxylate (40 mg, 110 μmol) and diisopropyl azodicarboxylate (26.3 μL, 133 μmol) in toluene (700 μL) and THF (200 μL) over four hours, and stirring was continued for further 40 hours. After the reaction mixture was cooled to room temperature, it was concentrated in vacuo, and the residue was sequentially purified by column chromatography (silica gel 60, hexane/ethyl acetate=3/2) and thin layer chromatography (silica gel 60, 0.5mm, hexane/ethyl acetate=3/2, 3 developments) to obtain the compound of interest (24.6 mg, 45%). $^1$H NMR data of this compound is shown below.

$^1$H NMR (400 MHz, CDCl$_3$): (two rotamers) δ (ppm) 1.42 and 1.46 (s, 9H), 2.34 (dd, J=8.8 and 15.8 Hz) and 2.46 (dd, J=6.4 and 15.8 Hz) and 2.50 (dd, J=7.6 and 16.4 Hz) and 2.59 (dd, J=6.8 and 16.4 Hz) (2H), 3.07-3.16 and 3.17-3.25 (complex, 1H), 3.67 and 3.79 and 3.89 and 3.92 (s, 6H), 3.73-3.83 (complex), 3.86-3.95 (complex), 4.22-4.29 (m), 4.36 (br s), 4.69 (d, J=5.2 Hz), 4.76-4.84 (complex, 1H), 7.01-7.08 (m, 1H), 7.28-7.46 (complex, 5H), 7.48 (s, 1H), 7.57 (br d, 1H), 7.66 (br t, J=8.4 Hz, 1H).

2) Deprotection Step

[Chemical Formula 25]

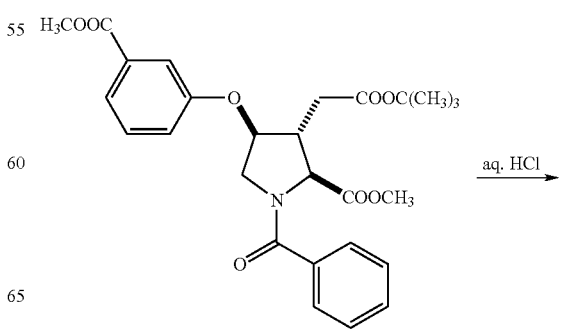

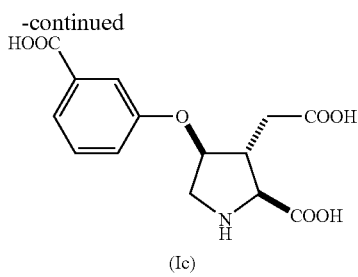

The above reaction was then performed as the deprotection step. Specifically, to methyl(2S,3R,4S)-1-benzoyl-3-(tert-butoxycarbonylmethyl)-4-[3-(methoxycarbonyl)phenoxy]pyrrolidine-2-carboxylate(20.3 mg, 40.8 μmol), 6 M hydrochloric acid (0.6 mL) was added, and the mixture was refluxed with heating at 110° C. for seven hours. The reaction solution, after cooled down to room temperature, was washed with chloroform, lyophilized, and the residue was purified by ion exchange chromatography (Dowex 50WX8) to obtain the compound of interest (Ic) (13 mg, 100%). $^1$H NMR data of this compound is shown below.

$^1$H NMR (400 MHz, D$_2$O): δ (ppm) 2.19 (dd, J=10 and 15.2 Hz, 1H), 2.34 (dd, J=6.4 and 15.2 Hz, 1H), 3.0 (br m, 1H), 3.55 (s, 2H), 3.84 (s, 1H), 4.83 (s, 1H), 6.94 (d, J=8 Hz, 1H), 7.17 (S, 1H), 7.20 (t, J=8 Hz, 1H), 7.31 (d, J=8 Hz, 1H).

EXAMPLE 7

In Example 7, (2S,3R,4S)-3-(carboxymethyl)-4-(4-carboxy-2-methoxyphenoxy)pyrrolidine-2-carboxylate (Id) was synthesized by the method shown below.
1) Mitsunobu Reaction Step

[Chemical Formula 26]

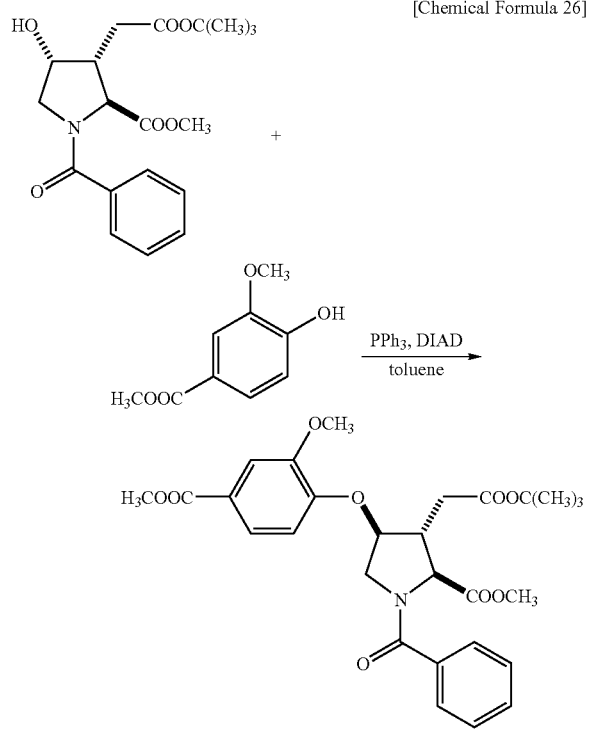

The above Mitsunobu reaction was performed. Specifically, to a solution of methyl4-hydroxy-3-methoxybenzoate (28.1 mg, 154 μmol) in toluene (200 μL), triphenylphosphine (44.7 mg,170 μmol) was added, and the temperature of the reaction solution was raised to 80° C. To this was added dropwise a solution of methyl(2S,3R,4R)-1-benzoyl-3-(tert-butoxycarbonylmethyl)-4-hydroxypyrrolidine-2-carboxylate (50 mg, 137 u mol) and diisopropyl azodicarboxylate (35.6 μL, 181 μmol) in toluene (800 μL), and the mixture was stirred for further 20 hours. The reaction mixture, after cooled down to room temperature, was concentrated in vacuo, and the residue was sequentially purified by column chromatography (silica gel 60, hexane/ethyl acetate=3/2), thin layer chromatography (silica gel 60, 0.5 mm, toluene/methanol=9/1), and thin layer chromatography (silica gel 60, 0.5 mm, hexane/ethyl acetate 3/2) to obtain the compound of interest (38.4 mg, 53%). TLC and $^1$H NMR data of this compound are shown below.

TLC: R$_f$=0.23 (silica gel, hexane/ethyl acetate=3/2)

$^1$H NMR (400 MHz, CDCl$_3$): (two rotamers) δ (ppm) 1.41 and 1.44 (s, 9H), 2.34 (dd, J=8.4 and 15.7 Hz) and 2.43 (dd, J=6.9 and 15.7 Hz) and 2.51 (dd, J=6.8 and 16.2 Hz) and 2.59 (dd, J=6.3 and 16.2 Hz) (2H), 3.11-3.19 and 3.22-3.3 (complex, 1H), 3.68 and 3.80 and 3.86 and 3.88 and 3.90 (s, 9H), 3.78-3.84 (complex) and 3.86-3.94 (complex), 4.22-4.28 (m), 4.37 (br s), 4.72 (d, J=5.6 Hz), 4.81-4.89 (complex, 1H), 6.88 (br d, J 8.3 Hz, 1H), 7.34-7.48 (complex, 4H), 7.52-7.66 (complex, 3H).

2) Deprotection Reaction

[Chemical Formula 27]

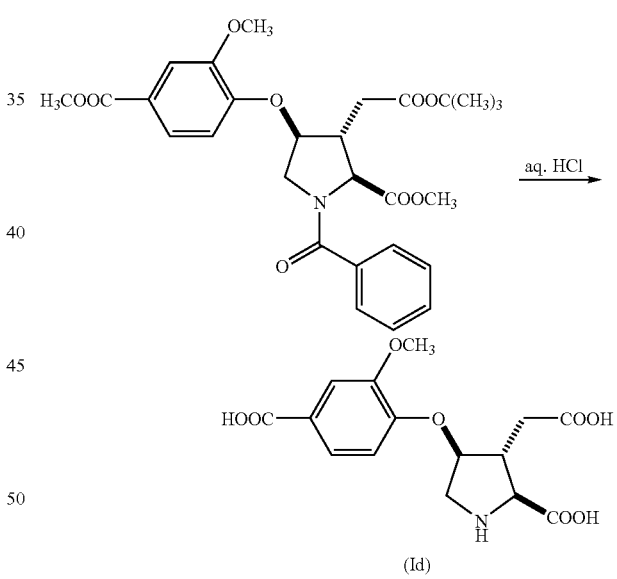

The above reaction was then performed as a deprotection step. Specifically, to methyl(2S,3R,4S)-1-benzoyl-3-(tert-butoxycarbonylmethyl)-4-(4-methoxycarbonyl-2-methoxyphenoxy)pyrrolidine-2-carboxylate(34.7 mg, 65.8 u mol), 6 M hydrochloric acid (2 mL) was added, and the mixture was refluxed with heating at 110° C. for 16 hours. The reaction solution, after cooled down to a room temperature, was washed with chloroform, lyophilized, and the residue was purified by ion exchange chromatography (Dowex 50WX8) to obtain the compound of interest (Id) (12.9 mg, 58%). $^1$H NMR data of this compound is shown below.

$^1$H NMR (400 MHz, D$_2$O): δ (ppm) 2.27 (dd, J=9.6 and 15.7 Hz, 1H), 2.44 (dd, J=5.7 and 15.7 Hz, 1H), 2.93-3.02 (br m, 1H), 3.52-3.61 (m, 2H), 3.69 (s, 3H), 3.84 (d, J=3.9 Hz, 1H), 4.88 (br, 1H), 6.92 (d, J=8.1 Hz, 1H), 7.35 (dd, J=1.9 and 8.1 Hz, 1H), 7.36 (br, 1H).

EXAMPLE 8

In Example 8, (2S,3R,4S)-3-carboxymethyl-4-(2-carboxy-4-methyl-phenoxy)pyrrolidine-2-carboxylate (Ie) was synthesized in the method shown below.

1) Coupling Step

[Chemical Formula 28]

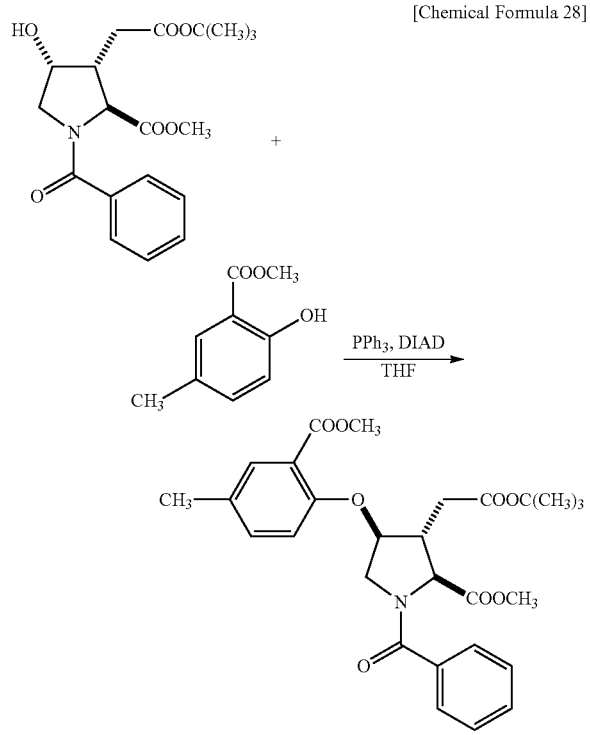

First, the above Mitsunobu reaction was performed. Specifically, to a solution of methyl(2 S,3R,4R)-1-benzoyl-3-(tert-butoxycarbonylmethyl)-4-hydroxypyrrolidine-2-carboxylate (38.0 mg, 105 µmol) in THF (0.9 mL), triphenylphosphine (69.0 mg, 263 µmol) and methyl2-hydroxy-5-methylbenzoate (30.3 µL, 210 µmol) were added under the argon atmosphere. Diisopropyl azodicarboxylate (54.5 µL, 277 µmol) was added dropwise to the reaction solution at room temperature, and the mixture was stirred for 16 hours at room temperature. The reaction solution was then concentrated in vacuo, and the residue was sequentially purified by column chromatography (silica gel 60, hexane/ethyl acetate=3/2), and thin layer chromatography (silica gel 60, 0.5mm, hexane/ethyl acetate 2/1) to obtain the coupling compound (13.1 mg, 24%). TLC and $^1$H NMR data of this compound are shown below.

TLC: $R_f$=0.25 (silica gel, hexane/ethyl acetate=2/1)

$^1$H NMR (400 MHz, CDCl$_3$): (two rotamers) δ (ppm) 1.40 and 1.43 (s, 9H), 2.28 and 2.31 (s, 3H), 2.25-2.37 (m), 2.44 (dd, J=6.5 and 15.7 Hz) and 2.54-2.8 (m) (2H), 3.08-3.17 and 3.21-3.3 (complex, 1H), 3.63, 3.78, 3.87, and 3.88 (s, 3H), 3.81-3.93 (complex), 4.29 (dd, J=5.6 and 14.2 Hz), 4.36 (br), 4.66-4.74 (complex), 6.80 (d, J=8.3 Hz) and 6.83 (d), 7.15-7.62 (complex).

2) Deprotection Step

[Chemical Formula 29]

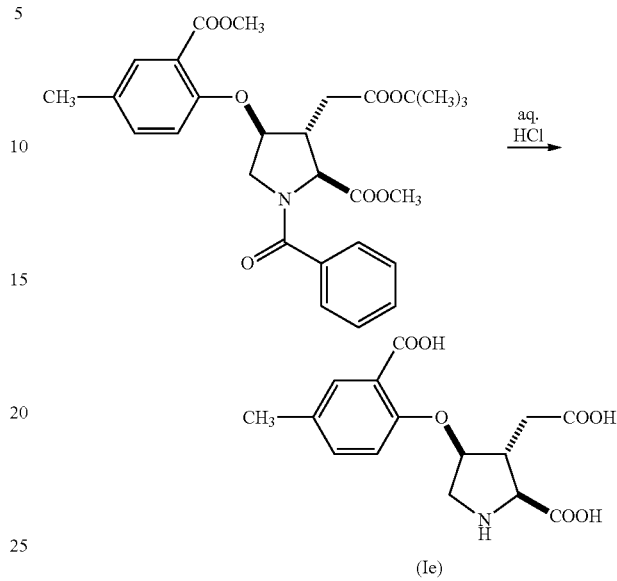

The above reaction was subsequently performed as the deprotection step. Specifically, to methyl(2S,3R,4S)-1-benzoyl-3-tert-butoxycarbonylmethyl-4-(2-methoxycarbonyl4-methylphenoxy)pyrrolidine-2-carboxylate (13.1 mg, 25.6 µmol), 6 M hydrochloric acid (1 mL) was added, and the mixture was refluxed with heating at 110° C. for 8 hours. The reaction solution, after cooled down to room temperature, was washed with chloroform, lyophilized, and the residue was purified by ion exchange chromatography (Dowex 50WX8) to obtain the compound of interest (Ie) (8.0 mg, 97%). TLC and $^1$H NMR data of this compound are shown below.

TLC: $R_f$=0.76 (Reverse phase, acetonitrile/water=2/1)

$^1$H NMR (400 MHz, D$_2$O): δ (ppm) 2.09 (s, 3H), 2.27 (dd, J=9.2 and 15.7 Hz, 1H), 2.45 (dd, J=5.7 and 15.7 Hz, 1H), 2.86-2.95 (m, 1H), 3.44 (m, 1H), 3.53 (br d, J=13.2 Hz, 1H), 3.82 (dd, J=1.3 and 4.8 Hz, 1H), 4.6 (1H), 6.80 (d, J=8.3 Hz, 1H), 7.04 (d, J=8.3 Hz, 1H), 7.08 (s, 1H).

<Synthesis of Substituted Phenoxypyrrolidine Analogue (II)>

According to the reaction scheme below, pyrrolidine analogues according to the second aspect of the invention, namely substituted phenoxypyrrolidine analogue (14) (this compound is encompassed in the scope of the general formula (II) described above) can be synthesized.

[Chemcial Formula 30]

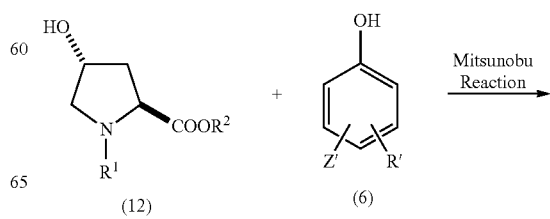

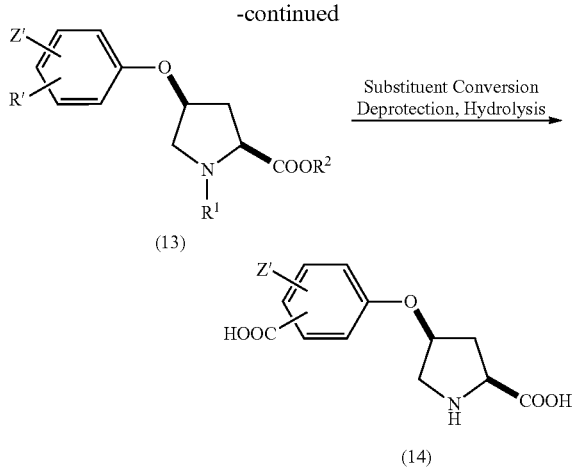

1) Mitsunobu Reaction Step

To a solution of compound (12), prepared from commercially available trans4-hydroxy-L-proline, triphenylphosphine, and phenol derivative (6) that is commercially available or synthesized according to the method known from any documents, in THF or DMF, dialkyl azodicarboxylate is added dropwise at room temperature over several minutes to one hour, then the mixture is allowed to stir at room temperature to 50° C. to afford the coupling compound (13).

As an alternative synthesis, to a solution of phenol derivative (6) and triphenylphosphine in toluene heated at 60° C. through 90° C., a solution of the compound (12) and dialkyl azodicarboxylate in toluene is added dropwise over one through several hours, thereby obtaining the compound (13). If the phenol derivative has low acidity, the latter synthesis is more preferable.

2) Deprotection Reaction

To the compound (13) synthesized by the above Mitsunobu reaction step, 6 M through 12 M hydrochloric acid is added, and the mixture is refluxed with heating at 100° C. through 110° C. over several through 24 hours to obtain the deprotected compound (14). If any substituent that is susceptible to acid hydrolysis, such as amide group, is present on the benzene ring of the compound (13) and if $R^1$ is tert-butoxycarbonyl group, the compound (13) is dissolved in methanol, followed by addition of aqueous lithium hydroxide or sodium hydroxide, then the mixture is reacted at room temperature for several hours to several days, thereby hydrolyzing methyl esters. To the resultant compound trifluoroacetic acid is then added at 0° C., and the temperature is raised to room temperature, thereby causing reaction for 30 minutes to 2 hours and obtaining the deprotected compound. If $R^1$ is a benzyloxycarbonyl group, hydrogenolysis with palladium catalyst results in deprotection of the amino group, and following alkali hydrolysis yields the deprotected compound of interest.

The synthesis of the above substituted phenoxypyrrolidine analogue (II) employing the Mitsunobu reaction step will be described in further detail in the following reference Examples 9 through 12.

EXAMPLE 9

In Example 9, (2S,4S)-4-(4-carboxyphenoxy)pyrrolidine-2-carboxylate (IIa) was synthesized by the method shown below.

1) Mitsunobu Reaction Step

[Chemical Formula 31]

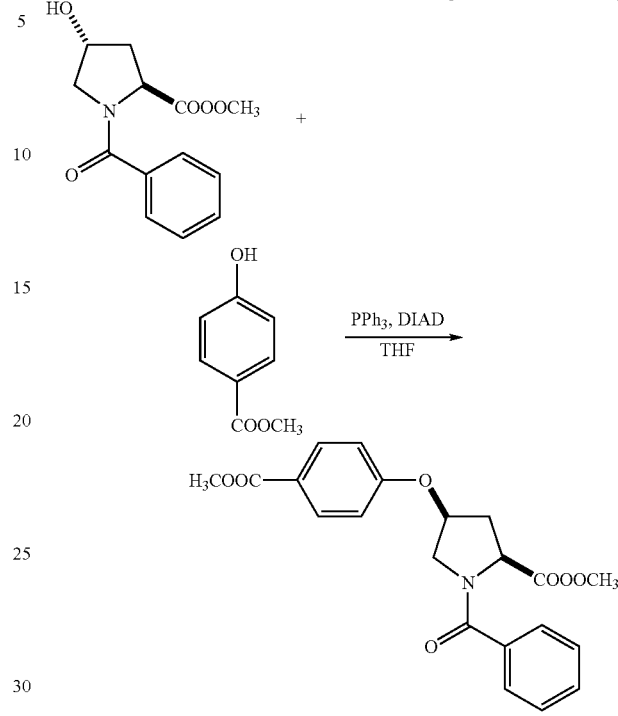

First, the above Mitsunobu reaction was performed. Specifically, to a solution of methyl(2S,4R)-1-benzoyl-4-hydroxypyrrolidine-2-carboxylate (68.7 mg, 276 μmol) in THF (500 μL), triphenylphosphine (181 mg, 690 μmol) and methyl4-hydroxybenzoate (84.0 mg, 552 μmol) were added under the argon atmosphere. Diisopropyl azodicarboxylate (143 μL, 726 μmol) was added dropwise at room temperature to the reaction solution slowly, and the mixture was stirred at room temperature for 30 minutes. The reaction mixture was then concentrated in vacuo, and the residue was sequentially purified by column chromatography (silica gel 60, hexane/ethyl acetate=2/3), and thin layer chromatography (silica gel 60, 0.5mm, toluene/methanol=9/1) to obtain the compound of interest (86.4 mg, 82%). TLC and $^1$H NMR data are shown below.

TLC: $R_f$=0.26 (silica gel, hexane/ethyl acetate=2/3)

$^1$H NMR (400 MHz, CDCl$_3$): (two rotamers) δ (ppm) 2.44-2.55 (m, 1H), 2.55-2.69 (m, 1H), 3.66 and 3.78 and 3.89 (s, 6H), 3.81-3.99 (complex), 4.2-4.29 (m), 4.52 (br d, J=8.4 Hz), 4.95-5.11 (complex), 6.82 (d, J=8.8 Hz, 2H) 7.35-7.48 (m, 4H), 7.56 (d, J=6.8 Hz, 1H), 7.98 (br t, J=8.4 Hz, 2H).

2) Deprotection Reaction

[Chemical Formula 32]

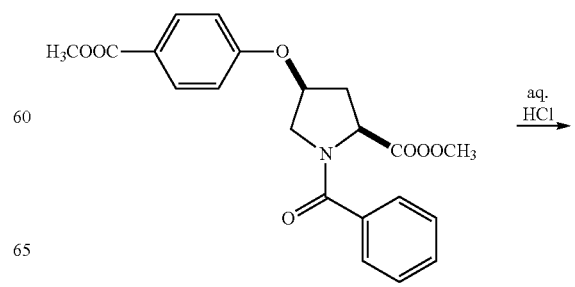

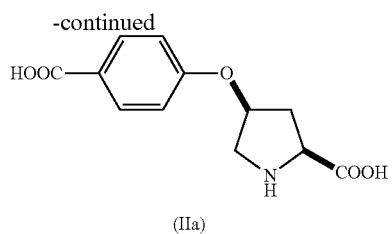

(IIa)

The above deprotection reaction was then performed. Specifically, to methyl(2S,4S)-1-benzoyl-4-[4-(methoxycarbonyl)phenoxy]pyrrolidine-2-carboxylate (36.2 mg, 94.4 μmol), 6 M hydrochloric acid (2 mL) was added, and the mixture was refluxed with heating at 110° C. for 5 hours. The reaction solution, after cooled down to room temperature, was washed with chloroform, lyophilized, and the residue was purified by ion exchange chromatography (Dowex 50WX8) to obtain the compound of interest (IIa) (23.2 mg, 98%). $^1$H NMR data is shown below.

$^1$H NMR (400 MHz, D$_2$O): δ (ppm) 2.39-2.44 (br m, 2H), 3.41 (dd, J=4 and 13.2 Hz, 1H), 3.59 (d, J=13.2 Hz, 1H), 4.13 (t, J=6.2 Hz, 1H), 5.1 (br, 1H), 6.81 (d, J=8.8 Hz, 2H), 7.72 (d, J=8.8 Hz, 2H).

EXAMPLE 10

In Example 10, (2S,4S)-4-(2-carboxy-4-methylphenoxy)-pyrrolidine-2-carboxylate (IIb) was synthesized according to the reaction scheme shown below.
1) Mitsunobu Reaction Step

[Chemical Formula 33]

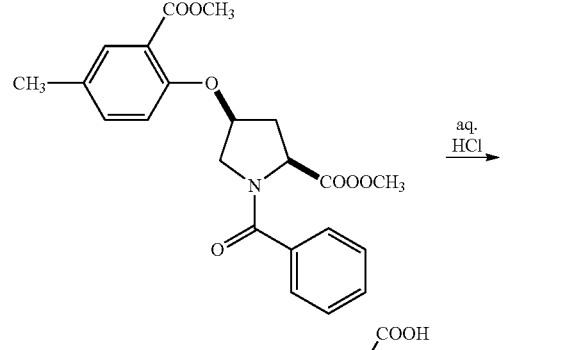

The above Mitsunobu reaction was first performed. Specifically, to a solution of methyl(2S,4R)-1-benzoyl-4-hydroxypyrrolidine-2-carboxylate (40.0 mg, 160 μmol) in THF (400 μL), triphenylphosphine (105 mg, 400 μmol) and methyl2-hydroxy-5-methylbenzoate (46.1 μL, 320 μmol) were added under the argon atmosphere. Diisopropyl azodicarboxylate (79.6 μL, 404 μmol) was added dropwise at room temperature to the reaction solution slowly, and the mixture was stirred at room temperature for 40 minutes. The reaction mixture was then concentrated in vacuo, and the residue was purified by thin layer chromatography (silica gel 60, 0.5mm, hexane/ethyl acetate=1/2, 4 developments) to obtain the compound of interest (41.1 mg, 65%). TLC and $^1$H NMR data are shown below.

TLC: R$_f$=0.29 (silica gel, hexane/ethyl acetate=1/2)

$^1$H NMR (400 MHz, CDCl$_3$): (two rotamers) δ (ppm) 2.30 (s, 3H), 2.43-2.73 (complex, 2H), 3.66 and 3.79 and 3.88 (s, 6H), 3.78-4.0 (complex), 4.2-4.30 (dd, J=5.4 and 13.4 Hz), 4.51 (br d, J=8.8 Hz), 4.81-4.89 (m), 4.94-5.02 (m, 1H), 6.75 (d, J=8.3 Hz) and 6.77 (d) (1H), 7.19-7.3 (m), 7.35-7.48 (m), 7.55-7.63 (m, 2H).

2) Deprotection Reaction

[Chemical Formula 34]

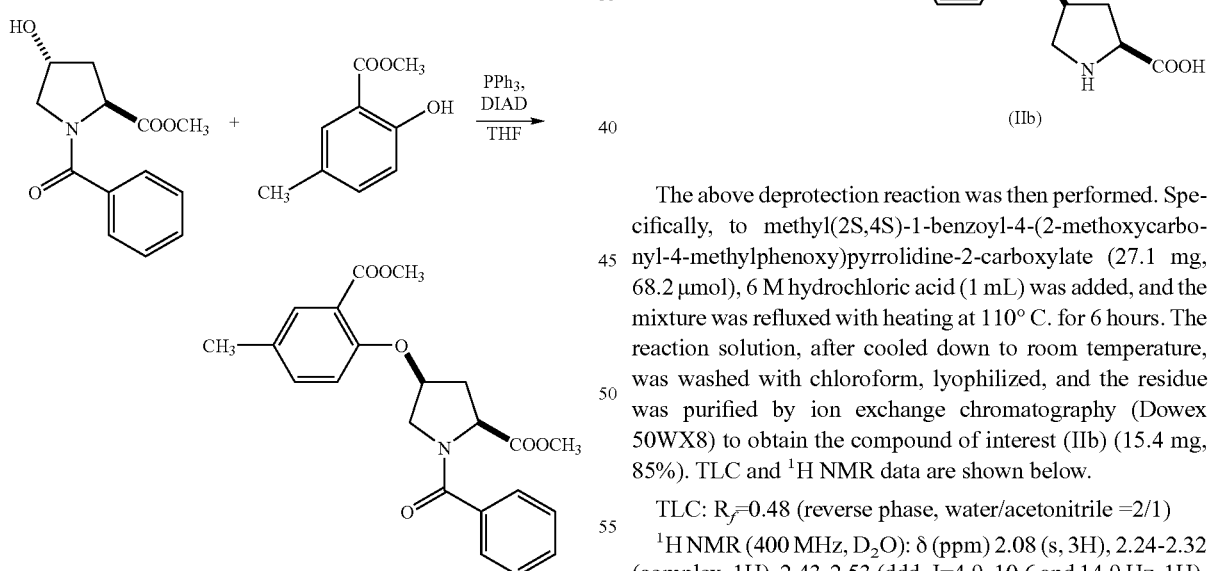

(IIb)

The above deprotection reaction was then performed. Specifically, to methyl(2S,4S)-1-benzoyl-4-(2-methoxycarbonyl-4-methylphenoxy)pyrrolidine-2-carboxylate (27.1 mg, 68.2 μmol), 6 M hydrochloric acid (1 mL) was added, and the mixture was refluxed with heating at 110° C. for 6 hours. The reaction solution, after cooled down to room temperature, was washed with chloroform, lyophilized, and the residue was purified by ion exchange chromatography (Dowex 50WX8) to obtain the compound of interest (IIb) (15.4 mg, 85%). TLC and $^1$H NMR data are shown below.

TLC: R$_f$=0.48 (reverse phase, water/acetonitrile =2/1)

$^1$H NMR (400 MHz, D$_2$O): δ (ppm) 2.08 (s, 3H), 2.24-2.32 (complex, 1H), 2.43-2.53 (ddd, J=4.9, 10.6 and 14.9 Hz, 1H), 3.31 (dd, J=4.1 and 12.9 Hz, 1H), 3.56 (d, J=12.9 Hz, 1H), 4.08 (dd, J=4.6 and 10.6 Hz, 1H), 4.88 (br, 1H), 6.73 (d, J=8.3 Hz, 1H), 7.08 (d, J=8.3 Hz, 1H), 7.18 (s,1H).

EXAMPLE 11

In Example 11, (2S,4S)-4-(2-bromo-4-carboxyphenoxy) pyrrolidine-2-carboxylate (IIc) was synthesized according to the reaction scheme shown below.

1) Mitsunobu Reaction

[Chemical Formula 35]

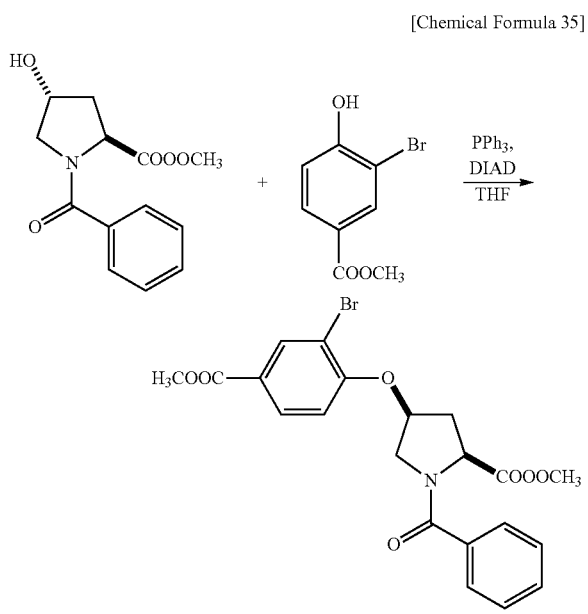

The above Mitsunobu reaction was first performed. Specifically, to a solution of methyl(2S,4R)-1-benzoyl-4-hydroxypyrrolidine-2-carboxylate (42.3 mg, 170 µmol) in THF (500 µL), triphenylphosphine (111 mg, 423 µmol) and methyl3-bromo-4-hydroxybenzoate (78.6 mg, 340 µmol) were added under the argon atmosphere. Diisopropyl azodicarboxylate (88.0 µL, 447 µmol) was slowly added dropwise to the reaction solution at room temperature, and the mixture was stirred at room temperature for 30 minutes. The reaction mixture was then concentrated in vacuo, and the residue was sequentially purified by column chromatography (silica gel 60, hexane/ethyl acetate=1/3) and thin layer chromatography (silica gel 60, 0.5 mm, toluene/methanol/chloroform=8/1/1) to obtain the compound of interest (77.7 mg, 99%). TLC and $^1$H NMR data are shown below.

TLC: $R_f$=0.37 (silica gel, hexane/ethyl acetate=1/3)

$^1$H NMR (400 MHz, CDCl$_3$): (two rotamers) δ (ppm) 2.52-2.8 (complex, 2H), 3.73 and 3.82 and 3.89 (s, 6H), 3.89-4.03 (complex), 4.31-4.39 (br dd, J=5.4 and 14.2 Hz), 4.58 (d, J=8.5 Hz), 4.96-5.03 (complex), 5.06-5.13 (complex), 6.75 (d, J=9.0 Hz) and 6.81 (d, J=8.8 Hz) (1H), 7.36-7.49 and 7.56-7.62 (complex, 5H), 7.9-8.0 (m, 1H), 8.24 (d, J=2.0 Hz, 1H).

2) Deprotection Reaction

[Chemical Formula 36]

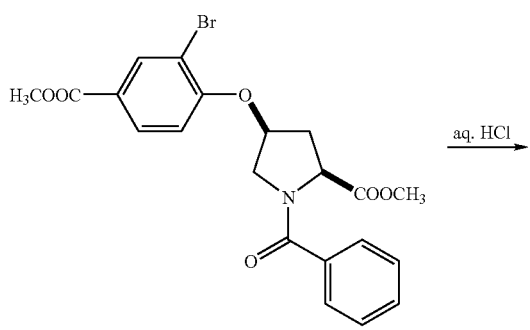

-continued

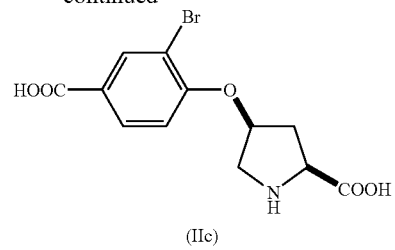

The above deprotection reaction was then performed. Specifically, to methyl(2S,4S)-1-benzoyl-4-[2-bromo-4-(methoxycarbonyl)phenoxy]pyrrolidine-2-carboxylate (33.2 mg, 71.8 µmol), 6 M hydrochloric acid (2 mL) was added, and the mixture was refluxed with heating at 110° C. for 5 hours. The reaction solution, after cooled down to room temperature, was washed with chloroform, lyophilized, and the residue was purified by ion exchange chromatography (Dowex 50WX8) to obtain the compound of interest (IIc) (16.7 mg, 70%). TLC and $^1$H NMR data are shown below.

TLC: $R_f$=0.71 (reverse phase, water/acetonitrile=1/1)

$^1$H NMR (400 MHz, D$_2$O): δ (ppm) 2.4-2.51 (complex, 2H), 3.42 (dd, J=3.9 and 13.2 Hz, 1H), 3.61 (d, J=13.2 Hz, 1H), 4.14 (dd, J=4.7 and 8.9 Hz, 1H), 5.05 (br s, 1H), 6.81 (d, J=8.5 Hz, 1H), 7.59 (dd, J=2 and 8.5 Hz, 1H), 7.85 (d, J=2 Hz, 1H).

EXAMPLE 12

In Example 12, (2S,4S)-4-[3-carboxy-5-(methylcarbamoyl)phenoxy]-pyrrolidine-2-carboxylate (IId) was synthesized according to the reaction scheme shown below.

1) Mitsunobu Reaction

[Chemical Formula 37]

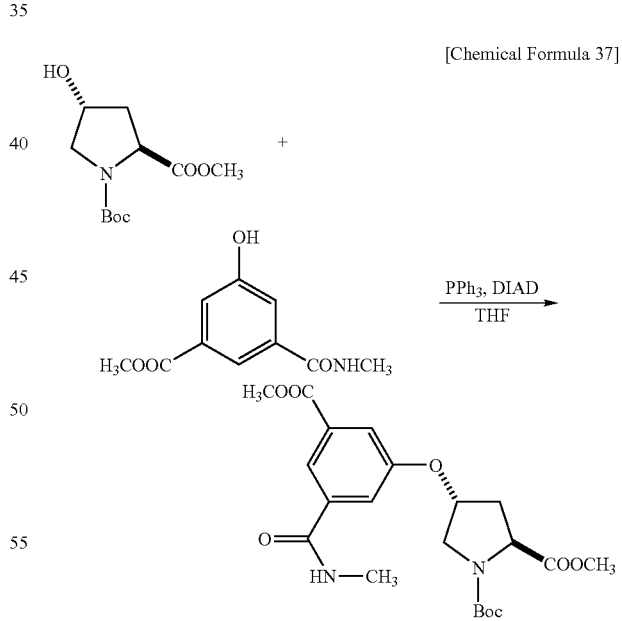

The above Mitsunobu reaction was first performed. Specifically, to a solution of methyl(2S,4R)-1-(tert-butoxycarbonyl)-4-hydroxypyrrolidine -2-carboxylate (40 mg,163 µmol) in THF (1 mL), triphenylphosphine(107 mg, 408 µmol) and methyl5-hydroxy-3-(methylcarbamoyl)benzoate (68.2 mg, 326 µmol) were added under the argon atmosphere. Diisopropyl azodicarboxylate (84.5 µL, 429 µmol) was slowly added dropwise to the reaction solution at room temperature, and the mixture was stirred at room temperature for 10 hours. The reaction mixture was then concentrated in vacuo, and the residue was sequentially purified by column chromatography (silica gel 60, hexane/ethyl acetate=1/1 through 1/3) and thin layer chromatography (silica gel 60, 0.5 mm, toluene/methanol=9/1) to obtain the compound of interest (46.2 mg, 65%). TLC and $^1$H NMR data are shown below.

TLC: $R_f$=0.15 (silica gel, toluene/methanol=9/1)

$^1$H NMR (400 MHz, CDCl$_3$): (two rotamers) δ (ppm) 1.43 and 1.48 (s, 9H), 2.44-2.59 (complex, 2H), 3.01-3.06 (m, 3H), 3.65-3.85 (complex, 5H), 3.93 (s, 3H), 4.45 (dd, J=2.7 and 8.5 Hz) and 4.57 (dd, J=3.7 and 7.6 Hz) (1H), 4.98-5.07 (m, 1H), 6.27 (br s, 1H), 7.51 (br s, 1H), 7.57 (br, 1H), 7.92 (br, 1H).

2) Deprotection Reaction

TLC: $R_f$=0.63 (reverse phase, methanol/water=2/1)

$^1$H NMR (400 MHz, D$_2$O): δ (ppm) 2.4-2.46 (m, 2H), 2.73 (s, 3H), 3.43 (dd, J=3.9 and 12.9 Hz, 1H), 3.61 (d, J=12.9 Hz, 1H), 4.14 (dd, J=6.2 and 6.8 Hz, 1H), 5.09-5.13 (br 1H), 7.18 (dd, J=1.6 and 2.4 Hz, 1H), 7.38 (dd, J=1.2 and 2.4 Hz, 1H), 7.62 (br, 1H).

<Synthesis (1) of the Substituted Phenylthiopyrrolidine Analogue (III)>

Substituted phenylthiopyrrolidine analogue (17) (this compound is encompassed in the scope of the general formula (III)), a pyrrolidine analogue according to the third aspect of the invention, can be synthesized according to the reaction scheme shown below.

[Chemical Formula 38]

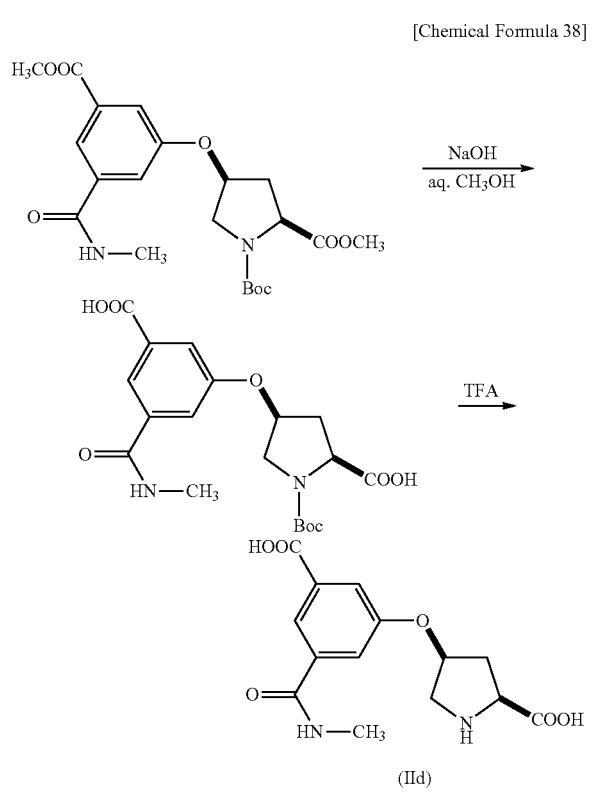

[Chemical Formula 39]

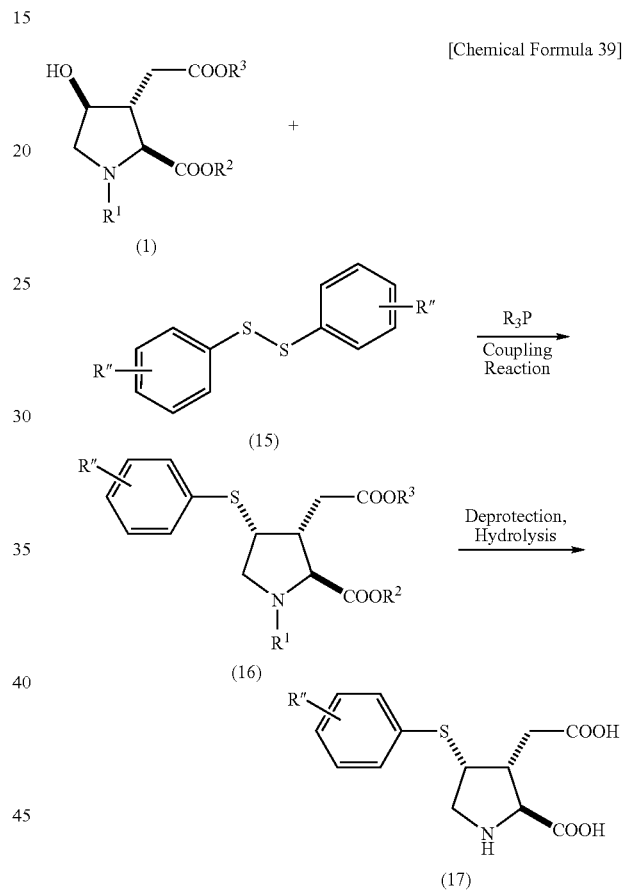

The above deprotection reaction was then performed. Specifically, methyl(2S,4S)-1-(tert-butoxycarbonyl)-4-[3-(methoxycarbonyl)-5-(methylcarbamoyl)-phenoxy]pyrrolidine-2-carboxylate (39.2 mg, 89.8 µmol) was dissolved in methanol (200 µL), 1 M sodium hydroxide (198 µL) was added thereto, and the mixture was stirred at room temperature for 16 hours. After an additional 1M sodium hydroxide (27 µL) added and further 7-hour of stirring, an aqueous solution of 5% potassium hydrogen sulfate was added to the reaction solution to be acidified. The reaction mixture was concentrated in vacuo, and the residue was purified by column chromatography (reverse phase, methanol/water=2/1) to obtain the carboxylic compound (27.0 mg, 74%). TLC: $R_f$=0.70 (reverse phase, methanol/water=2/1).

To thus obtained carboxylic compound (20 mg, 49 µmol), trifluoroacetic acid (1 mL) was added at 0° C., and the mixture was stirred for 2 hours. The reaction mixture was concentrated in vacuo, and the residue was purified by ion exchange chromatography (Dowex 50WX8) to obtain the compound of interest (IId) (14.1 mg, 93%). TLC and $^1$H NMR data are shown below.

(Coupling Step)

Specifically, a solution of 4-hydroxyproline derivative (1) in THF or DMF containing tributylphosphine and substituted diphenyl disulfide (15) that is commercially available or synthesized according to any method known from documents is heated to obtain the coupled compound (16).

(Deprotection Step)

As the deprotection step, to the compound (16) synthesized in the above coupling step, 6 M through 12 M hydrochloric acid is added, and the mixture is refluxed with heating at 100° C. through 110° C. for several hours through 24 hours to obtain deprotected compound (17). If any substituent that is susceptible to acid hydrolysis, such as amide group, is present on the benzene ring of the compound (16) and if R$^1$ is tert-butoxycarbonyl group, the compound (16) is dissolved in methanol, aqueous lithium hydroxide or sodium hydroxide is added thereto, which is then brought into reaction at room temperature for several hours to several days, thereby hydrolyzing methyl esters. To the resultant compound, trifluoroacetic acid is then added at 0° C., and the temperature is raised to room temperature, thereby causing reaction for 30 minutes to 2 hours and obtaining the deprotected compound. If $R^1$ is a benzyloxycarbonyl group, hydrogenolysis by palladium catalyst results in deprotection of the amino group, and following alkali hydrolysis yields a deprotected compound of interest.

The above Synthesis (1) for substituted phenylthiopyrrolidine analogue (III) will be described in further detail, referencing Examples 13 through 16 wherein specific reactions were performed.

EXAMPLE 13

In Example 13, (2S,3R,4R)-3-(carboxymethyl)-4-(4-methoxyphenylthio)-pyrrolidine -2-carboxylate (IIIa) was synthesized according to the method shown below.

1) Coupling Step

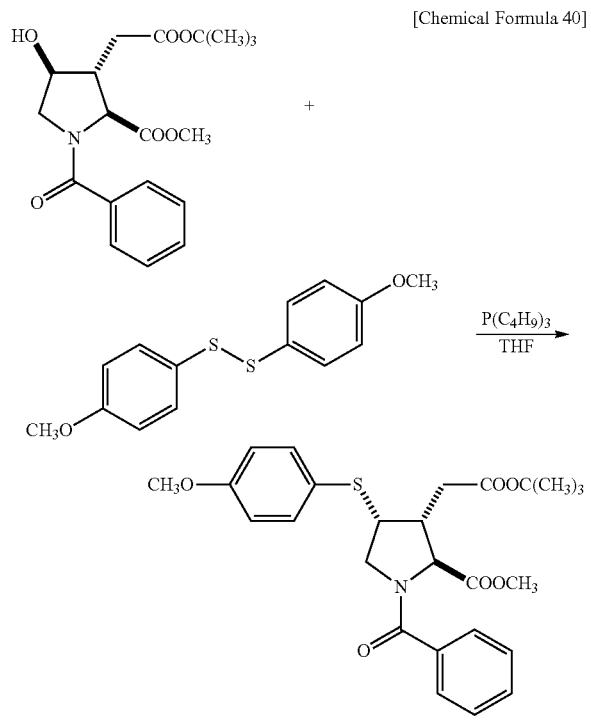

[Chemical Formula 40]

To a solution of methyl(2S,3R,4S)-1-benzoyl-3-(tert-butoxycarbonylmethyl)-4-hydroxypyrrolidine-2-carboxylate (57.5 mg, 158 µmol) in THF (1 mL), 1,2-bis(4-methoxyphenyl)disulfan (132 mg, 474 µmol) and tributylphosphine (118 µL, 474 µmol) were added under the argon atmosphere, and the reaction solution was stirred at 80° C. for 20 hours. To the reaction mixture, after cooled down to room temperature, water was added, and the product was extracted with ethyl acetate, and concentrated in vacuo, and the residue was purified by column chromatography (silica gel 60, hexane/ethyl acetate=2/1) to obtain the compound of interest (64.9 mg, 85%). TLC and $^1$H NMR data are shown below.

TLC: $R_f$=0.47 (silica gel, hexane/ethyl acetate=2/1)

$^1$H NMR (400 MHz, CDCl$_3$): (two rotamers) δ (ppm) 1.41 and 1.47 (s, 9H), 2.70 (dd, J=5.2 and 17.2 Hz, 1H) 2.86 (dd, J=9.2 and 17.2 Hz, 1H), 2.9-3.01 (m, 1H), 3.46 (br s), 3.55 (br d, J=10 Hz), 3.74 and 3.80 (s, 3H), 3.79 (s, 3H), 3.83-3.97 (complex, 2H), 4.47 (d, J=9.2 Hz, 1H), 6.69 (d, J=8.8 Hz) and 6.87 (d, J=8.8 Hz) (2H), 7.17 (dt, J=2 and 8.8 Hz, 2H), 7.34-7.46 (complex, 3H), 7.55 (m, 2H).

2) Deprotection Step

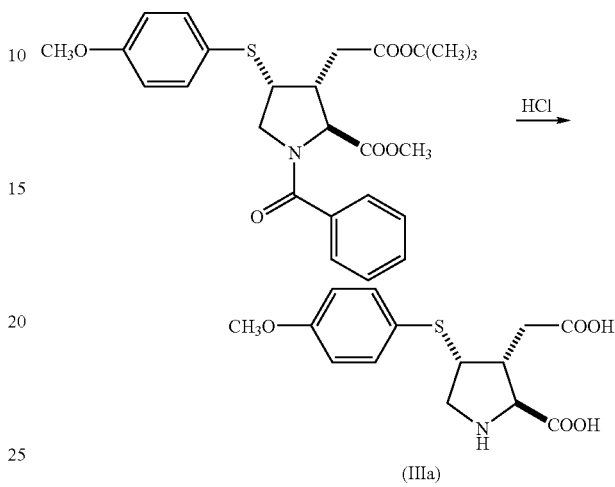

[Chemical Formula 41]

As the deprotection step, the above reaction was performed. Specifically, to methyl(2S,3R,4S)-1-benzoyl-3-(tert-butoxycarbonylmethyl)-4-(4-methoxyphenylthio)-pyrrolidine-2-carboxylate (35.8 mg, 73.7 µmol), 6 M hydrochloric acid (2 mL) was added, and the mixture was refluxed with heating at 110° C. for 3 hours. The reaction solution, after cooled down to room temperature, was washed with chloroform, lyophilized, and the residue was purified by ion exchange chromatography (Dowex 50WX8) to obtain the compound of interest (IIIa) (19.1 mg, 83%). TLC and $^1$H NMR data are shown below.

TLC: $R_f$=0.72 (reverse phase, acetonitrile/water=1/1)

$^1$H NMR (400 MHz, D$_2$O): δ (ppm) 2.55 (dd, J=10.6 and 16.8 Hz, 1H), 2.72 (dd, J=4 and 16.8 Hz, 1H), 2.72-2.81 (m, 1H), 3.23 (d, J=12.8 Hz, 1H), 3.43 (dd, J=5.2 and 12.8 Hz, 1H), 3.64 (s, 3H), 3.77 (d, J=10 Hz, 1H), 3.98 (br, 1H), 6.80 (d, J=8.8 Hz, 2H), 7.30 (d, J=8.8 Hz, 2H).

EXAMPLE 14

In Example 14, (2S,3R,4R)-3-(carboxymethyl)-4-(4-methylphenylthio)-pyrrolidine-2-carboxylate (IIIb) was synthesized by the method shown below.

1) Coupling Step

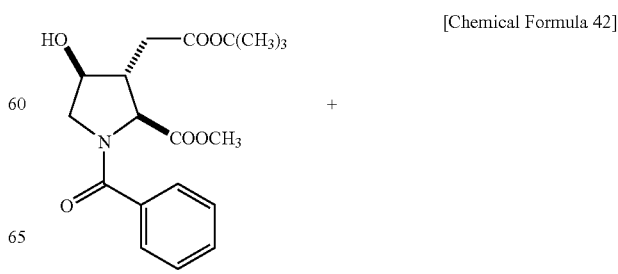

[Chemical Formula 42]

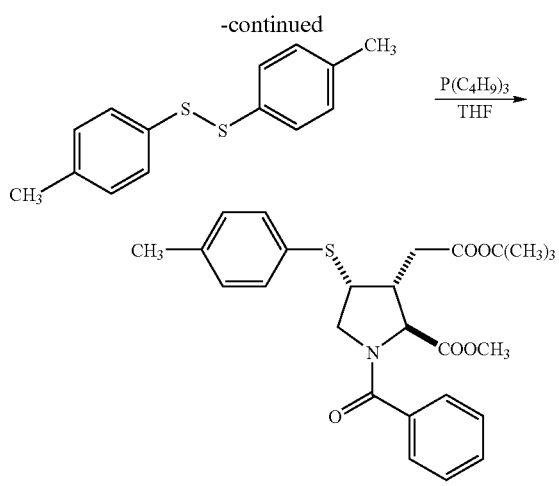

To a solution of methyl(2S,3R,4S)-1-benzoyl-3-(tert-butoxycarbonylmethyl)-4-hydroxypyrrolidine-2-carboxylate (54.8 mg, 151 μmol) in THF (1 mL), 1,2-bis(4-methylphenyl)disulfan (109 mg, 442 μmol) and tributylphosphine (113 μL, 453 μmol) were added under the argon atmosphere, and the reaction solution was stirred at 80° C. for 48 hours. To the reaction mixture, after cooled down to room temperature, water was added, and the product was extracted with dichloromethane and concentrated in vacuo, and the residue was purified by column chromatography (silica gel 60, hexane/ethyl acetate=2/1) to obtain the compound of interest (43 mg, 61%). TLC and $^1$H NMR data are shown below.

TLC: $R_f$=0.27 (silica gel, hexane/ethyl acetate=2/1)

$^1$H NMR (400 MHz, CDCl$_3$): (two rotamers) δ (ppm) 1.40 and 1.46 (s, 9H), 2.27 and 2.34 (s, 3H), 2.69 (dd, J=5.6 and 17.2 Hz, 1H), 2.86 (dd, J=9.4 and 17.2 Hz, 1H), 2.92-3.03 (m, 1H), 3.46 (br s), 3.58 (br d, J=9.2 Hz, 1H), 3.79 (s, 3H), 3.88-3.98 (complex), 4.46 (d, J=8.8 Hz, 1H), 6.99 (d, J=8.2 Hz, 2H), 7.13 (br d, J=8.2 Hz), 7.33-7.46 (complex), 7.52-7.57(m).

2) Deprotection Step

[Chemical Formula 43]

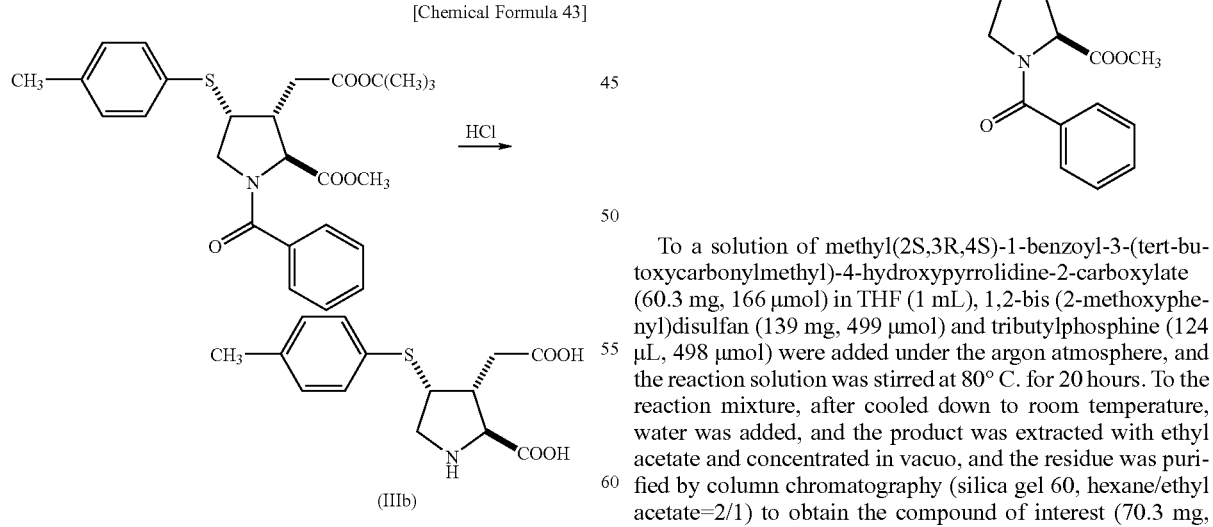

As the deprotection step, the above reaction was then performed. Specifically, to methyl(2S,3R,4R)-1-benzoyl-3-(tert-butoxycarbonylmethyl)-4-(4-methylphenylthio)pyrrolidine-2-carboxylate (36.4 mg, 77.5 μmol), 6 M hydrochloric acid (2 mL) was added, and the mixture was refluxed with heating at 110° C. for 5 hours. The reaction solution, after cooled down to room temperature, was washed with chloroform, lyophilized, and the residue was purified by ion exchange chromatography (Dowex 50WX8) to obtain the compound of interest (IIIb) (23 mg, 100%). TLC and $^1$H NMR data are shown below.

TLC: $R_f$=0.71 (reverse phase, acetonitrile/water=1/1)

$^1$H NMR (400 MHz, D$_2$O): δ (ppm) 2.13 (s, 3H), 2.57 (dd, J=10.4 and 17.2 Hz, 1H), 2.73 (dd, J=4.6 and 17.2 Hz, 1H), 2.76-2.84 (m, 1H), 3.23 (d, J=12.4 Hz, 1H), 3.47 (dd, J=5.4 and 12.4 Hz, 1H), 3.78 (d, J=10.4 Hz, 1H), 4.06 (br, 1H), 7.05 (d, J=8 Hz, 2H), 7.22 (d, J=8 Hz, 2H).

EXAMPLE 15

In Example 15, (2S,3R,4R)-3-(carboxymethyl)-4-(2-methoxyphenylthio)-pyrrolidine-2-carboxylate (IIIc) was synthesized by the method shown below.

1) Coupling Step

[Chemical formula 44]

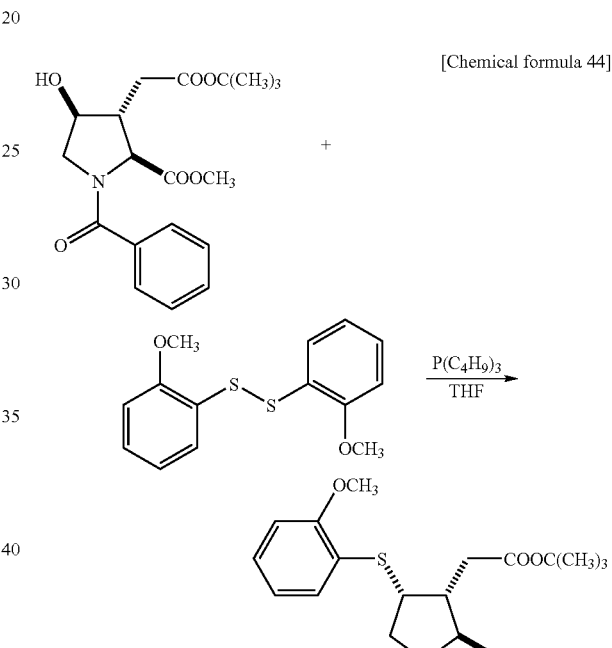

To a solution of methyl(2S,3R,4S)-1-benzoyl-3-(tert-butoxycarbonylmethyl)-4-hydroxypyrrolidine-2-carboxylate (60.3 mg, 166 μmol) in THF (1 mL), 1,2-bis (2-methoxyphenyl)disulfan (139 mg, 499 μmol) and tributylphosphine (124 μL, 498 μmol) were added under the argon atmosphere, and the reaction solution was stirred at 80° C. for 20 hours. To the reaction mixture, after cooled down to room temperature, water was added, and the product was extracted with ethyl acetate and concentrated in vacuo, and the residue was purified by column chromatography (silica gel 60, hexane/ethyl acetate=2/1) to obtain the compound of interest (70.3 mg, 87%). TLC and $^1$H NMR data are shown below.

TLC: $R_f$=0.47 (silica gel, hexane/ethyl acetate=2/1)

$^1$H NMR (400 MHz, CDCl$_3$): (two rotamers) δ (ppm) 1.38 and 1.44 (s, 9H), 2.66 (dd, J=5.6 and 16.8 Hz, 1H), 2.89-3.05 (complex), 3.47 (br s), 3.59 (dd, J=2.6 and 11.4 Hz, 1H), 3.73 (s, 3H), 3.79 (s, 3H) 3.86-4.03 (complex), 4.04-4.1 (m, 1H), 4.50

(br d, J=8.4 Hz, 1H), 6.76-6.81 and 6.88-6.95 (m), 7.19-7.25 (complex), 7.33-7.43 (complex), 7.53 (br d, J=7.6 Hz, 2H).

2) Deprotection Step

[Chemical Formula 45]

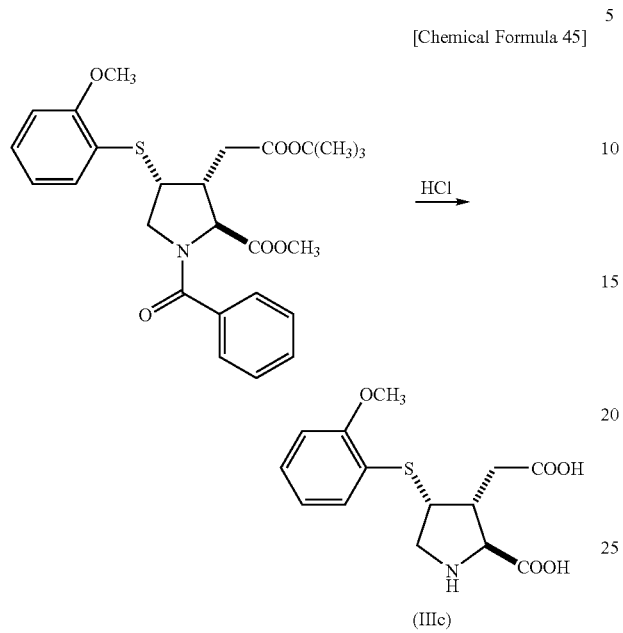

As the deprotection step, the above reaction was then performed. Specifically, to methyl(2S,3R,4R)-1-benzoyl-3-(tert-butoxycarbonylmethyl)-4-(2-methoxyphenylthio)pyrrolidine-2-carboxylate (45.9 mg, 94.5 μmol) obtained at the coupling step, 6 M hydrochloric acid (2 mL) was added, and the mixture was refluxed with heating at 110° C. for 3 hours. The reaction solution, after cooled down to room temperature, was washed with chloroform, lyophilized, and the residue was purified by ion exchange chromatography (Dowex 50WX8) to obtain the compound of interest (IIIc) (27.6 mg, 94%). TLC and $^1$H NMR data are shown below.

TLC: $R_f$=0.72 (reverse phase, acetonitrile/water=1/1)

$^1$H NMR (400 MHz, D$_2$O): δ (ppm) 2.44 (dd, J=10.8 and 16.6 Hz, 1H), 2.57 (dd, J=4.4 and 16.6 Hz, 1H), 2.68-2.78 (m, 1H), 3.15 (d, J=12.8 Hz, 1H), 3.40 (dd, J=5.2 and 12.8 Hz, 1H), 3.68 (s, 3H), 3.77 (d, J=10 Hz, 1H), 4.10 (br, 1H), 6.80 (t, J=7.6 Hz, 1H), 6.86 (d, J=8.2 Hz, 1H), 7.20 (br t, 1H), 7.27 (d, J=7.6 Hz, 1H).

EXAMPLE 16

In Example 16, (2S,3R,4R)-3-(carboxymethyl)-4-(3-bromophenylthio)-pyrrolidine-2-carboxylate (IIId) was synthesized by the method shown below.

1) Coupling Step

[Chemical Formula 46]

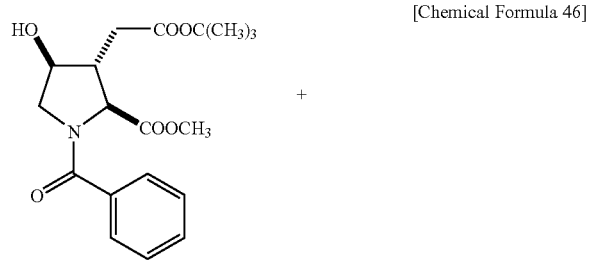

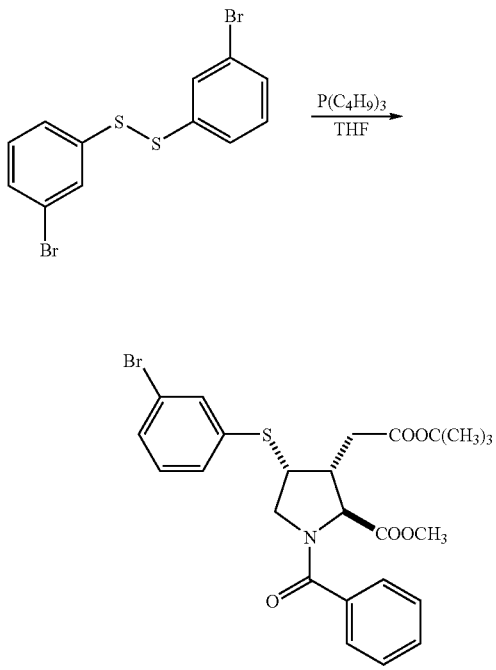

To a solution of methyl(2S,3R,4S)-1-benzoyl-3-(tert-butoxycarbonylmethyl)-4-hydroxypyrrolidine-2-carboxylate (52.0 mg, 143 μmol) in THF (1 mL), 1,2-bis(3-bromophenyl) disulfan (161 mg, 428 μmol) and tributylphosphine (107 μL, 429 μmol) were added under the argon atmosphere, and the reaction solution was stirred at 80° C. for 21 hours. To the reaction mixture, after cooled down to room temperature, water was added, and the product was extracted with dichloromethane and concentrated in vacuo, and the residue was purified by column chromatography (silica gel 60, hexane/ethyl acetate=2/1) to obtain the compound of interest (49 mg, 64%). TLC and $^1$H NMR data are shown below.

TLC: $R_f$=0.27 (silica gel, hexane/ethyl acetate=2/1)

$^1$H NMR (400 MHz, CDCl$_3$): (two rotamers) δ (ppm) 1.39 and 1.45 (s, 9H), 2.71 (dd, J=5.6 and 17.6 Hz, 1H), 2.81 (dd, J=9.6 and 17.6 Hz, 1H), 2.97-3.06 (complex, 1H), 3.49 (s), 3.58 (dd, J=2.2 and 11.4 Hz, 1H), 3.81 (s, 3H), 3.96 (dd, J=4.6 and 11.4 Hz, 1H), 4.01-4.07 (m), 4.46 (d, J=8.8 Hz, 1H), 7.06 (t, J=8 Hz, 1H), 7.16 (br dt, J=8.4 Hz, 1H), 7.31-7.34 (m), 7.37-7.46 (complex), 7.52-7.57 (m, 2H).

2) Deprotection Step

[Chemical Formula 47]

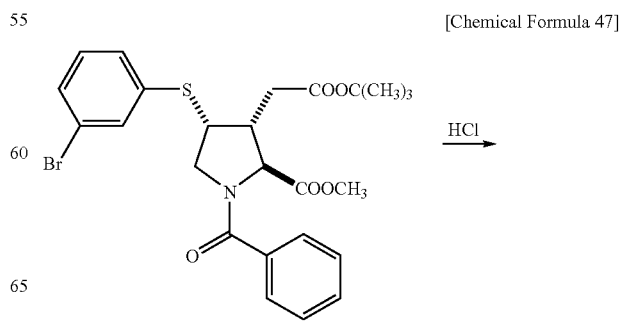

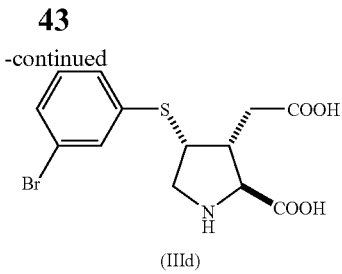

(IIId)

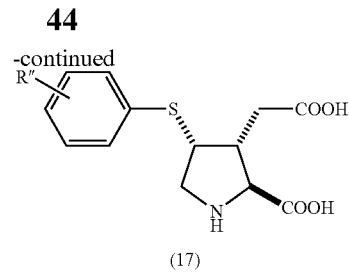

(17)

As the deprotection step, the above reaction was then performed. Specifically, to methyl(2S,3R,4R)-1-benzoyl-3-(tert-butoxycarbonylmethyl)-4-(3-bromophenylthio)pyrrolidine-2-carboxylate (29.6 mg, 55.4 μmol), 6 M hydrochloric acid (2 mL) was added, and the mixture was refluxed with heating at 110° C. for 3 hours. The reaction solution, after cooled down to room temperature, was washed with chloroform, lyophilized, and the residue was purified by ion exchange chromatography (Dowex 50WX8) to obtain the compound of interest (IIId) (16.7 mg, 84%). TLC and $^1$H NMR data are shown below.

TLC: $R_f$=0.67 (reverse phase, acetonitrile/water=1/1)

$^1$H NMR (400 MHz, $D_2O$): δ (ppm) 2.47 (dd, J=10.8 and 17.2 Hz, 1H), 2.69 (dd, J=4.2 and 17.2 Hz, 1H), 2.76-2.85 (m, 1H), 3.24 (d, J=12.8 Hz, 1H), 3.51 (dd, J=5.0 and 12.8 Hz, 1H), 3.77 (d, J=10.4 Hz, 1H), 4.14 (br, 1H), 7.08 (t, J=7.8 Hz, 1H), 7.25 (d, J=7.6 Hz, 1H), 7.31 (d, J=8 Hz, 1H), 7.49 (s, 1H).

<Synthesis (2) of Substituted Phenylthiopyrrolidine Analogue (III)>

Substituted phenylthiopyrrolidine analogue (17), a pyrrolidine analogue according to the third aspect of the invention (this compound is encompassed in the scope of the general formula (III)) can be synthesized following the reaction scheme shown below employing Mitsunobu reaction.

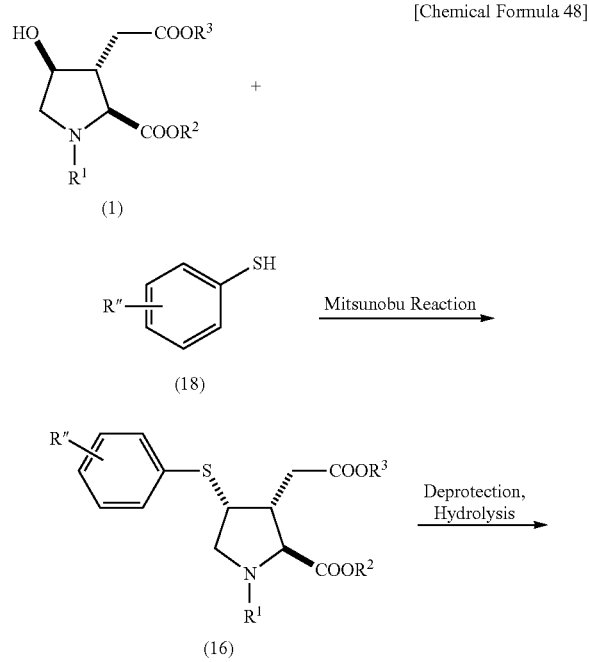

[Chemical Formula 48]

(Mitsunobu Reaction)

Specifically, as Mitsunobu reaction, dialkyl azodicarboxylate is first added dropwise to a solution of the compound (1) in THF, DMF or toluene containing triphenylphosphine and thiophenol derivative (18) that is commercially available or synthesized by any method known from documents, over several minutes to one hour at room temperature, and then they are allowed to react at 50° C. to obtain coupling compound (16).

(Deprotection Step)

Subsequently, as the deprotection step, substituted phenylthiopyrrolidine analogue (17) can be obtained by removing protective groups using any acid, similarly to Examples 13 through 16.

The above Synthesis (2) for substituted phenylthiopyrrolidine analogue (17) will be described in further detail, referencing Example 17 wherein specific reactions were performed.

EXAMPLE 17

In Example 17, (2S,3R,4R)-3-carboxy-methyl-4-(4-bromophenylthio)-pyrrolidine-2-carboxylate (IIIe) was synthesized by the method shown below.

1) Mitsunobu Reaction

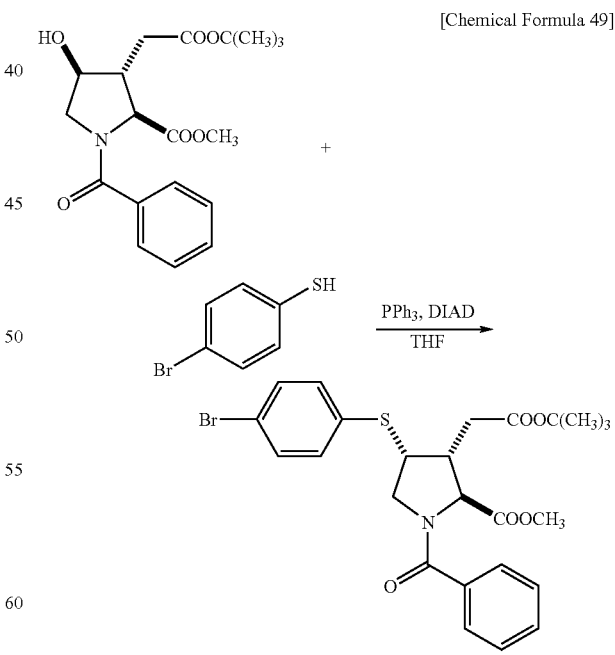

[Chemical Formula 49]

To a solution of methyl(2S,3R,4S)-1-benzoyl-3-(tert-butoxycarbonylmethyl)-4-hydroxypyrrolidine-2-carboxylate (56.8 mg, 156 μmol) in THF (1 mL), triphenylphosphine (102 mg, 389 μmol) and 4-bromothiophenol (62.0 mg, 328 μmol)

were added under the argon atmosphere. To this solution, diisopropyl azodicarboxylate (81 μL, 411 μmol) was slowly added dropwise, and the mixture was stirred at room temperature for 30 minutes. The reaction mixture was then concentrated in vacuo, and the residue was sequentially purified by column chromatography (silica gel 60, hexane/ethyl acetate=2/1) and thin layer chromatography (twice, silica gel 60, 0.5 mm, toluene/methanol=9/1 and hexane/ethyl acetate=3/1) to obtain the compound of interest (40 mg, 48%). TLC and $^1$H NMR data are shown below.

TLC: $R_f$=0.34 (silica gel, hexane/ethyl acetate=2/1)

$^1$H NMR (400 MHz, CDCl$_3$): (two rotamers) δ (ppm) 1.39 and 1.45 (s, 9H), 2.70 (dd, J=5.6 and 17.6 Hz, 1H), 2.81 (dd, J=9.2 and 17.6 Hz, 1H), 2.95-3.05 (m, 1H), 3.48 (br), 3.58 (br dd, J=2 and 11.2 Hz, 1H), 3.80 (s, 3H), 3.92-4.03 (complex), 4.46 (d, J=9.2 Hz, 1H), 7.10 (d, J=8.6 Hz, 2H), 7.31 (d, J=8.6 Hz, 2H), 7.35-7.47 (m), 7.52-7.57 (m).

2) Deprotection Step

[Chemical Formula 50]

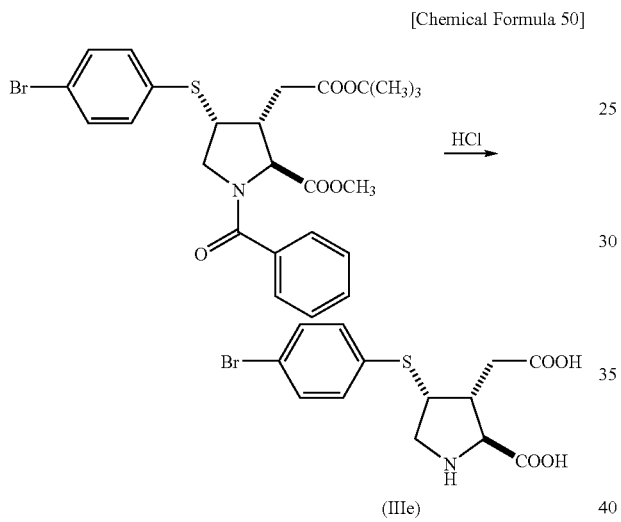

(IIIe)

Subsequently, the above reaction was performed as the deprotection step. Specifically, to methyl(2S,3R,4R)-1-benzoyl-4-(4-bromophenylthio)-3-(tert-butoxycarbonylmethyl)pyrrolidine-2-carboxylate (36.2 mg, 67.7 μmol), 6 M hydrochloric acid (2 mL) was added, and the mixture was refluxed with heating at 110° C. for 3 hours. The reaction solution, after cooled down to room temperature, was washed with chloroform, lyophilized, and the residue was purified by ion exchange chromatography (Dowex 50WX8) to obtain the compound of interest (IIIe) (21.7 mg, 89%). TLC and $^1$H NMR data are shown below.

TLC: $R_f$=0.72 (reverse phase, acetonitrile/water=1/1)

$^1$H NMR (400 MHz, D$_2$O): δ (ppm) 2.39 (dd, J=11.4 and 16.2 Hz, 1H), 2.62 (dd, J=4.2 and 16.2 Hz, 1H), 2.72-2.84 (m, 1H), 3.21 (d, J=12.4 Hz, 1H), 3.46 (dd, J=4.8 and 12.4 Hz, 1H), 3.76 (d, J=10 Hz, 1H), 4.09 (br, 1H), 7.22 (d, J=8.4 Hz, 2H), 7.37 (d, J=8.4 Hz, 2H).

<Synthesis (3) of Substituted Phenylthiopyrrolidine Analogue (III)>

Substituted phenylthiopyrrolidine analogue (17) (this compound is encompassed in the scope of the general formula (III)), a pyrrolidine analogue according to the third aspect of the invention, can also be synthesized according to the following reaction scheme.

[Chemical Formula 51]

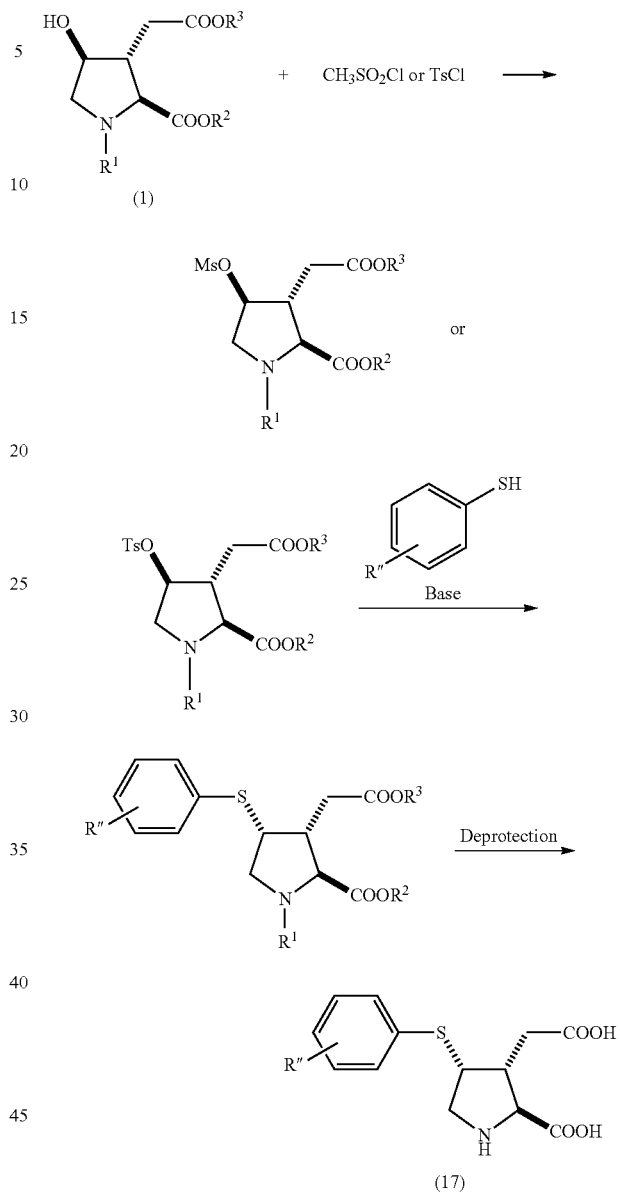

Specifically, as the leaving group formation step, the hydroxy group on pyrrolidine derivative (1) is first converted into any readily removable group (such as mesyl or tosyl group). Then, the group produced in the leaving group formation step is replaced with phenylthiolate or a phenylthiolate derivative to form a thioether derivative. As the next deprotection step, ester and cyano groups on the thioether derivative are hydrolyzed and $R^1$ is deprotected.

EXAMPLE 18

In Example 18, (2S,3R,4R)-3-carboxy-methyl-4-phenylthiopyrrolidine-2-carboxylate (IIIf) (see the structural formula below) was synthesized using phenylthiolate based on the synthesis (3) of the above substituted phenylthiopyrrolidine analogue (III).

[Chemical Formula 52]

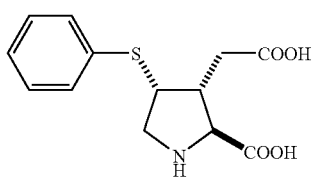

(IIIf)

<Synthesis of Substituted Phenylthiopyrrolidine Analogue (IV)>

Substituted phenylthiopyrrolidine analogue (20) (this compound is encompassed in the scope of the general formula (IV) described above), a pyrrolidine analogue according to the fourth aspect of the invention, can be synthesized according to the reaction scheme below.

[Chemical Formula 53]

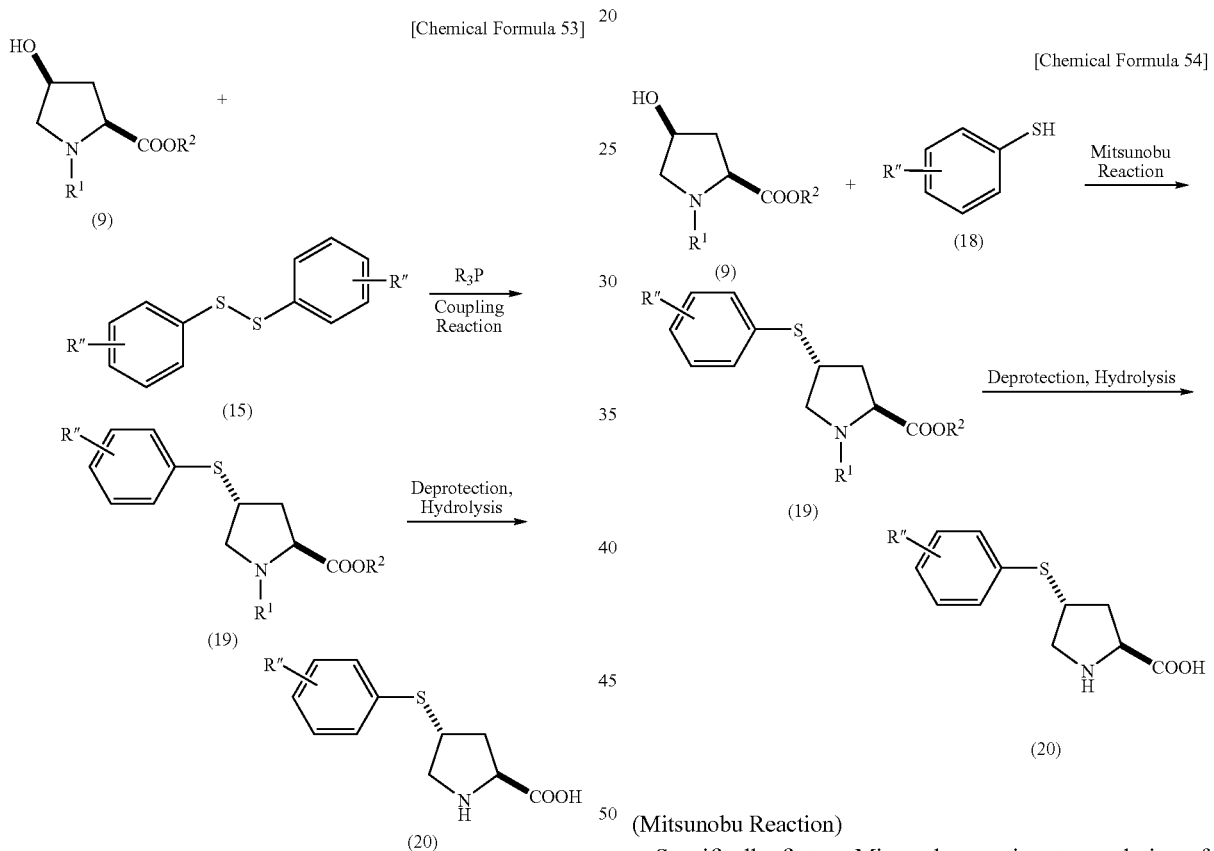

(Coupling Step)

As the coupling step, a solution of 4-hydroxyproline derivative (9), tributylphosphine, and substituted diphenyl disulfide (15), which is commercially available or synthesized according to any known method, in THF or DMF is heated to afford the coupling product (19).

(Deprotection Step)

Next, as the deprotection step, to the compound (19) synthesized in the above-described coupling step, 6 M through 12 M hydrochloric acid is added, then the mixture is refluxed with heating at 100° C. through 110° C. for several through 24 hours to obtain the deprotected compound (20). If any substituent that is susceptible to acid hydrolysis, such as amide group, is present on the benzene ring of the compound (19) and if $R^1$ is tert-butoxycarbonyl group, the compound (19) is dissolved in methanol, followed by addition of aqueous lithium hydroxide or sodium hydroxide, and the mixture is reacted at room temperature for several hours to several days, thereby hydrolyzing methyl esters. To the resultant compound, trifluoroacetic acid is then added at 0° C., and the temperature is raised to room temperature, thereby causing reaction for 30 minutes to 2 hours and obtaining the deprotected compound. If $R^1$ is a benzyloxycarbonyl group, hydrogenolysis with palladium catalyst results in deprotection of the amino group, and following alkali hydrolysis yields the deprotected compound of interest.

<Synthesis (2) of Substituted Phenylthiopyrrolidine Analogue (IV)>

Substituted phenylthiopyrrolidine analogue (20) (20 represents an analogue encompassed in the scope of the general formula (IV)), a pyrrolidine analogue according to the fourth aspect of the invention, can be synthesized also according to the reaction scheme shown below employing Mitsunobu reaction.

[Chemical Formula 54]

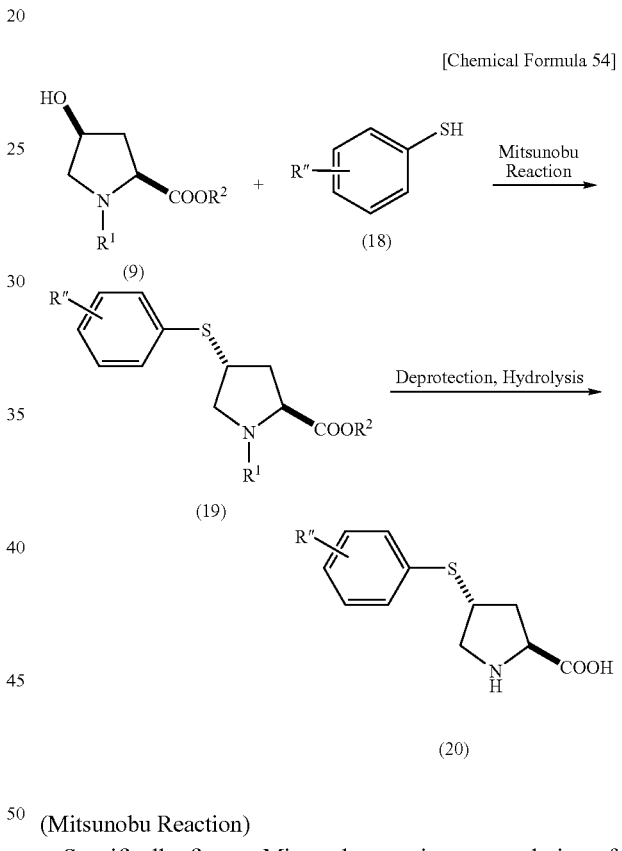

(Mitsunobu Reaction)

Specifically, first as Mitsunobu reaction, to a solution of compound (9), triphenylphosphine, and thiophenol derivative (18), which is commercially available or synthesized by a method known from any document, in THF, DMF or toluene, dialkyl azodicarboxylate is added dropwise at room temperature for several minutes through one hour, and then the mixture is allowed to react at room temperature through 50° C. to obtain a coupled compound (19).

(Deprotection Step)

Next, as the deprotection step, substituted phenylthiopyrrolidine analogue (20) is obtained by deprotection with acid in the same manner as in Examples 13 through 16.

The above Synthesis (1) for substituted phenylthiopyrrolidine analogue (IV) will be described in further detail, referencing Example 19 wherein specific reactions were performed.

EXAMPLE 19

In Example 19, (2S,4R)-4-(4-methylphenylthio)pyrrolidine-2-carboxylate (IVa) was synthesized by the method shown below.

1) Coupling Step

[Chemical Formula 55]

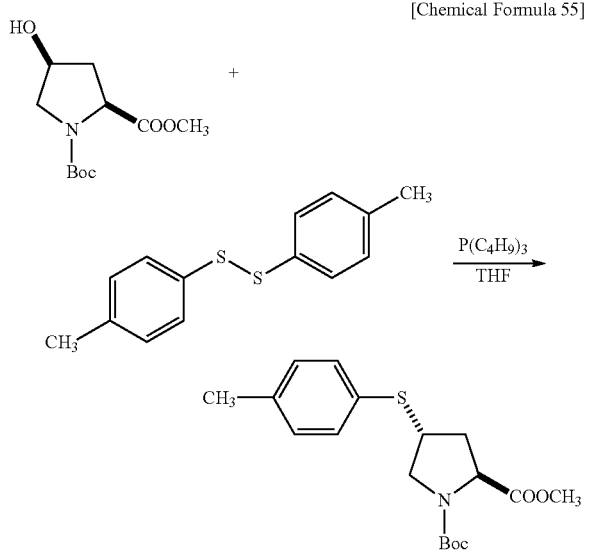

To a solution of methyl(2S,4S)-1-tert-butoxycarbonyl-4-hydroxypyrrolidine-2-carboxylate (40.3 mg, 164 μmol) in THF (1 mL), di-p-tolyl disulfide (124 mg, 503 μmol) and tributylphosphine (123 μL, 494 μmol) were added under the argon atmosphere, and the reaction solution was stirred at 80° C. for 22 hours. To the reaction mixture, after cooled down to room temperature, water was added, and the product was extracted with ethyl acetate and concentrated in vacuo, and the residue was purified by column chromatography (silica gel 60, hexane/ethyl acetate=4/1) to obtain the coupling product described above (54.0 mg, 94%). TLC and $^1$H NMR data are shown below.

TLC: $R_f$=0.30 (silica gel, hexane/ethyl acetate=4/1)

$^1$H NMR (400 MHz, CDCl$_3$): (two rotamers) δ (ppm) 1.40 and 1.45 (s, 9H), 2.15-2.30 (m, 2H), 2.34 and 2.35 (s, 3H), 3.36 (dd, J=6.5 and 10.8 Hz) and 3.44 (dd, J=6.3 and 11.1 Hz) (1H), 3.68-3.77 (complex, 1H), 3.72 and 3.72 (s, 3H), 3.83 (dd, J=6.8 and 10.8 Hz) and 3.87 (dd, J=6.7 and 11.1 Hz) (1H), 4.34 (t, J=6.6 Hz) and 4.43 (dd, J=4.6 and 8.1 Hz) (1H), 7.12 (d, J=7.8 Hz) and 7.14 (d, J=7.8 Hz) (2H), 7.32 (d, J=7.8 Hz, 2H).

2) Deprotection Step

[Chemical Formula 56]

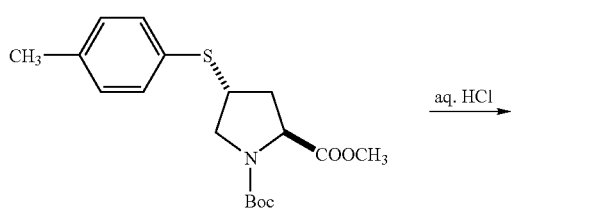

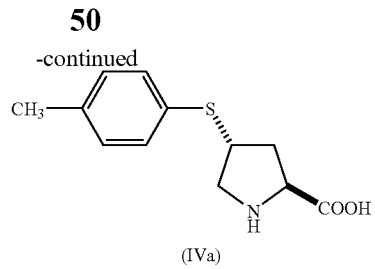

(IVa)

Subsequently, the above reaction was performed as the deprotection step. Specifically, to methyl(2S,4R)-1-tert-butoxycarbonyl-4-(4-methylphenylthio)pyrrolidine-2-carboxylate (41.6 mg, 118 μmol), 6 M hydrochloric acid (2 mL) was added, and the mixture was refluxed with heating at 110° C. for 5 hours. The reaction solution, after cooled down to room temperature, was washed with chloroform, lyophilized, and the residue was purified by ion exchange chromatography (Dowex 50WX8) to obtain the compound of interest (IVa) (21.6 mg, 77%). TLC and $^1$H NMR data are shown below.

TLC: $R_f$=0.59 (reverse phase, acetonitrile/water=1/1)

$^1$H NMR (400 MHz, D$_2$O): δ (ppm) 2.13 (s, 3H), 2.15-2.26 (m, 2H), 3.1 (dd, J=4.3 and 12.4 Hz, 1H), 3.48 (dd, J=6.1 and 12.4 Hz, 1H), 3.8-3.87 (m, 1H), 4.15 (t, J=8.3 Hz, 1H), 7.07 (d, J=8.2 Hz, 2H), 7.24 (d, J=8.2 Hz, 2H).

COMPARATIVE EXAMPLES 1 to 4

In Comparative Examples 1 to 4, compounds represented by the following structural formulae were synthesized.

[Chemical Formula 57]

Comparative Example 1

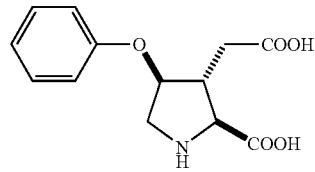

Comparative Example 2

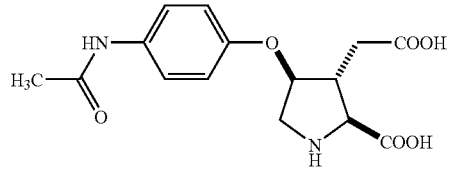

Comparative Example 3

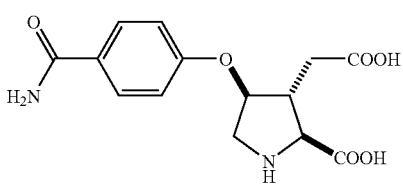

Comparative Example 4

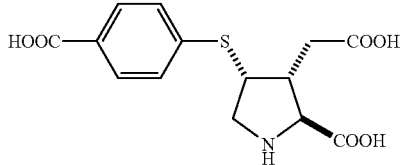

These compounds were obtained from the intermediates that were synthesized by similar methods to those of synthesizing substituted phenoxypyrrolidine analogues (I) and (III), according to the synthetic pathway shown below.
COMPARATIVE EXAMPLE 1
[Chemical Formula 58]
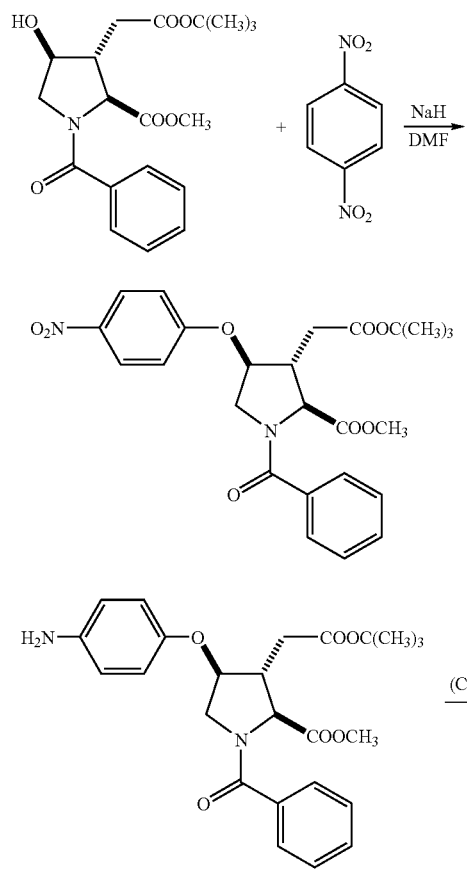
COMPARATIVE EXAMPLE 2
[Chemical Formula 59]
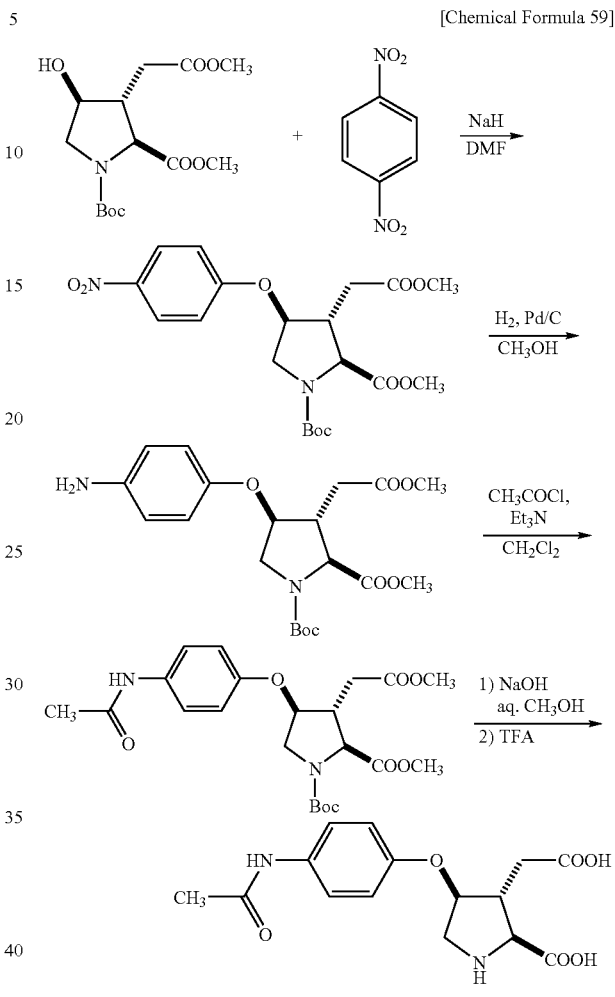
COMPARATIVE EXAMPLE 3
[Chemical Formula 60]
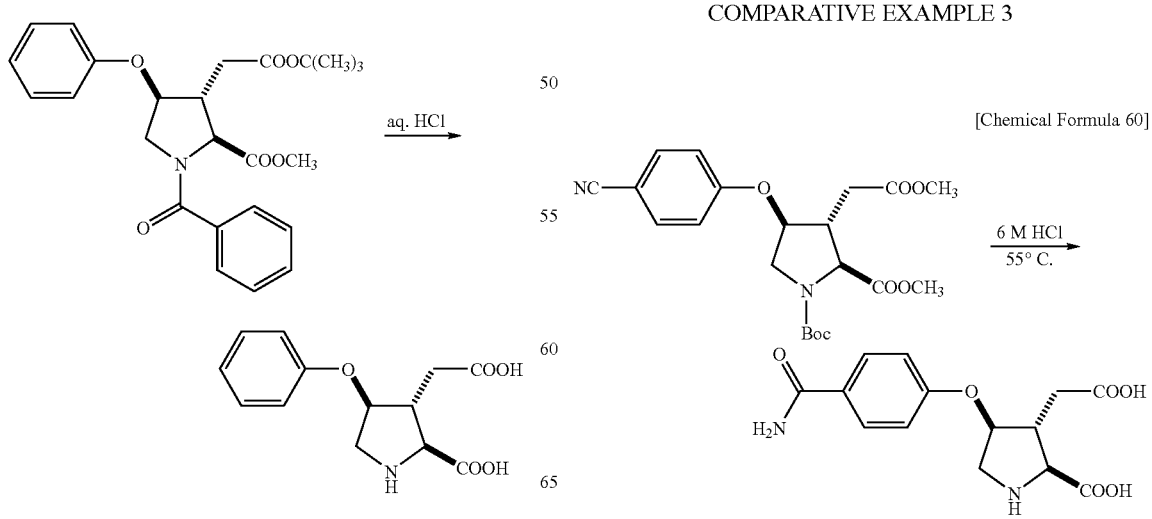

COMPARATIVE EXAMPLE 4

[Chemical Formula 61]

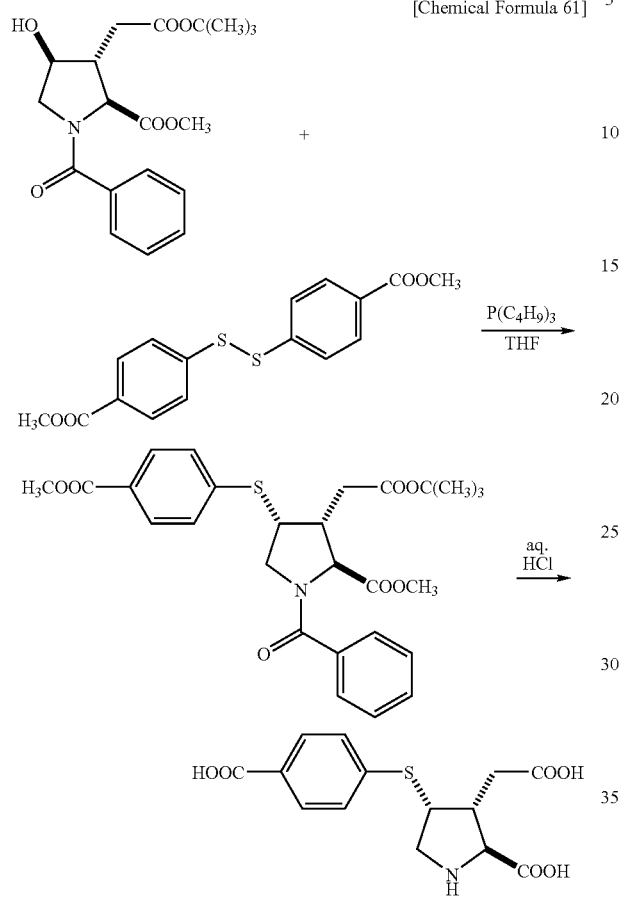

In Comparative Examples 5 and 6, compounds having the following structural formula were synthesized. The details are described below.

[Chemical Formula 62]

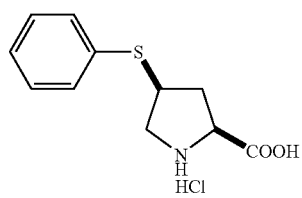

Comparative Example 5

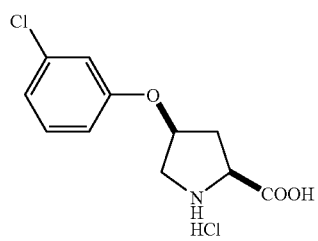

Comparative Example 6

COMPARATIVE EXAMPLE 5

The compound in Comparative Example 5 was synthesized according to the method described in the Patent document 2: ethyl(2S,4S)-1-tert-butoxycarbonyl-4-(phenylsulfanyl)pyrrolidine-2-carboxylate, prepared from ethyl(2S,4R)-1-tert-butoxycarbonyl-4-(4-toluenesulphonyloxy)-pyrrolidine-2-carboxylate and thiophenol, was hydrolyzed with sodium hydroxide and then the product was treated with 4 M hydrochloric acid in dioxane at room temperature for 2 hours to afford the deprotected compound.

[Chemical Formula 63]

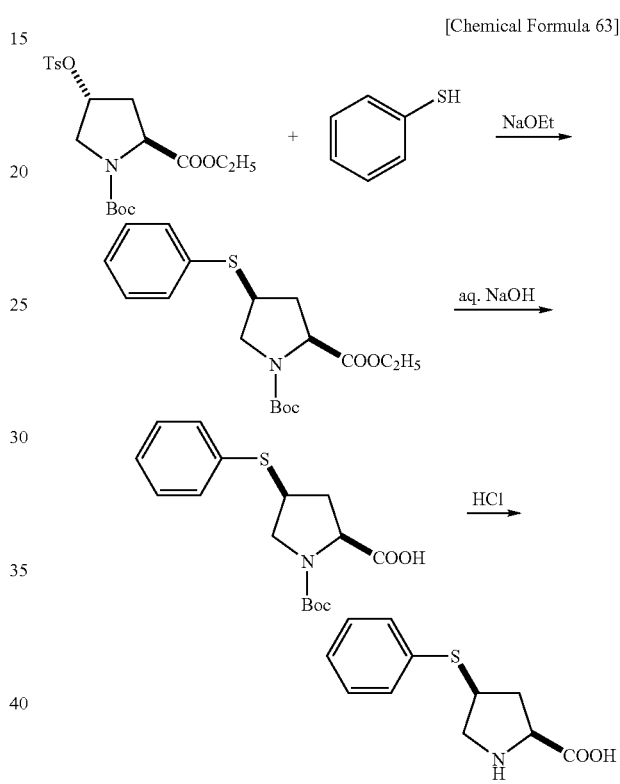

COMPARATIVE EXAMPLE 6

The compound according to Comparative Example 6 was synthesized according to the method described in the Patent document 2: methyl(2S,4S)-1-(tert-butoxycarbonyl)-4-(3-chlorophenoxy)pyrrolidine-2-carboxylate, prepared through Mitsunobu reaction of methyl(2S,4R)-1-tert-butoxycarbonyl-4-hydroxypyrrolidine-2-carboxylate and 3-chlorophenol, was hydrolyzed with lithium hydroxide and then the product was treated with 4 M hydrochloric acid in dioxane at 0° C. for 2 hours to afford the deprotected compound.

[Chemical Formula 64]

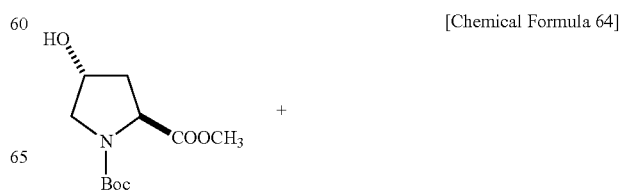

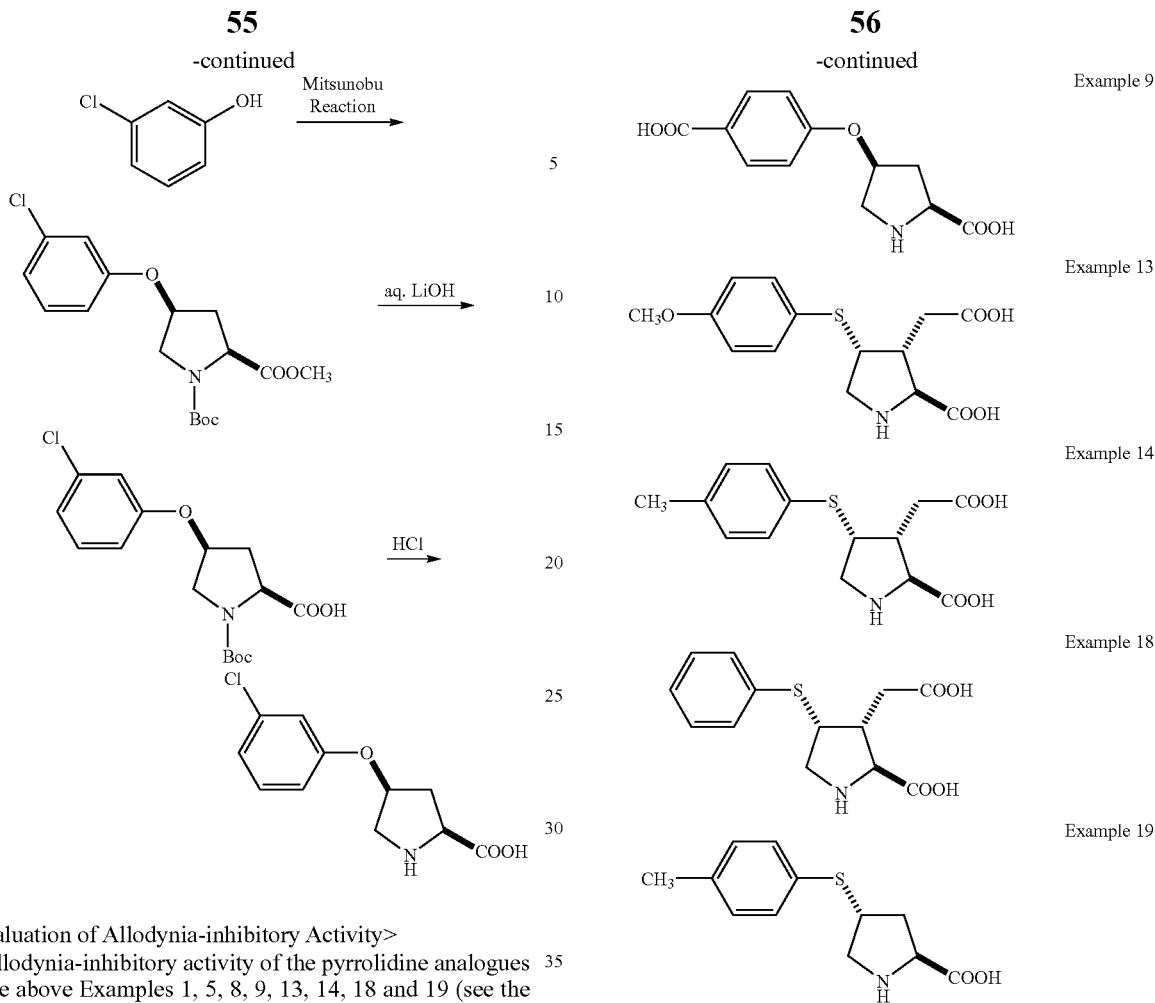

<Evaluation of Allodynia-inhibitory Activity>

Allodynia-inhibitory activity of the pyrrolidine analogues in the above Examples 1, 5, 8, 9, 13, 14, 18 and 19 (see the structural formulae below) and the above Comparative Examples 1 through 6 were evaluated.

[Chemical Formula 65]

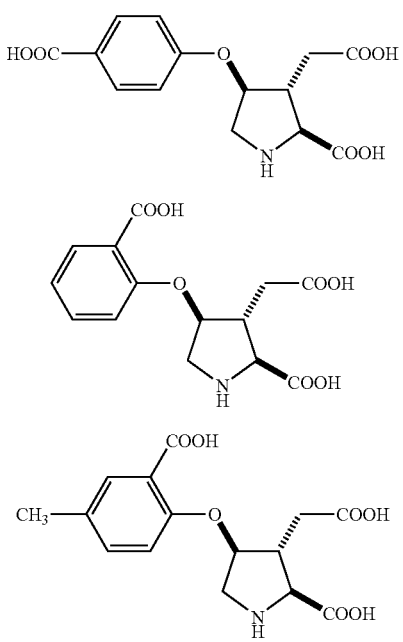

In the evaluation, according to the method of Hylden & Wilcox (Hylden, J. L. K. and Wilcox, G. L., Intrathecal morphine in mice: a new technique, Eur. J. Pharmacol, 67 (1980) 313-316.), 5 µl of a solution containing $1 \times 10^{-15}$ gram of acromelic acid and a different dose of pyrrolidine derivative was administrated to ddY-mouse (male, weight 22±2 g) under an unanesthetized condition. One experimental group consisted of 6 mice, and a solution containing $1 \times 10^{-15}$ gram of acromelic acid (5 µl) was administrated in control groups. After the compound was intrathecally administered, allodynia was assessed once every 5 minutes for 50 minutes by scoring the response in rank order from 0 to 2, and expressed as a percent of the values in control groups, similarly to the method of Yaksh & Harty et al. (Yaksh, T. L. and Harty, G. J., Pharmacology of the allodynia in rats evoked by high dose intrathecal morphine, J. Pharmacol. Exp. Ther., 244 (1988) 501-507.). Allodynic response was ranked as follows: 0, no response; 1, mild squeaking with attempts to move away from the stroking probe; 2, vigorous squeaking evoked by the stroking probe, biting at the probe or strong efforts to escape.

Figure 2:
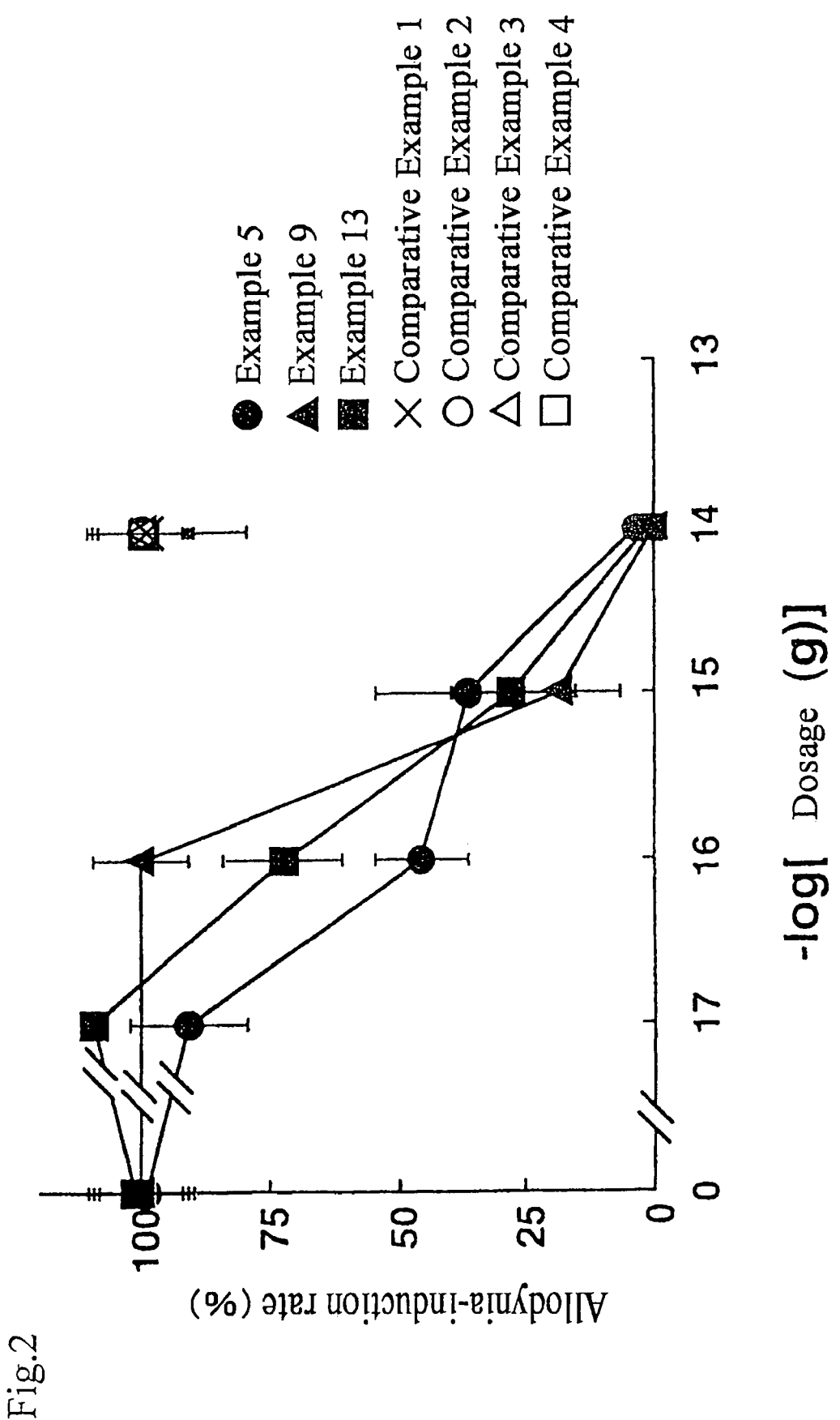
FIG. 2 shows the relationship between the percentage of allodynia induction and dosage of the pyrrolidine analogues of Examples 5, 9 and 13 and Comparative Examples 1 to 4.
Figure 3:
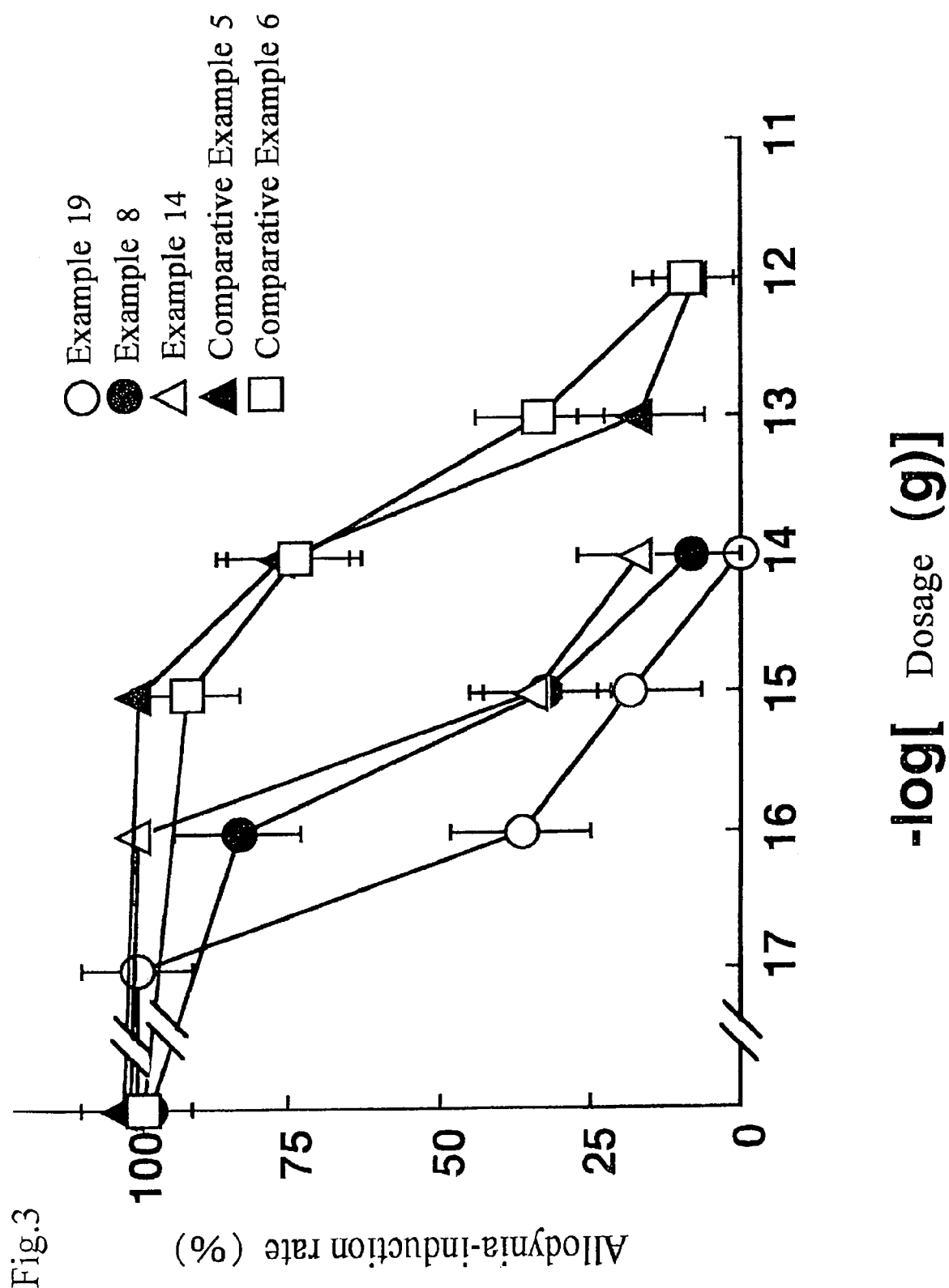
FIG. 3 shows the relationship between the percentage of allodynia induction and dosage of the pyrrolidine analogues of Examples 8, 14 and 19 and Comparative Examples 5 and 6.

The results are shown in FIGS. 1, 2 and 3, which disclose the following:

(1) As is seen in Examples 1, 5 and 8, the pyrrolidine analogues having an aromatic substituent via an oxygen atom at the 4-position, in which the aromatic substituent is cis to the carboxy group at the 2-position in contrast to acromelic acid and bears a carboxy group at any position of the benzene ring, exhibit strong allodynia-inhibitory activity. On the other hand, as is seen in Comparative Examples 1 through 3, the pyrrolidine analogues lacking the carboxy group on the aromatic substituent at the 4-position described above do not exhibit any allodynia-inhibitory activity.

(2) As is seen in Example 9, the pyrrolidine analogues having an aromatic substituent via an oxygen atom at the 4-position, in which the aromatic substituent is cis to the carboxy group at the 2-position in contrast to acromelic acid and bears a carboxy group at any position of the benzene ring, even if they lack the carboxymethyl group at the 3-position, exhibit strong allodynia-inhibitory activity.

(3) As is seen in Examples 13, 14 and 18, the pyrrolidine analogues that have a sulfur atom instead of oxygen, to which an aromatic substituent not having a carboxy group on the benzene ring is bonded, on the carbon at the 4-position with an opposite configuration to the compound of Example 1, exhibit strong allodynia-inhibitory activity. On the other hand, as is seen in Comparative Example 4, the pyrrolidine analogue bearing a carboxy group on the aromatic substituent bonded to the sulfur atom at the 4-position do not exhibit any allodynia-inhibitory activity.

(4) As is seen in Example 19, the pyrrolidine analogues that have a sulfur atom instead of oxygen, to which an aromatic substituent not having a carboxy group on the benzene ring is bonded, on the carbon at the 4-position with an opposite configuration to the compound of Example 1, even if they lack the carboxymethyl group at the 3-position, exhibit strong allodynia-inhibitory activity.

(5) Furthermore, the pyrrolidine analogues of Examples 8, 14 and 19 suppress the allodynia induction at an order of approximately one-hundredth of the doses with equal potency to the compounds of Comparative Examples 5 and 6 described in the Patent documents 1 and 2, demonstrating the superior anti-allodynic efficacy of the compounds.

It can be naturally estimated based on the conventional state-of-the-art that, in place of the exact compounds used in the above Examples, any salts thereof can be used to achieve similar results. Also, any ester form of the compounds used in Examples may be used as pro-drug, as a matter of course.

<Pyrrolidine Analogues conjugated with Molecular Probe Functional Group>

The pyrrolidine analogues and agents for preventing neuropathic pain according to the present invention may facilitate analysis of receptor function by conjugating to the benzene ring any functional group that has a function of molecular probe as a clue. Exemplary substituents having a function of molecular probe include fluorescent substituents and substituents which are labeled with any isotope such as $^3$H, $^{11}$C, and $^{18}$F.

For example, compounds can be produced by the method summarized in the following reaction scheme, in which the benzene ring is substituted with ultraviolet light-reactive phenylazide group or biochemically detectable biotin group. Such a compound can be used as a photoaffinity labelling probe in capture and identification of receptors under examination, facilitating studies of neuropathic pain and development of pharmaceuticals.

[Chemical Formula 66]

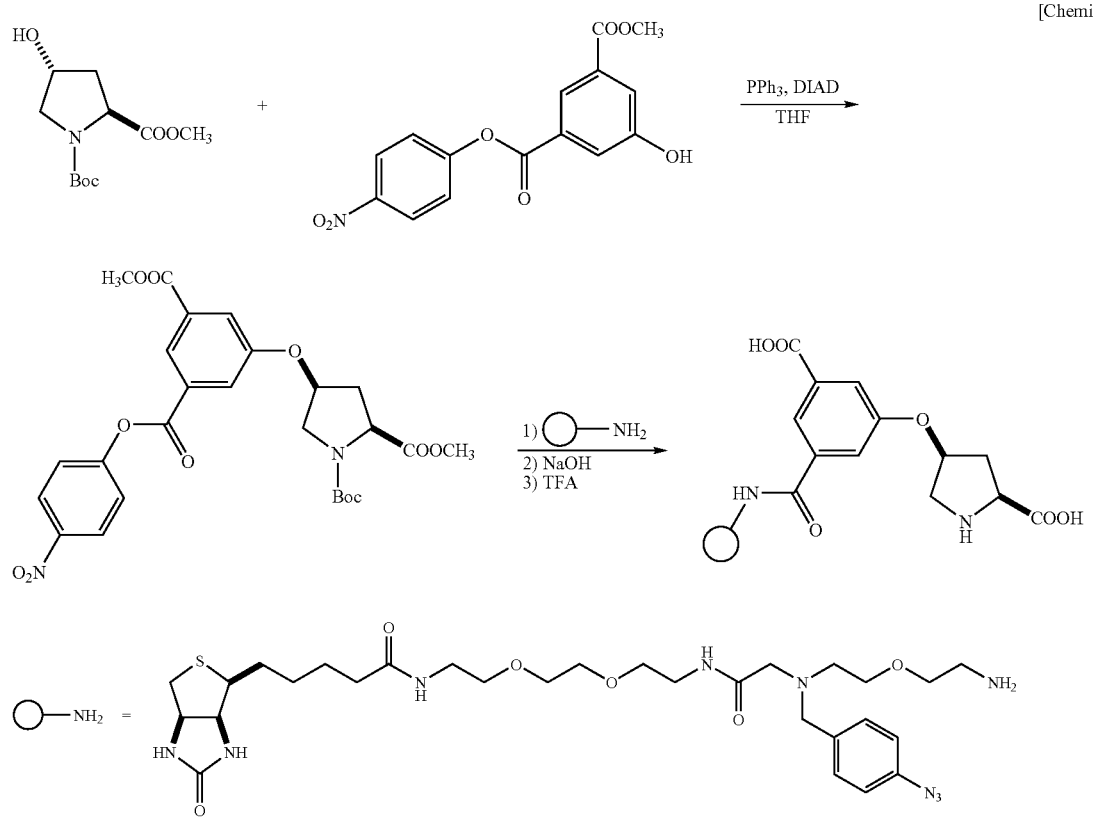

Alternatively, compounds can be produced by the method summarized in the following reaction scheme, in which the benzene ring is substituted with radioactive element such as tritium. Such a compound can be used as a radioactive probe for studying distribution of drugs and substrate in cells and body tissues, and binding affinity of a drug for receptors, for example.

[Chemical Formula 67]

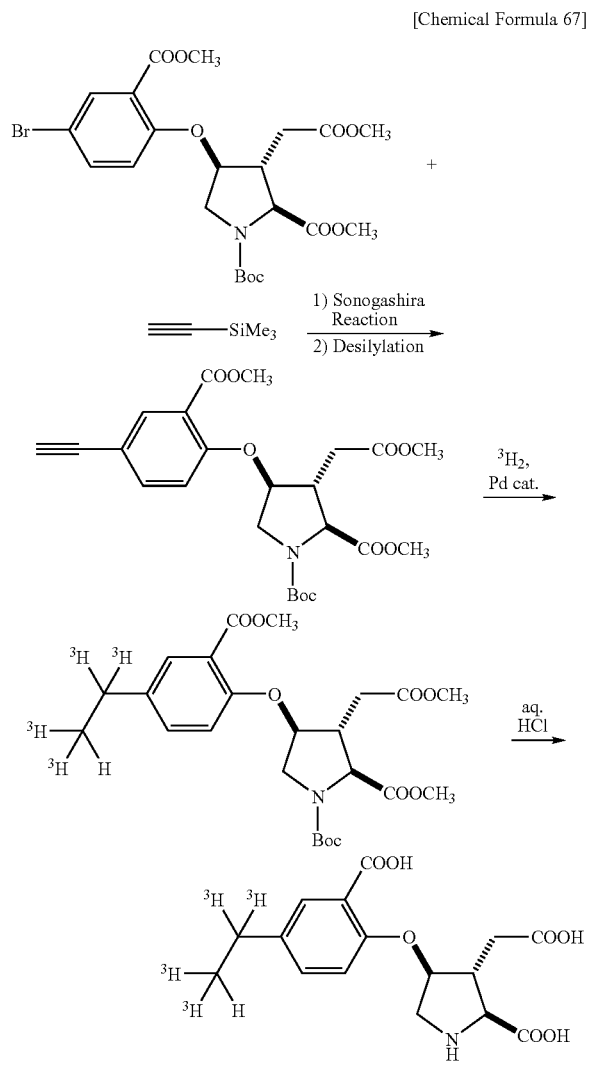

Moreover, compounds can be produced by the method summarized in the following reaction scheme, in which the benzene ring is substituted with positron emitting isotope such as $^{11}C$ and $^{18}F$. Such a compound can be used as a PET probe in positron emission computed tomography (PET) for in vivo pharmacokinetic analysis and receptor occupancy measurements to facilitate studies of neuropathic pain, development of pharmaceuticals, and the like.

[Chemical Formula 68]

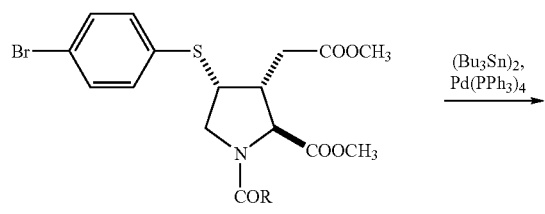

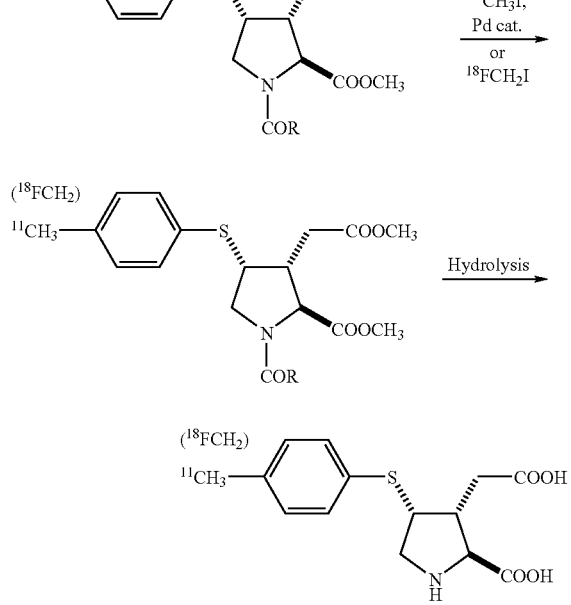

The present invention is not limited in any way by the description of the Examples of the invention described above. A variety of the alteration and modification within the scope which is readily thought of by those who skilled in the art without departing from the description in the claims are encompassed in the present invention.

INDUSTRIAL APPLICABILITY

The present invention is applicable to studies of neuropathic pain, development of pharmaceuticals, and the like.

The invention claimed is:

1. A pyrrolidine which is (2S, 3R, 4R)-3-(carboxymethyl)-4-(4-methoxyphenylthio)-pyrrolidine-2-carboxylate or (2S, 3R, 4R)-3-(carboxymethyl)-4-(4-methylphenylthio)-pyrrolidine-2-carboxylate.

2. An agent for inhibiting allodynia which comprises as an active ingredient a pyrrolidine according to claim 1.

3. A method for producing the pyrrolidine described in claim 1, comprising the steps of;

performing the step of coupling by coupling a pyrrolidine derivative represented by the formula (1), wherein $R^1$ represents a protective group for amino group, and $COOR^2$ and $COOR^3$ represent an ester group; and diphenyl disulfide or diphenyl disulfide derivative (15), wherein R" represents $CH_3O$ or $CH_3$ with each other under the presence of phosphine reagent to form a thioether derivative represented by the formula (16), with inversion of stereochemistry, and performing the step of deprotection by hydrolyzing the ester group of the thioether derivative represented by the formula (16), and deprotecting $R^1$

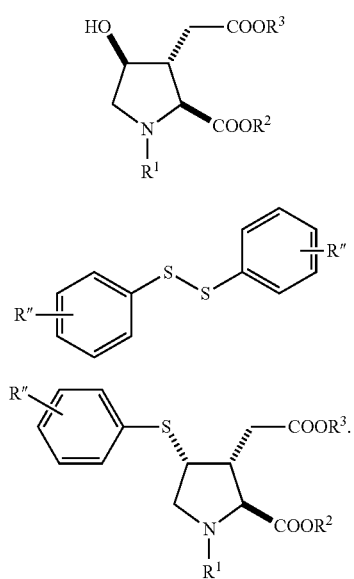

4. A method for producing the pyrrolidine described in claim 1, comprising the steps of;
performing the step of Mitsunobu reaction by bringing a pyrrolidine derivative represented by the general formula (1), wherein $R^1$ represents a protective group for amino group, and $COOR^2$ and $COOR^3$ represent an ester group; and thiophenol or substituted thiophenol (18), wherein R" represents CH$_3$O or CH$_3$ into Mitsunobu reaction to form a thioether derivative represented by the formula (16), with inversion of stereochemistry, and
performing the step of deprotection by hydrolyzing the ester group of the thioether derivative represented by the formula (16), and deprotecting $R^1$

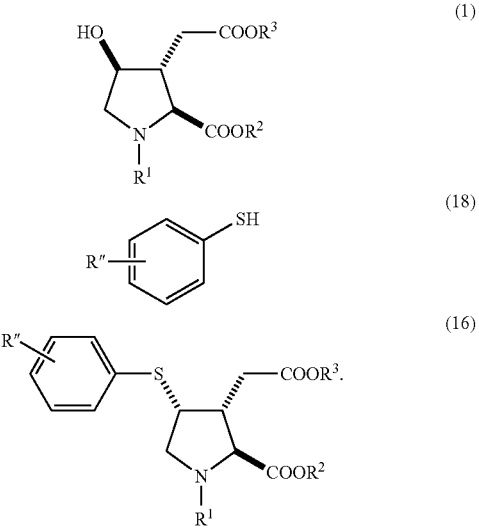

* * * * *